United States Patent
Ochiai et al.

(10) Patent No.: US 10,202,469 B2
(45) Date of Patent: Feb. 12, 2019

(54) SUGAR CHAIN-ATTACHED LINKER, COMPOUND CONTAINING SUGAR CHAIN-ATTACHED LINKER AND PHYSIOLOGICALLY ACTIVE SUBSTANCE OR SALT THEREOF, AND METHOD FOR PRODUCING SAME

(71) Applicant: Glytech, Inc., Kyoto (JP)

(72) Inventors: Hirofumi Ochiai, Kyoto (JP); Kenta Yoshida, Hyogo (JP)

(73) Assignee: Glytech, Inc., Kyoto-shi, Kyoto (KP)

( * ) Notice: Subject to any disclaimer, the term of this patent is extended or adjusted under 35 U.S.C. 154(b) by 20 days.

(21) Appl. No.: 14/647,702

(22) PCT Filed: Nov. 21, 2013

(86) PCT No.: PCT/JP2013/081347
§ 371 (c)(1),
(2) Date: May 27, 2015

(87) PCT Pub. No.: WO2014/084110
PCT Pub. Date: Jun. 5, 2014

(65) Prior Publication Data
US 2015/0306235 A1    Oct. 29, 2015

(30) Foreign Application Priority Data

Nov. 30, 2012 (JP) ................. 2012-263752

(51) Int. Cl.
| | | |
|---|---|---|
| C07K 7/06 | (2006.01) | |
| A61K 38/08 | (2006.01) | |
| A61K 47/54 | (2017.01) | |
| A61K 47/61 | (2017.01) | |
| A61K 47/64 | (2017.01) | |
| C07K 1/107 | (2006.01) | |
| C07K 14/71 | (2006.01) | |
| C08B 37/00 | (2006.01) | |

(52) U.S. Cl.
CPC .......... *C08B 37/0063* (2013.01); *A61K 38/08* (2013.01); *A61K 47/549* (2017.08); *A61K 47/61* (2017.08); *A61K 47/64* (2017.08); *C07K 7/06* (2013.01); *C07K 14/71* (2013.01); *C07K 1/1077* (2013.01)

(58) Field of Classification Search
None
See application file for complete search history.

(56) References Cited

U.S. PATENT DOCUMENTS

| | | | |
|---|---|---|---|
| 2003/0045716 A1 | 3/2003 | Natrajan | |
| 2012/0296078 A1* | 11/2012 | Kang | C08B 3/06 536/66 |
| 2013/0045716 A1 | 2/2013 | Niu | |

FOREIGN PATENT DOCUMENTS

| | | |
|---|---|---|
| CN | 102256990 A | 11/2011 |
| JP | 1-294638 A | 11/1989 |
| JP | 4-76001 A | 3/1992 |
| JP | 5-39306 A | 2/1993 |
| JP | 6-80705 A | 3/1994 |
| JP | 2001505872 A | 5/2001 |
| JP | 2001509144 A | 7/2001 |
| JP | 2007501870 A | 2/2007 |
| JP | 2007530569 A | 11/2007 |
| WO | 2006095775 A1 | 9/2006 |
| WO | 2007114454 A1 | 10/2007 |
| WO | 2008155900 A1 | 12/2008 |
| WO | 2009095479 A2 | 8/2009 |
| WO | 2009153960 A1 | 12/2009 |
| WO | 2011007747 A1 | 1/2011 |
| WO | 2011052523 A1 | 5/2011 |

OTHER PUBLICATIONS

Xue, Tetrahedron Letters 43, (2002) 1599-1602.*
Khan, Journal of Polymer Science: Part A: Polymer Chemistry, vol. 46, 2326-2334, 2008.*
Imamura, Heterocycles (2004), 64, 51-56, abstract only.*
Imamura (Heterocycles (2004), 64, 51-56, CAPLUS record.*
Wadhwa, Bioconjugate Chem. 1995, 6, 283-291.*
Chiu, The Journal of Biological Chemistry, vol. 270, No. 41, Issue of Oct. 13, pp. 24024-24031, 1995.*
Chinese Patent Application No. 201380071159.6, First Office Action, dated Jun. 20, 2016, 15 pages.
Abdu-Allah et al., "Design, Synthesis and Structure-Affinity Relationships of Novel Series of Sialosides as CD22-Specific Inhibitors", Journal of Medicinal Chemistry, vol. 51,No. 21, Nov. 13, 2008, pp. 6665-6681.
Yadav et al, "Carbohydrate Functionalized Iron(iii) Complexes as Biomimetic Siderophores", Chemical Communications-Chemcom., vol. 48, No. 11, Jan. 1, 2012, p. 1704.
Nagy, et al. "-(4-Substituted-benzoyl)—(—glucopyranosyl) Ureas as Inhibitors of Glycogen Phosphorylase: Synthesis and Evaluation by Kinetic, Crystallographic, and Molecular Modelling Methods", Bioorganic & Medicinal Chemistry, vol. 20, No. 5, Dec. 29, 2011, pp. 1801-1816.
Somsak, et al., "Assessment of Synthetic Methods for the Preparationof N-Beta-D-Glucopyranosyl-N'-Substituted Ureas, -Thioureas and Related Compounds", Carbohyorate Research, vol. 343, No. 12, Aug. 11, 2008, pp. 2083-2093.

(Continued)

*Primary Examiner* — Layla D Berry
(74) *Attorney, Agent, or Firm* — Dennis A. Bennett; John Desper

(57) ABSTRACT

To provide a carrier linker that is capable of improving the water solubility of a physiologically active substance and more quickly releasing the physiologically active substance under specific conditions without utilizing light or enzymatic cleavage.
[Solution]
A novel sugar chain-attached linker comprising a sugar chain that is attached as a carrier.

27 Claims, 3 Drawing Sheets

Specification includes a Sequence Listing.

(56) References Cited

OTHER PUBLICATIONS

Geurtsen, et al.,"Chemoselective Glycosylation Strategy for the Convergent Assembly of Phytoalexin-Elicitor Active Oligosaccharides and Their Photoreactive Derivatives", The Journal of Organic Chemistry, vol. 64, No. 21, Oct. 1, 1999, pp. 7828-7835.
Bryne et al., "Sialic Acids: Carbohydrate Moieties that Influence the Biological and Physical Properties of Biopharmaceutical Proteins and Living Cells," Drug Discovery Today, vol. 12, Issues 7-8, Apr. 2007, pp. 319-326.
Darren et al., "Boc SPPS of Two Hydrophobic Peptides Using a "Solubilising Tail" Strategy: Dodecaalanine and Chemotactic Protein 10," Tetrahedron Letters, 1996, vol. 37, No. 46, pp. 8431-8434.
Fishkin et al., "A Novel Pathway for Maytansinoid Release from Thiother Linked ANti-Body Drug Conjugates (ACDs) Under Oxidative Conditions," Chemical Communications, 2011, vol. 47, No. 38, pp. 10752-10754.
Hossain et al., "Use of Temporary "Solubilizing" Peptide Tag for the Fmoc Solid-Phase Synthesis of Human Insulin Glargine via Use of Regioselective Disulfide Bond Formation," Bioconjugate Chemistry, 2009, vol. 20, No. 7, pp. 1390-1396.
International Search Report, PCT Application No. PCT/JP2013/081347, dated Jun. 5, 2014, 2 pgs.
Kurtoglu et al., "Drug Release Characteristics of PAMAM Dendrimer-Drug Conjugates with Difference Linkers," International Journal of Pharmaceutics, 2010, vol. 384, No. 1-2, pp. 189-194.
Schmittberger et al., "Sunthesis of the Palmitoylated and Prenylated C-Terminal Lipopeptides of the Humnan R- and N-Ras Proteins," Bioorganic and Medicinal Chemistry, 1999, vol. 7, No. 5, pp. 749-762.

* cited by examiner

[Figure 1A]
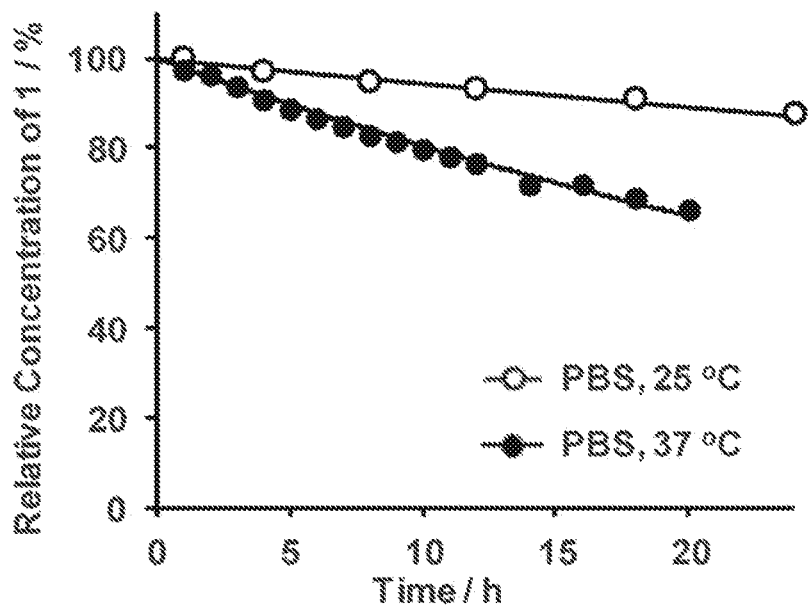
[Figure 1B]
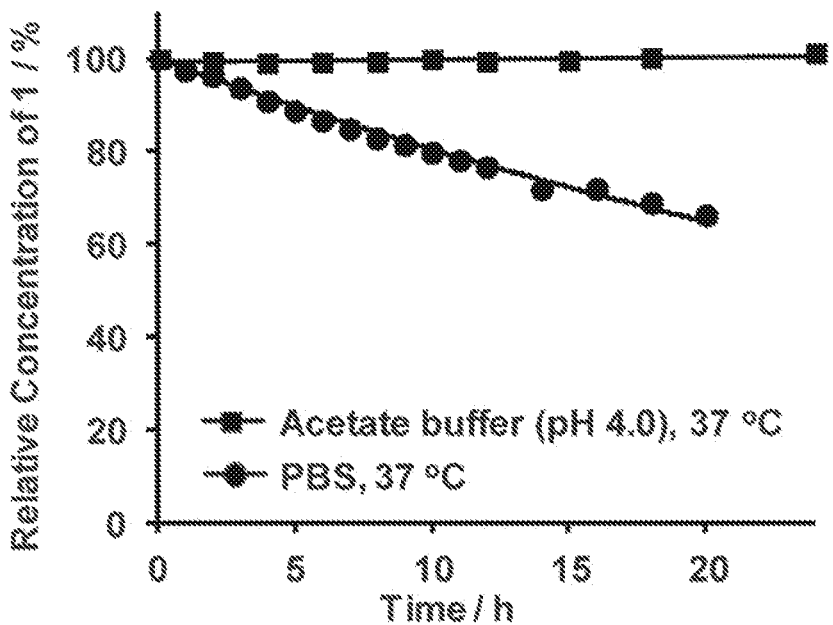

[Figure 2A]
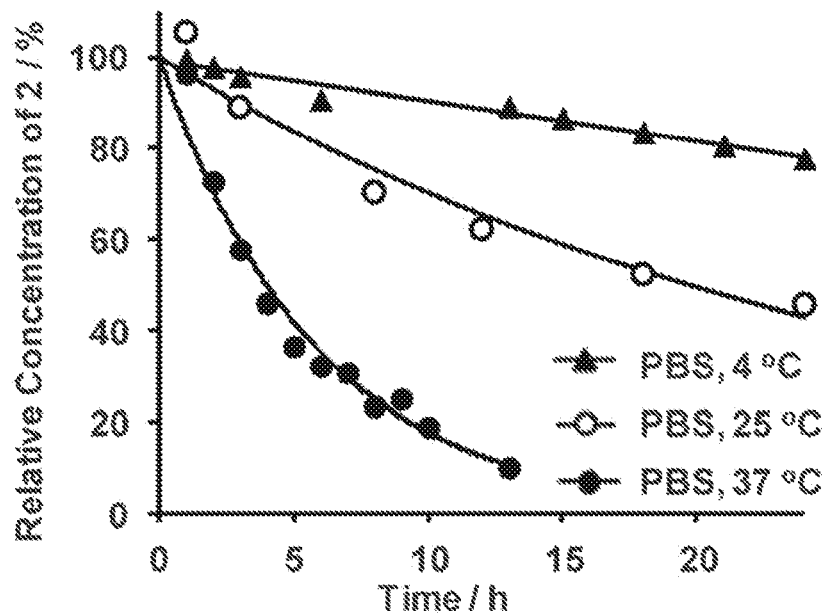
[Figure 2B]
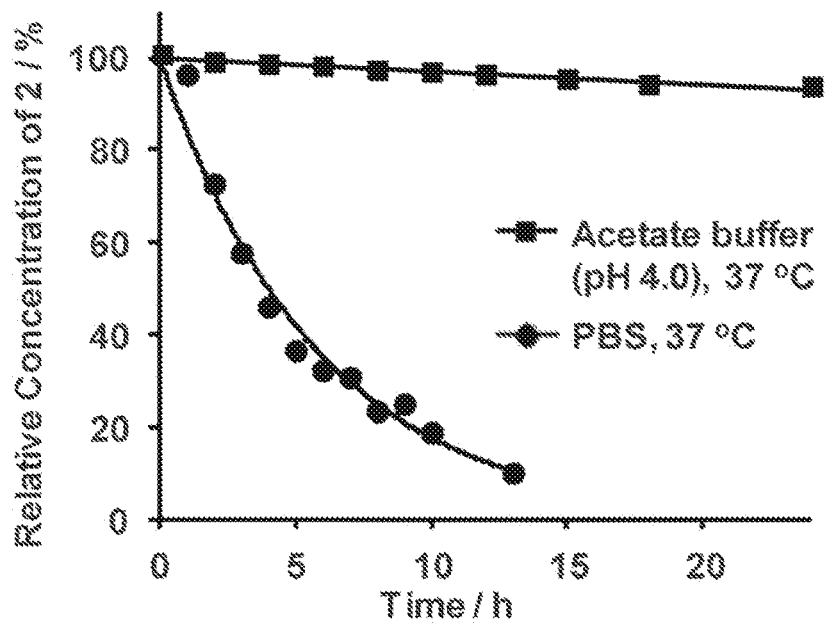

[Figure 3]
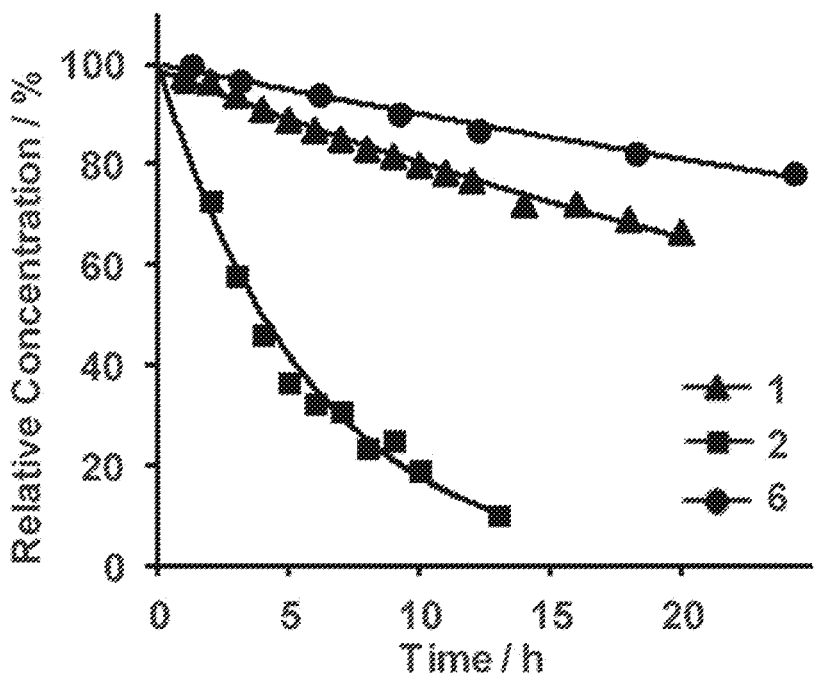
[Figure 4]
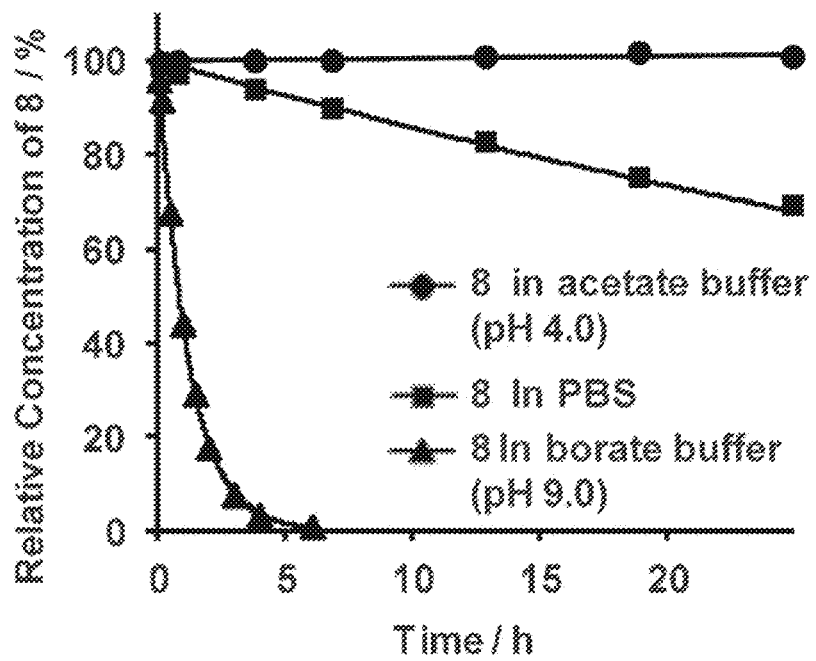

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (1)..(1)
<223> OTHER INFORMATION: Fmoc group
<220> FEATURE:
<221> NAME/KEY: BINDING
<222> LOCATION: (1)..(1)
<223> OTHER INFORMATION: Pbf group
<220> FEATURE:
<221> NAME/KEY: BINDING
<222> LOCATION: (2)..(2)
<223> OTHER INFORMATION: Boc group
<220> FEATURE:
<221> NAME/KEY: BINDING
<222> LOCATION: (9)..(9)
<223> OTHER INFORMATION: HMBA-Cys(Trt) type linker moiety bonding to
      Resin

<400> SEQUENCE: 1

Arg Trp Gly Leu Leu Leu Ala Leu Leu
1               5

<210> SEQ ID NO 2
<211> LENGTH: 9
<212> TYPE: PRT
<213> ORGANISM: Artificial
```

```
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: HMBA-Cys type linker moiety

<400> SEQUENCE: 2

Arg Trp Gly Leu Leu Leu Ala Leu Leu
1               5

<210> SEQ ID NO 3
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: HMBA-Cys(asialo) type linker moiety

<400> SEQUENCE: 3

Arg Trp Gly Leu Leu Leu Ala Leu Leu
1               5

<210> SEQ ID NO 4
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: HMBA-Cys(disialo) type linker moiety

<400> SEQUENCE: 4

Arg Trp Gly Leu Leu Leu Ala Leu Leu
1               5

<210> SEQ ID NO 5
<211> LENGTH: 9
<212> TYPE: PRT
<213> ORGANISM: Artificial
<220> FEATURE:
<223> OTHER INFORMATION: Chemically synthesized

<400> SEQUENCE: 5

Arg Trp Gly Leu Leu Leu Ala Leu Leu
1               5

<210> SEQ ID NO 6
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (1)..(1)
<223> OTHER INFORMATION: Fmoc group
<220> FEATURE:
<221> NAME/KEY: BINDING
<222> LOCATION: (1)..(1)
<223> OTHER INFORMATION: Pbf group
<220> FEATURE:
<221> NAME/KEY: BINDING
<222> LOCATION: (2)..(2)
<223> OTHER INFORMATION: Boc group
<220> FEATURE:
```

```
<221> NAME/KEY: BINDING
<222> LOCATION: (9)..(9)
<223> OTHER INFORMATION: HMBA-Cys(StBu) type linker moiety bonding to
      Resin

<400> SEQUENCE: 6

Arg Trp Gly Leu Leu Leu Ala Leu Leu
1               5

<210> SEQ ID NO 7
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (1)..(1)
<223> OTHER INFORMATION: Fmoc group
<220> FEATURE:
<221> NAME/KEY: BINDING
<222> LOCATION: (1)..(1)
<223> OTHER INFORMATION: Pbf group
<220> FEATURE:
<221> NAME/KEY: BINDING
<222> LOCATION: (2)..(2)
<223> OTHER INFORMATION: Boc group
<220> FEATURE:
<221> NAME/KEY: BINDING
<222> LOCATION: (9)..(9)
<223> OTHER INFORMATION: HMBA-Cys type linker moiety bonding to Resin

<400> SEQUENCE: 7

Arg Trp Gly Leu Leu Leu Ala Leu Leu
1               5

<210> SEQ ID NO 8
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: HMBA-Cys(asialo) type linker moiety bonding to
      Resin

<400> SEQUENCE: 8

Arg Trp Gly Leu Leu Leu Ala Leu Leu
1               5

<210> SEQ ID NO 9
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (1)..(1)
<223> OTHER INFORMATION: Boc group
<220> FEATURE:
<221> NAME/KEY: BINDING
<222> LOCATION: (1)..(1)
<223> OTHER INFORMATION: Pbf group
<220> FEATURE:
<221> NAME/KEY: BINDING
<222> LOCATION: (2)..(2)
<223> OTHER INFORMATION: Boc group

<400> SEQUENCE: 9
```

```
Arg Trp Gly Leu Leu Leu Ala Leu Leu
1               5

<210> SEQ ID NO 10
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: SCH2CH2SCH2CONH(asialo) type linker moiety

<400> SEQUENCE: 10

Arg Trp Gly Leu Leu Leu Ala Leu Leu
1               5

<210> SEQ ID NO 11
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: 4-thiobenzoic acid-Asn(asialo)-Gly type linker
      moiety

<400> SEQUENCE: 11

Arg Trp Gly Leu Leu Leu Ala Leu Leu
1               5

<210> SEQ ID NO 12
<211> LENGTH: 9
<212> TYPE: PRT
<213> ORGANISM: Homo sapiens

<400> SEQUENCE: 12

Tyr Phe Pro Gly Gln Phe Ala Phe Ser
1               5

<210> SEQ ID NO 13
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (1)..(1)
<223> OTHER INFORMATION: Fmoc group
<220> FEATURE:
<221> NAME/KEY: BINDING
<222> LOCATION: (1)..(1)
<223> OTHER INFORMATION: tBu group
<220> FEATURE:
<221> NAME/KEY: BINDING
<222> LOCATION: (5)..(5)
<223> OTHER INFORMATION: Trt group
<220> FEATURE:
<221> NAME/KEY: BINDING
<222> LOCATION: (9)..(9)
<223> OTHER INFORMATION: tBu group
<220> FEATURE:
<221> NAME/KEY: BINDING
<222> LOCATION: (9)..(9)
<223> OTHER INFORMATION: HMBA-Cys(Trt) type linker moiety bonding to
      Resin

<400> SEQUENCE: 13
```

```
Tyr Phe Pro Gly Gln Phe Ala Phe Ser
1               5

<210> SEQ ID NO 14
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: HMBA-Cys type linker moiety

<400> SEQUENCE: 14

Tyr Phe Pro Gly Gln Phe Ala Phe Ser
1               5

<210> SEQ ID NO 15
<211> LENGTH: 9
<212> TYPE: PRT
<213> ORGANISM: Artificial
<220> FEATURE:
<223> OTHER INFORMATION: chemically synthesized
<220> FEATURE:
<221> NAME/KEY: BINDING
<222> LOCATION: (9)..(9)
<223> OTHER INFORMATION: HMBA-Cys(disialo) type linker moiety

<400> SEQUENCE: 15

Tyr Phe Pro Gly Gln Phe Ala Phe Ser
1               5
```

SUGAR CHAIN-ATTACHED LINKER, COMPOUND CONTAINING SUGAR CHAIN-ATTACHED LINKER AND PHYSIOLOGICALLY ACTIVE SUBSTANCE OR SALT THEREOF, AND METHOD FOR PRODUCING SAME

This application is a U.S. National Stage Application under 35 U.S.C. § 371 of International Application No. PCT/JP2013/081347, filed Nov. 21, 2013, which claims priority to Japan Application No. JP 2012-263752 filed Nov. 30, 2012. Each of the above-referenced applications is expressly incorporated by reference herein its entirety.

The present invention relates to a glycosylated linker, a compound comprising a glycosylated linker and a physiologically active substance, or a salt thereof, and a method for producing the same.

BACKGROUND ART

In recent years, various vaccines have been developed using physiologically active substances. Some of these physiologically active substances, however, cannot be (sufficiently) filter-sterilized, for example, due to their low water solubility. Also, some physiologically active substances are difficult to dissolve in an aqueous solution or an emulsion prepared from the aqueous solution for administration to organisms such as humans.

Various methods have been attempted to improve the water solubility of drugs such as physiologically active substances. For example, a carrier-drug conjugate (so-called drug derivative) is known in which a highly water-soluble carrier is artificially added directly to a drug. A hydrophilic amino acid sequence or polyethylene glycol (PEG), etc., is known as the carrier.

Such a drug derivative, however, in which a carrier is bonded directly to a drug, differs in steric structure from the original drug. The resulting drug derivative exhibits different pharmacokinetic, immunogenic, toxicological, or pharmacological properties compared with the original drug molecule. Particularly, when the drug derivative is used as, for example, a vaccine, the antigenicity of this drug derivative is well known to be usually lower than that of the original drug molecule.

A drug with PEG added as a carrier (PEGylated drug) is resistant to biodegradation. Thus, the PEGylated drug, when continuously administered into an organism, has the risk of accumulating in the organism to cause chemical injury to the organism; thus its biocompatibility is still less than sufficient (Patent Literature 1). Furthermore, PEG has a molecular weight distribution (polydisperse nature). The PEGylation of drugs forms many monomeric isoforms (many different monomeric isoforms: structurally different proteins having the same functions), because of the difference in the binding site or molecular weight of added PEG. These formed isoforms might compete with each other for binding to a drug acceptor molecule (Non Patent Literature 1).

A carrier-linker-drug conjugate has also been developed in which a drug and a carrier are bonded via a linker moiety. This conjugate can be designed such that the bond between the carrier-linker moiety and the drug is cleaved upon acting on a target site (in blood, etc.) to release the drug itself. In the case of using such a carrier-linker-drug conjugate, light or enzymatic cleavage has been used as a trigger for the cleavage of the bond between the carrier-linker moiety and the drug. Unfortunately, for the use of the light, the light irradiation to the target site is difficult, and damage to the organism is also a concern. Alternatively, in the case of the enzymatic cleavage, the amount of an enzyme is known to largely differ not only among individuals but depending on administration sites. Thus, the problem of this approach is to cause variations in the effect of the drug therapy among patients.

In response to these problems, a carrier-linker-drug conjugate has been reported in which a carrier-linker moiety is bonded via an amide group to a physiologically active substance moiety (Patent Literature 2). The technique disclosed in Patent Literature 2 utilizes autohydrolysis based on an intramolecular catalytic effect in the carrier-linker moiety so as to control the cleavage of the bond between the carrier-linker moiety and the drug. The mechanism underlying the cleavage of the bond between the carrier-linker moiety and the physiologically active substance moiety is based on the cyclization-activation resulting from cyclic imide formation for cleavage of the amide bond.

CITATION LIST

Patent Literature

[Patent Literature 1] National Publication of International Patent Application No. 2007-530569
[Patent Literature 2] International Publication No. WO 2009/095479

Non Patent Literature

[Non Patent Literature 1] Barry Byrne et al., Drug Discovery Today, (2007), Vol. 12, pp. 319-326

SUMMARY OF INVENTION

Technical Problem

In light of the problems as described above, an object of the present invention is to provide a carrier-linker that can improve the water solubility of a physiologically active substance and is capable of releasing the physiologically active substance more rapidly under particular conditions.

Solution to Problem

Patent Literature 2 has merely confirmed that a large number of carrier-linker-drug conjugates having various structures each release the drug itself by the cleavage of the amide bond. Patent Literature 1 has not focused on the biodegradability of a carrier, because the literature shows a large number of Examples in which PEG is used as a carrier. In addition, Patent Literature 1 has not mentioned the solubility of a carrier-linker-drug conjugate or a carrier-linker itself, because the literature shows a large number of Examples in which poorly water-soluble higher fatty acid is used as a carrier.

As a result of conducting diligent studies, the present inventors have found a carrier-linker that improves the water solubility of a physiologically active substance and is capable of releasing the physiologically active substance under particular conditions independent of light or enzymatic cleavage.

Specifically, in one aspect, the present invention provides a glycosylated linker for bonding to a physiologically active substance having at least one carboxy group, wherein the glycosylated linker is represented by the following formula (A):

$$X-R^1-Y-R^2 \qquad (A)$$

wherein

X represents an oxygen atom (O) having a leaving group or a sulfur atom (S) having a leaving group;

$R^1$ is substituted or unsubstituted $C_1$-$C_5$ alkyl, substituted or unsubstituted $C_5$-$C_{16}$ aryl, substituted or unsubstituted $C_5$-$C_{16}$ heteroaryl, substituted or unsubstituted $C_2$-$C_5$ alkenyl, or substituted or unsubstituted $C_2$-$C_5$ alkynyl, or $R^1$ represents —$R^3$—$R^4$—, —$R^4$—$R^5$—, or —$R^3$—$R^4$—$R^5$—, wherein $R^3$ and $R^5$ each represent substituted or unsubstituted $C_1$-$C_5$ alkyl, substituted or unsubstituted $C_2$-$C_5$ alkenyl, or substituted or unsubstituted $C_2$-$C_5$ alkynyl, and $R^4$ represents substituted or unsubstituted $C_5$-$C_{16}$ aryl, substituted or unsubstituted $C_5$-$C_{16}$ heteroaryl, or a sulfur atom (S);

Y may be present or absent, and when Y is present, Y represents —CO— or —CONH— (provided that C is bonded to $R^1$ and N is bonded to $R^2$); and $R^2$ is a sugar chain, a glycosylated amino acid, or a glycosylated polypeptide, or $R^2$ represents —$R^6$—$R^7$, wherein $R^6$ represents a sugar chain, a glycosylated amino acid, or a glycosylated polypeptide, and $R^2$ represents a hydrogen atom (H), —$NH_2$, substituted or unsubstituted $C_1$-$C_5$ alkyl, substituted or unsubstituted $C_5$-$C_{16}$ aryl, substituted or unsubstituted $C_5$-$C_{16}$ heteroaryl, a nucleic acid, or PEG, and the glycosylated linker becomes capable of binding to the carboxy group of the physiologically active substance by the elimination of the leaving group in the oxygen atom (O) or the sulfur atom (S).

According to one embodiment of the glycosylated linker of the present invention, the glycosylated linker is a glycosylated linker represented by the following formula (A):

X—$R^1$—Y—$R^2$  (A)

wherein

X represents a sulfur atom (S) having a leaving group;

$R^1$ represents —$R^3$—$R^4$—, —$R^4$—$R^5$—, or —$R^3$—$R^4$—$R^5$—, wherein $R^3$ and $R^5$ each represent substituted or unsubstituted $C_1$-$C_5$ alkyl, substituted or unsubstituted $C_2$-$C_5$ alkenyl, or substituted or unsubstituted $C_2$-$C_5$ alkynyl, and $R^4$ represents substituted or unsubstituted $C_5$-$C_{16}$ aryl, substituted or unsubstituted $C_5$-$C_{16}$ heteroaryl, or a sulfur atom (S);

Y may be present or absent, and when Y is present, Y represents —CO— or —CONH— (provided that C is bonded to $R^1$ and N is bonded to $R^2$); and $R^2$ represents a sugar chain, a glycosylated amino acid, or a glycosylated polypeptide.

According to one embodiment of the glycosylated linker of the present invention, the glycosylated linker is a glycosylated linker represented by the following formula (A):

X—$R^1$—Y—$R^2$  (A)

wherein

X represents an oxygen atom (O) having a leaving group or a sulfur atom (S) having a leaving group;

$R^1$ represents —$R^3$—$R^4$— or —$R^4$—$R^5$—, wherein $R^3$ and $R^5$ each represent substituted or unsubstituted $C_1$-$C_5$ alkyl, substituted or unsubstituted $C_2$-$C_5$ alkenyl, or substituted or unsubstituted $C_2$-$C_5$ alkynyl, and $R^4$ represents substituted or unsubstituted $C_5$-$C_{16}$ aryl or substituted or unsubstituted $C_5$-$C_{16}$ heteroaryl;

Y may be present or absent, and when Y is present, Y represents —CO— or —CONH— (provided that C is bonded to $R^1$ and N is bonded to $R^2$); and $R^2$ represents a sugar chain, a glycosylated amino acid, or a glycosylated polypeptide.

According to one embodiment of the glycosylated linker of the present invention, the sugar chain in the "glycosylated amino acid or glycosylated polypeptide" represented by $R^2$ or $R^6$ in the glycosylated linker is bonded to Asn or Cys in the amino acid or the polypeptide.

According to one embodiment of the glycosylated linker of the present invention, the sugar chain in the "sugar chain, glycosylated amino acid, or glycosylated polypeptide" represented by $R^2$ or $R^6$ in the glycosylated linker consists of 4 or more sugar residues.

According to one embodiment of the glycosylated linker of the present invention, the sugar chain in the "sugar chain, glycosylated amino acid, or glycosylated polypeptide" represented by $R^2$ or $R^6$ in the glycosylated linker is a biantennary complex-type sugar chain, a triantennary complex-type sugar chain, or a tetraantennary complex-type sugar chain.

According to one embodiment of the glycosylated linker of the present invention, the sugar chain in the glycosylated linker is a biantennary complex-type sugar chain selected from the group consisting of a disialo sugar chain, a monosialo sugar chain, an asialo sugar chain, a di-GlcNAc sugar chain, and a dimannose sugar chain.

According to one embodiment of the glycosylated linker of the present invention, the sugar chain in the "sugar chain, glycosylated amino acid, or glycosylated polypeptide" represented by $R^2$ or $R^6$ in the glycosylated linker is a sugar chain represented by the following formula:

[Formula 1]

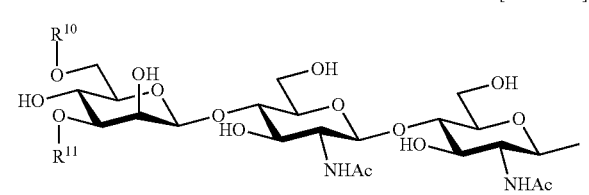

wherein $R^{10}$ and $R^{11}$ are the same or different and each represent

[Formula 2]

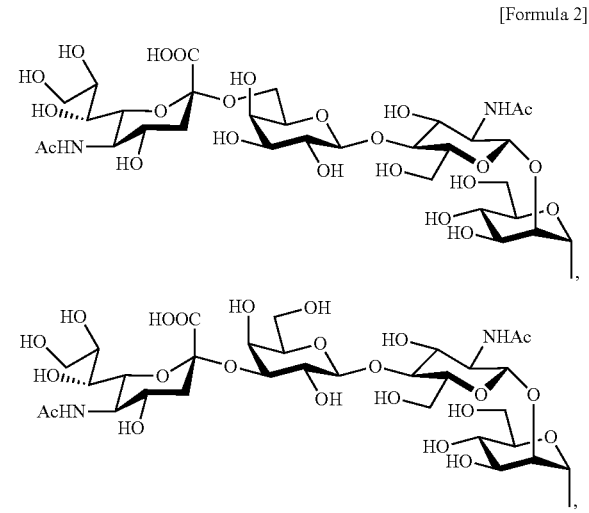

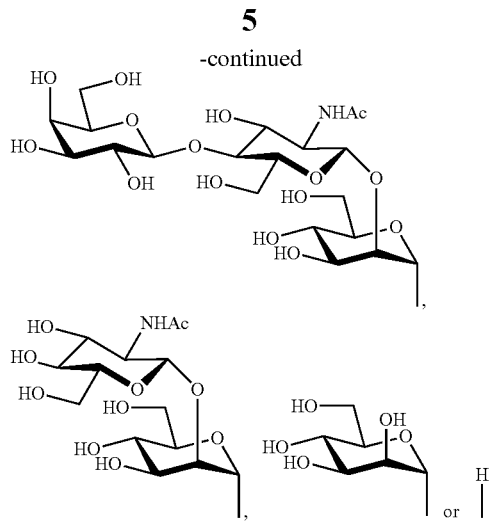

and Ac represents an acetyl group.

According to one embodiment of the glycosylated linker of the present invention, the sugar chain in the "glycosylated amino acid or glycosylated polypeptide" in the glycosylated linker is bonded to the amino acid or the polypeptide without the mediation of a linker.

One or any combination of two or more of the features of the present invention mentioned above is also included in the scope of the glycosylated linker of the present invention, as a matter of course.

In another aspect, the present invention provides a compound comprising a glycosylated linker moiety derived from a glycosylated linker and a physiologically active substance moiety, or a salt thereof, wherein the physiologically active substance has at least one carboxy group, and the glycosylated linker moiety is bonded to the physiologically active substance moiety through an ester bond or a thioester bond formed with the carboxy group of the physiologically active substance moiety by the elimination of the leaving group in the oxygen atom (O) or the sulfur atom (S).

According to one embodiment of the compound of the present invention or the salt thereof, the physiologically active substance in the compound or the salt thereof is a low-molecular physiologically active substance or a biopolymer.

According to one embodiment of the compound of the present invention or the salt thereof, the biopolymer in the compound or the salt thereof is selected from the group consisting of a protein, a polypeptide, a polynucleotide, and a peptide nucleic acid.

According to one embodiment of the compound of the present invention or the salt thereof, the compound or the salt thereof has improved water solubility compared with an unmodified physiologically active substance.

According to one embodiment of the compound of the present invention or the salt thereof, the improved water solubility of the compound or the salt thereof is 10 to 1,000,000 times the water solubility of the "unmodified physiologically active substance" in terms of molar concentration.

According to one embodiment of the compound of the present invention or the salt thereof, the ester bond or the thioester bond formed between the oxygen atom (O) or the sulfur atom (S) in the glycosylated linker moiety and the carboxy group in the physiologically active substance moiety in the compound or the salt thereof is cleaved in a manner dependent on pH and/or temperature.

One or any combination of two or more of the features of the present invention mentioned above is also included in the scope of the compound comprising a glycosylated linker moiety and a physiologically active substance moiety according to the present invention, or the salt thereof, as a matter of course.

In an alternative aspect, the present invention provides a composition comprising the compound or the salt thereof, wherein sugar chains in the compound or the salt thereof are substantially homogeneous.

In an alternative aspect, the present invention provides a pharmaceutical composition comprising (I) the compound according to claim 10 or the salt thereof, and (II) a pharmacologically acceptable carrier.

According to one embodiment of the pharmaceutical composition of the present invention, the physiologically active substance in the pharmaceutical composition exerts its activity after administration to a subject.

According to one embodiment of the pharmaceutical composition of the present invention, the pharmaceutical composition is used in vaccination.

One or any combination of two or more of the features of the present invention mentioned above is also included in the scope of the pharmaceutical composition of the present invention, as a matter of course.

In an alternative aspect, the present invention provides a method for producing a compound comprising a glycosylated linker moiety and a physiologically active substance moiety, or a salt thereof, wherein the glycosylated linker is represented by the following formula (A):

wherein

X represents an oxygen atom (O) having a leaving group or a sulfur atom (S) having a leaving group;

$R^1$ is substituted or unsubstituted $C_1$-$C_5$ alkyl, substituted or unsubstituted $C_5$-$C_{16}$ aryl, substituted or unsubstituted $C_5$-$C_{16}$ heteroaryl, substituted or unsubstituted $C_2$-$C_5$ alkenyl, or substituted or unsubstituted $C_2$-$C_5$ alkynyl, or $R^1$ represents —$R^3$—$R^4$—, —$R^4$—$R^5$—, or —$R^3$—$R^4$—$R^5$—, wherein $R^3$ and $R^5$ each represent substituted or unsubstituted $C_1$-$C_5$ alkyl, substituted or unsubstituted $C_2$-$C_5$ alkenyl, or substituted or unsubstituted $C_2$-$C_5$ alkynyl, and $R^4$ represents substituted or unsubstituted $C_5$-$C_{16}$ aryl, substituted or unsubstituted $C_5$-$C_{16}$ heteroaryl, or a sulfur atom (S);

Y may be present or absent, and when Y is present, Y represents —CO— or —CONH— (provided that C is bonded to $R^1$ and N is bonded to $R^2$); and $R^2$ is a sugar chain, a glycosylated amino acid, or a glycosylated polypeptide, or $R^2$ represents —$R^6$—$R^7$, wherein $R^6$ represents a sugar chain, a glycosylated amino acid, or a glycosylated polypeptide, and $R^2$ represents a hydrogen atom (H), substituted or unsubstituted $C_1$-$C_5$ alkyl, substituted or unsubstituted $C_5$-$C_{16}$ aryl, substituted or unsubstituted $C_5$-$C_{16}$ heteroaryl, a nucleic acid, or PEG, and the physiologically active substance has at least one carboxy group, the method comprising the following step:

(a) carrying out condensation reaction so as to form an ester bond or a thioester bond between the oxygen atom (O)

or the sulfur atom (S) having a leaving group in the glycosylated linker and the carboxy group of the physiologically active substance.

According to one embodiment of the method for producing a compound comprising a glycosylated linker moiety and a physiologically active substance moiety, or a salt thereof according to the present invention, the step of carrying out condensation reaction in the production method is carried out in a state where the glycosylated linker is bonded to a resin for solid-phase synthesis (but only in the case where the glycosylated linker has a glycosylated amino acid or a glycosylated polypeptide).

According to one embodiment of the method for producing a compound comprising a glycosylated linker moiety and a physiologically active substance moiety, or a salt thereof according to the present invention, the production method further comprises, before the step (a), the step of (a') preparing the glycosylated linker represented by the following formula (A):

wherein

X represents an oxygen atom (O) having a leaving group or a sulfur atom (S) having a leaving group;

$R^1$ is substituted or unsubstituted $C_1$-$C_5$ alkyl, substituted or unsubstituted $C_5$-$C_{16}$ aryl, substituted or unsubstituted $C_5$-$C_{16}$ heteroaryl, substituted or unsubstituted $C_2$-$C_5$ alkenyl, or substituted or unsubstituted $C_2$-$C_5$ alkynyl, or $R^1$ represents $—R^3—R^4—$, $—R^4—R^5—$, or $—R^3—R^4—R^5—$, wherein $R^3$ and $R^5$ each represent substituted or unsubstituted $C_1$-$C_5$ alkyl, substituted or unsubstituted $C_2$-$C_5$ alkenyl, or substituted or unsubstituted $C_2$-$C_5$ alkynyl, and $R^4$ represents substituted or unsubstituted $C_5$-$C_{16}$ aryl, substituted or unsubstituted $C_5$-$C_{16}$ heteroaryl, or a sulfur atom (S);

Y may be present or absent, and when Y is present, Y represents —CO— or —CONH— (provided that C is bonded to $R^1$ and N is bonded to $R^2$); and $R^2$ is a sugar chain, a glycosylated amino acid, or a glycosylated polypeptide, or $R^2$ represents $—R^6—R^7$, wherein $R^6$ represents a sugar chain, a glycosylated amino acid, or a glycosylated polypeptide, and $R^2$ represents a hydrogen atom (H), substituted or unsubstituted $C_1$-$C_5$ alkyl, substituted or unsubstituted $C_5$-$C_{16}$ aryl, substituted or unsubstituted $C_5$-$C_{16}$ heteroaryl, a nucleic acid, or PEG.

According to one embodiment of the method for producing a compound comprising a glycosylated linker moiety and a physiologically active substance moiety, or a salt thereof according to the present invention, the step (a') and/or the step (a) in the production method is carried out on a resin.

According to one embodiment of the method for producing a compound comprising a glycosylated linker moiety and a physiologically active substance moiety, or a salt thereof according to the present invention, in the production method, the physiologically active substance has at least one carboxy group, the method comprising the following steps:

(a) bonding a linker represented by the following formula (B) to a resin, the linker being represented by the following formula (B):

wherein

X represents an oxygen atom (O) having a leaving group or a sulfur atom (S) having a leaving group;

$R^1$ is substituted or unsubstituted $C_1$-$C_5$ alkyl, substituted or unsubstituted $C_5$-$C_{16}$ aryl, substituted or unsubstituted $C_5$-$C_{16}$ heteroaryl, substituted or unsubstituted $C_2$-$C_5$ alkenyl, or substituted or unsubstituted $C_2$-$C_5$ alkynyl, or $R^1$ represents $—R^3—R^4—$, $—R^4—R^5—$, or $—R^3—R^4—R^5—$, wherein $R^3$ and $R^5$ each represent substituted or unsubstituted $C_1$-$C_5$ alkyl, substituted or unsubstituted $C_2$ alkenyl, or substituted or unsubstituted $C_2$-$C_5$ alkynyl, and $R^4$ represents substituted or unsubstituted $C_5$-$C_{16}$ aryl, substituted or unsubstituted $C_5$-$C_{16}$ heteroaryl, or a sulfur atom (S);

Y may be present or absent, and when Y is present, Y represents —CO— or —CONH— (provided that C is bonded to $R^1$ and N is bonded to $R^2$); and $R^2$ is an amino acid or a polypeptide, or $R^2$ represents $—R^6—R^7$, wherein $R^6$ represents an amino acid or a polypeptide, and $R^7$ represents a hydrogen atom (H), $—NH_2$, substituted or unsubstituted $C_1$-$C_5$ alkyl, substituted or unsubstituted $C_5$-$C_{16}$ aryl, substituted or unsubstituted $C_5$-$C_{16}$ heteroaryl, a nucleic acid, or PEG, wherein in this step, the carboxy group of the amino acid or the polypeptide represented by $R^2$ in the linker binds to the resin;

(b) bonding the linker bonded to the resin to the physiologically active substance, wherein the linker binds to the physiologically active substance through an ester bond or a thioester bond formed with the carboxy group of the physiologically active substance by the elimination of the leaving group in the oxygen atom (O) or the sulfur atom (S); and (c) adding a sugar chain to a side chain of the amino acid or the polypeptide represented by $R^2$ in the linker.

In an alternative aspect, the present invention provides a compound or a salt thereof obtainable by the aforementioned method for producing a compound comprising a glycosylated linker moiety and a physiologically active substance moiety, or a salt thereof.

One or any combination of two or more of the features of the present invention mentioned above is also included in the scope of the method for producing the compound of the present invention or the salt thereof, as a matter of course.

Advantageous Effects of Invention

The glycosylated linker according to the present invention has a sugar chain structural moiety having many hydroxy groups and high polarity and can therefore improve the water solubility of a physiologically active substance by binding to the physiologically active substance.

Moreover, the glycosylated linker according to the present invention can release the physiologically active substance bonded to the glycosylated linker under particular conditions (e.g., in vivo) independent of light or enzymatic cleavage.

The compound comprising a glycosylated linker moiety and a physiologically active substance moiety according to the present invention or the salt thereof has water solubility.

The sugar chain in the glycosylated linker moiety according to the present invention is advantageous because of having biodegradable properties.

The sugar chain in the glycosylated linker moiety according to the present invention is also advantageous to reduction in the antigenicity of a physiologically active substance.

BRIEF DESCRIPTION OF DRAWINGS

FIG. 1 Each of FIGS. 1A and 1B is a graph showing results of a hydrolysis test on a thioalkyl-type glycosylated linker-HER2(8-16) conjugate (compound 1) according to one embodiment of the present invention. This graph is the plot of the relative concentration of a starting material vs. incubation time.

FIG. 2 Each of FIGS. 2A and 2B is a graph showing results of a hydrolysis test on a thioaryl-type glycosylated linker-HER2(8-16) conjugate (compound 2) according to one embodiment of the present invention. This graph is the plot of the relative concentration of a starting material vs. incubation time.

FIG. 3 is a graph showing results of a hydrolysis test on a thioalkyl-type glycosylated linker-HER2(8-16) conjugate (compound 1) having a thioester bond, a thioaryl-type glycosylated linker-HER2(8-16) conjugate (compound 2) having a thioester bond, and a glycosylated linker-HER2(8-16) conjugate (compound 6) having an ester bond. This graph is the plot of the relative concentration of a starting material vs. incubation time.

FIG. 4 is a graph showing results of a hydrolysis test on a glycosylated (Cys (disialo)-type) linker-chemerin 9 conjugate (compound 8). This graph is the plot of the relative concentration of a starting material vs. incubation time.

DESCRIPTION OF EMBODIMENTS

In the present specification, the "glycosylated linker" refers to a linker that has a sugar chain as a carrier which can improve the water solubility of a physiologically active substance having at least one carboxy group by binding to the physiologically active substance. A feature of the glycosylated linker bonded to the physiologically active substance is to be hydrolyzed at a desired rate under particular conditions, for example, in vivo. This hydrolysis allows the glycosylated linker to be eliminated from the physiologically active substance so that the physiologically active substance is released. The released physiologically active substance returns to its state before the addition of the glycosylated linker.

According to one embodiment, the glycosylated linker of the present invention is represented by the following formula (A).

In the above formula (A), X represents an oxygen atom (O) having a leaving group or a sulfur atom (S) having a leaving group.

In the present specification, the "oxygen atom (O) having a leaving group or sulfur atom (S) having a leaving group" refers to an atom that is present at the position X in the glycosylated linker represented by the formula (A): X—$R^1$—Y—$R^2$ and becomes capable of binding to the physiologically active substance by the elimination of the leaving group bonded to the atom. The bonding between the atom and the physiologically active substance is carried out via the carboxy group in the physiologically active substance.

In this context, the leaving group is not limited as long as the leaving group is eliminated when the oxygen atom (O) having the leaving group or the sulfur atom (S) having the leaving group binds to the carboxy group of the physiologically active substance. Examples thereof include a hydrogen atom and monovalent cations of lithium, sodium, potassium, rubidium, cesium, francium, and silver.

The glycosylated linker of the present invention binds to the physiologically active substance by forming an ester bond when X in the formula (A) is an oxygen atom (O) having a leaving group. Alternatively, the glycosylated linker of the present invention binds to the physiologically active substance by forming thioester when X in the formula (A) is a sulfur atom (S) having a leaving group.

In the formula (A), $R^1$ is substituted or unsubstituted $C_1$-$C_5$ alkyl, substituted or unsubstituted $C_5$-$C_{16}$ aryl, substituted or unsubstituted $C_5$-$C_{16}$ heteroaryl, substituted or unsubstituted $C_2$-$C_5$ alkenyl, or substituted or unsubstituted $C_2$-$C_5$ alkynyl, or $R^1$ represents -$R^3$—$R^3$—, —$R^4$—$R^5$—, or —$R^3$—$R^4$—$R^5$—. In this context, $R^3$ and $R^5$ each represent substituted or unsubstituted $C_1$-$C_5$ alkyl, substituted or unsubstituted $C_2$-$C_5$ alkenyl, or substituted or unsubstituted $C_2$-$C_5$ alkynyl. $R^4$ represents substituted or unsubstituted $C_5$-$C_{16}$ aryl, substituted or unsubstituted $C_5$-$C_{16}$ heteroaryl, or a sulfur atom (S).

In the present specification, the "substituted or unsubstituted $C_1$-$C_5$ alkyl" includes linear or branched alkyl. Examples of the "$C_1$-$C_5$ alkyl" can include, but are not limited to, methyl, ethyl, n-propyl, n-butyl, n-pentyl, isopropyl, isobutyl, sec-butyl, tert-butyl, isopentyl, neopentyl, and tert-pentyl. These "$C_1$-$C_5$ alkyl" groups can be each independently substituted by one or more "substituents". Examples of the "substituents" can include a $C_1$-$C_4$ alkoxy group (e.g., methoxy, ethoxy, propoxy, and butoxy), an amino group, a hydroxy group, a thiol group, a carboxy group, a nitro group, a mesyl group, a tosyl group, and a halogen atom (e.g., fluorine, chlorine, bromine, and iodine).

In the present invention, examples of the "substituted or unsubstituted $C_5$-$C_{16}$ aryl" can include, but are not limited to, phenyl, biphenyl, naphthyl, anthranyl, phenanthryl, anthryl, o-tolyl, m-tolyl, p-tolyl, xylyl, ethylphenyl, and benzyl.

The "substituted or unsubstituted $C_5$-$C_{16}$ aryl" is not limited to those listed above and includes "$C_5$-$C_{16}$ aryl" in which one or more hydrogen atoms are each independently replaced by "substituents". Examples of the "substituents" can include a $C_1$-$C_4$ alkyl group, a $C_1$-$C_4$ alkoxy group (e.g., methoxy, ethoxy, propoxy, and butoxy), an amino group, a hydroxy group, a thiol group, a carboxy group, a nitro group, a mesyl group, a tosyl group, a halogen atom (e.g., fluorine, chlorine, bromine, and iodine), a $C_1$-$C_4$ alkyl halide group (e.g., a methyl chloride group), a phenyl group, an o-tolyl group, a m-tolyl group, a p-tolyl group, a xylyl group, an ethylphenyl group, and a benzyl group.

In the present invention, examples of the "substituted or unsubstituted $C_5$-$C_{16}$ heteroaryl" can include, but are not limited to, a ring in which a ring structure-forming carbon atom is replaced by a nitrogen atom or an oxygen atom, and can more specifically include indole, quinoline, and chromene.

The "substituted or unsubstituted $C_5$-$C_{16}$ heteroaryl" is not limited to those listed above and includes "$C_5$-$C_{16}$ heteroaryl" in which one or more hydrogen atoms bonded to ring structure-forming carbon atoms are each independently replaced by "substituents". Examples of the "substituents" can include an alkyl group, an alkoxy group (e.g., methoxy, ethoxy, propoxy, and butoxy), a hydroxy group, a carboxy group, a nitro group, a mesyl group, a halogen atom (e.g., fluorine, chlorine, bromine, and iodine), and an alkyl halide group (e.g., a methyl chloride group).

In the present specification, the "substituted or unsubstituted $C_2$-$C_5$ alkenyl" includes linear or branched alkenyl. Examples of the "substituted or unsubstituted $C_2$-$C_5$ alkenyl" can include ethenyl, propenyl, and butenyl. The "substituted or unsubstituted $C_2$-$C_5$ alkenyl" is not limited to those listed above and also includes such "$C_2$-$C_5$ alkenyl" groups each independently substituted by one or more "substituents". Examples of the "substituents" can include a $C_1$-$C_4$ alkoxy group (e.g., methoxy, ethoxy, propoxy, and butoxy), an amino group, a hydroxy group, a thiol group, a carboxy group, a nitro group, a mesyl group, a tosyl group, and a halogen atom (e.g., fluorine, chlorine, bromine, and iodine).

In the present specification, the "substituted or unsubstituted $C_2$-$C_5$ alkynyl" includes linear or branched alkynyl. Examples of the "substituted or unsubstituted $C_2$-$C_5$ alkynyl" can include ethynyl, propynyl, and butynyl. The "substituted or unsubstituted $C_2$-$C_5$ alkynyl" is not limited to those listed above and includes such "$C_2$-$C_5$ alkynyl" groups each independently substituted by one or more "substituents". Examples of the "substituents" can include a $C_1$-$C_4$ alkoxy group (e.g., methoxy, ethoxy, propoxy, and butoxy), an amino group, a hydroxy group, a thiol group, a carboxy group, a nitro group, a mesyl group, a tosyl group, and a halogen atom (e.g., fluorine, chlorine, bromine, and iodine).

In the formula (A), Y may be present or absent in the formula (A). When Y is present in the formula (A), Y represents —CO— or —CONH— (provided that C is bonded to $R^1$ in the formula (A) and N is bonded to $R^2$ in the formula (A)).

In the formula (A), $R^2$ is a sugar chain, a glycosylated amino acid, or a glycosylated polypeptide, or $R^2$ represents —$R^6$—$R^7$. In this context, $R^6$ represents a sugar chain, a glycosylated amino acid, or a glycosylated polypeptide. $R^7$ represents a hydrogen atom (H), —$NH_2$, substituted or unsubstituted $C_1$-$C_5$ alkyl, substituted or unsubstituted $C_5$-$C_{16}$ aryl, substituted or unsubstituted $C_5$-$C_{16}$ heteroaryl, a nucleic acid, or PEG.

In the present specification, the "sugar chain" is a compound composed of one or more unit sugars (monosaccharides and/or derivatives thereof) linked. When two or more unit sugars are linked, the unit sugars are bonded to each other by dehydration condensation through a glycoside bond. Examples of such a sugar chain include, but are not limited to, a wide range of sugar chains such as monosaccharides and polysaccharides (glucose, galactose, mannose, fucose, xylose, N-acetylglucosamine, N-acetylgalactosamine, sialic acid, and complexes and derivatives thereof) contained in vivo as well as degraded polysaccharides and sugar chains degraded or induced from complex biomolecules including glycoproteins, proteoglycans, glycosaminoglycans, and glycolipids. The sugar chain may be linear or may be branched.

In the present specification, the "sugar chain" also includes derivatives of the sugar chain. Examples of the sugar chain derivatives include, but are not limited to, sugar chains constituted by sugars which are sugars having a carboxy group (e.g., aldonic acid which is carboxylic acid derived from oxidation at the C-1 position (e.g., D-gluconic acid oxidized from D-glucose) and uronic acid which is carboxylic acid derived from a terminal C atom (D-glucuronic acid oxidized from D-glucose)), sugars having an amino group or an amino group derivative (e.g., an acetylated amino group) (e.g., N-acetyl-D-glucosamine and N-acetyl-D-galactosamine), sugars having both an amino group and a carboxy group (e.g., N-acetylneuraminic acid (sialic acid) and N-acetylmuramic acid), deoxidized sugars (e.g., 2-deoxy-D-ribose), sulfated sugars containing a sulfuric acid group, and phosphorylated sugars containing a phosphoric acid group.

In the present invention, the sugar chain is preferably a sugar chain that improves the water solubility of a physiologically active substance when added as a glycosylated linker to the physiologically active substance.

In the present invention, the sugar chain is preferably a sugar chain that reduces the antigenicity of a physiologically active substance when added as a glycosylated linker to the physiologically active substance.

Such a sugar chain in the glycosylated linker of the present invention is not particularly limited and may be a sugar chain that is present as a glycoconjugate (glycopeptide (or glycoprotein), proteoglycan, or glycolipid, etc.) in vivo or may be a sugar chain that is not present as a glycoconjugate in vivo.

The sugar chain that is present as a glycoconjugate in vivo is preferred from the viewpoint of administering the glycosylated linker of the present invention to an organism. Examples of such a sugar chain include N-linked sugar chains and O-linked sugar chains, which are sugar chains bonded to peptides (or proteins) to form glycopeptides (or glycoproteins) in vivo. Preferably, a N-linked sugar chain is used. Examples of the N-linked sugar chain can include high-mannose-type, complex-type, and hybrid-type. A complex-type sugar chain is particularly preferred.

Preferred examples of the complex-type sugar chain used in the present invention include sugar chains represented by the following formula:

[Formula 3]

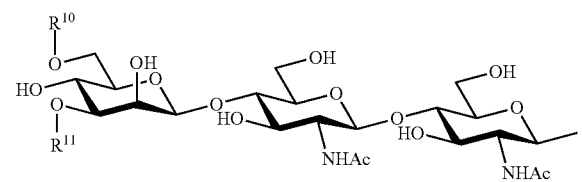

wherein $R^{10}$ and $R^{11}$ are the same or different and each represent

[Formula 4]

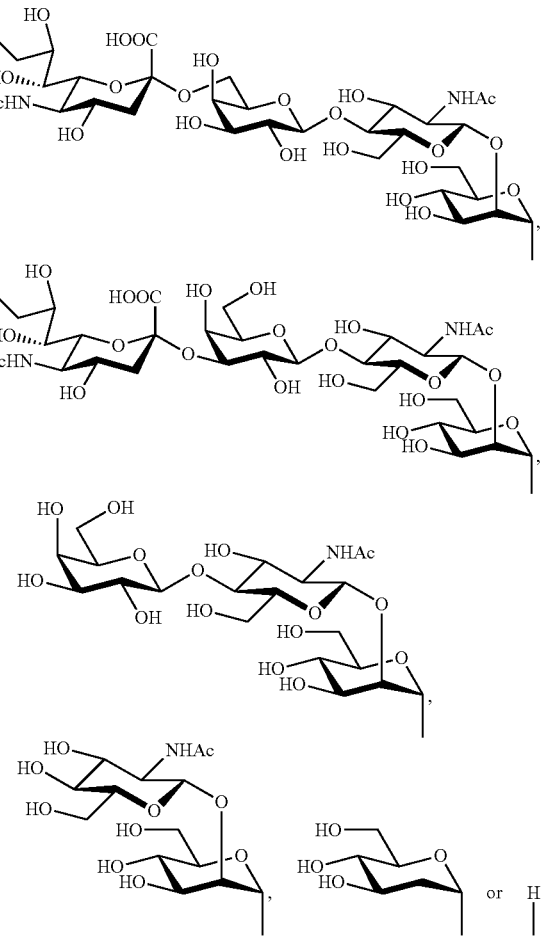

and Ac represents an acetyl group.

According to a preferred embodiment of the present invention, the sugar chain in the glycosylated linker of the present invention is a complex-type sugar chain. A feature of the complex-type sugar chain is to comprise two or more types of monosaccharides and to have a basic structure shown below and a lactosamine structure represented by Galβ1-4GlcNAc.

[Formula 5]

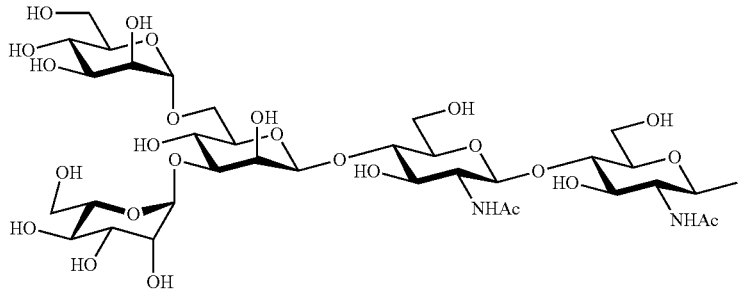

In the present invention, the complex-type sugar chain also includes a biantennary complex-type sugar chain. The biantennary complex-type sugar chain refers to a sugar chain in which one sugar chain composed of 0 to 3 sugars is bonded to each of two mannose residues at the ends of the basic structure. The biantennary complex-type sugar chain is preferably, for example, a disialo sugar chain shown below:

[Formula 6]

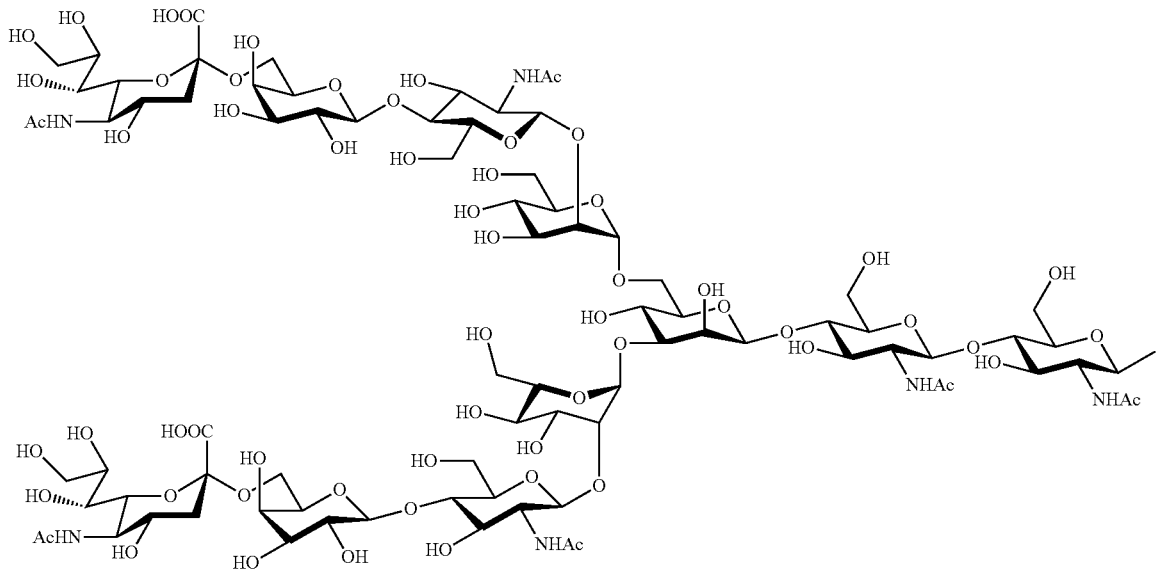

a monosialo sugar chain:
[Formula 7]
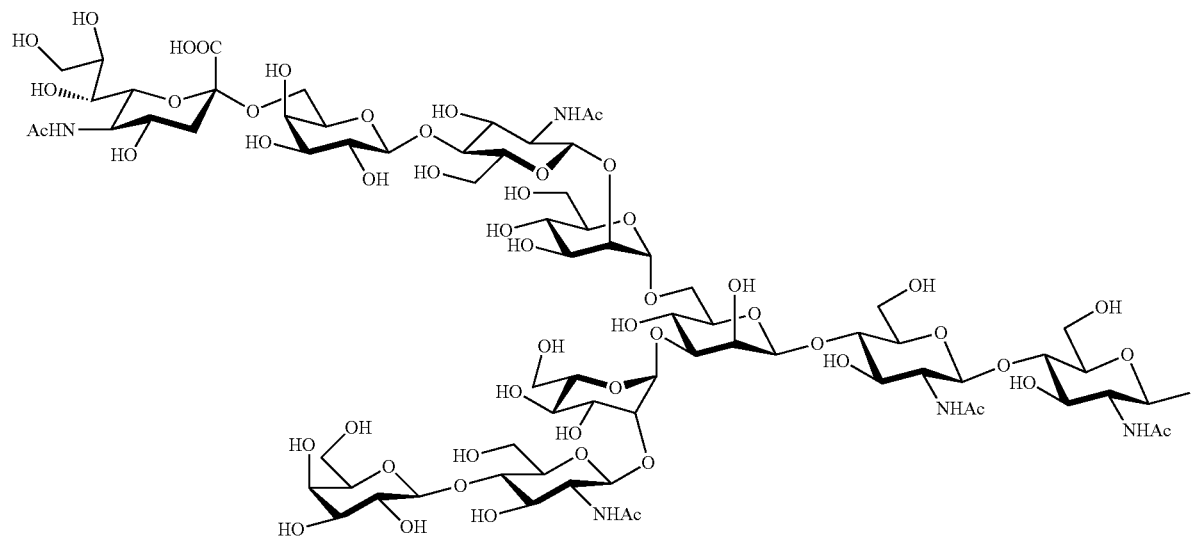
[Formula 8]
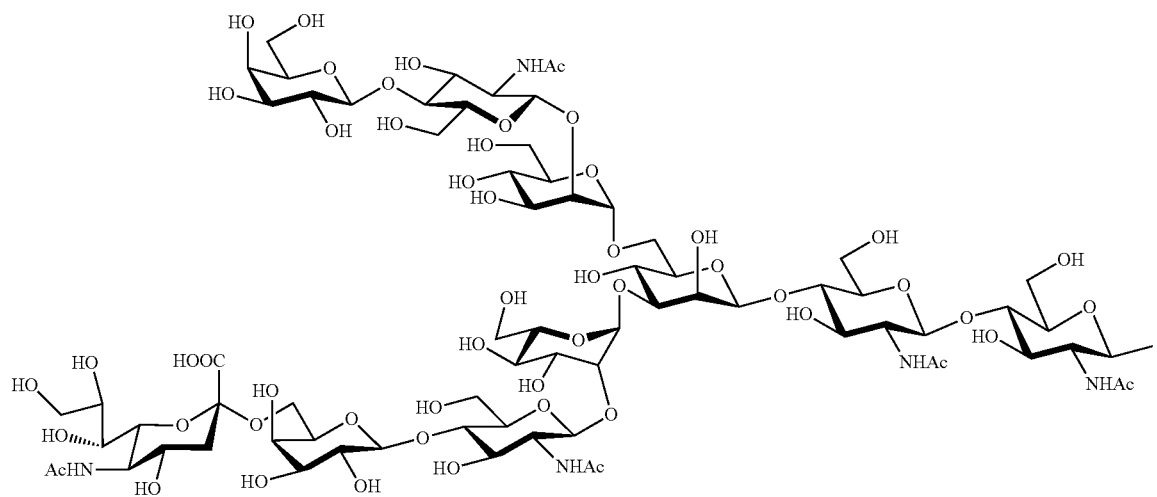

an asialo sugar chain:

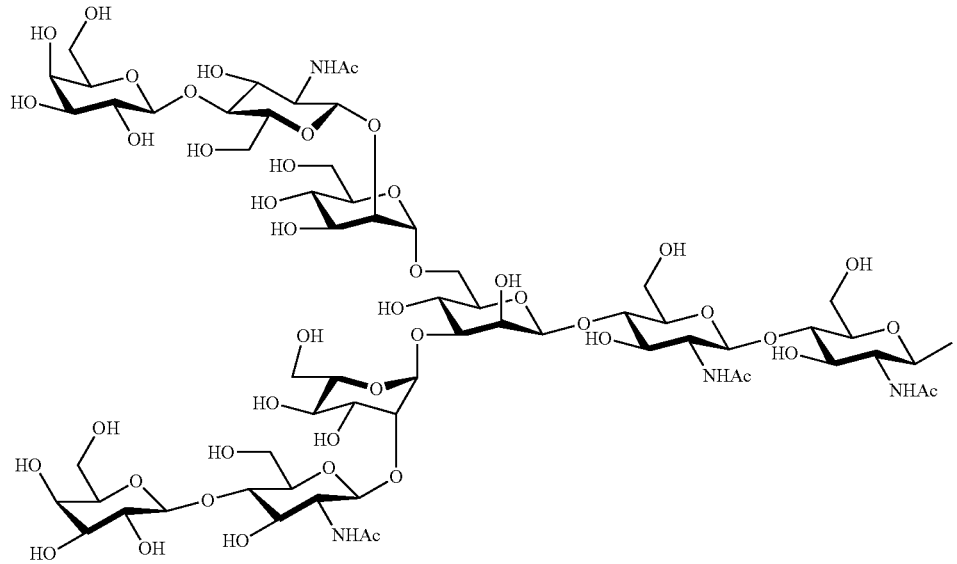

[Formula 9]

a di-GlcNAc sugar chain:

[Formula 10]

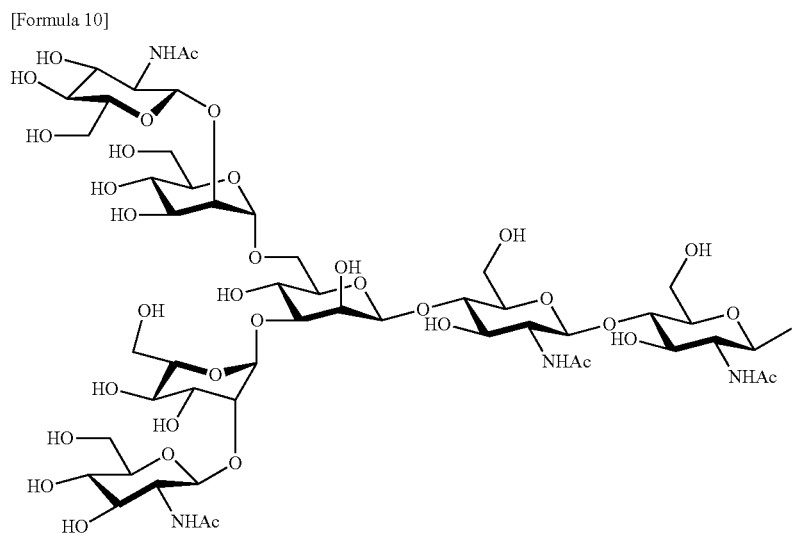

or a dimannose sugar chain:

[Formula 11]

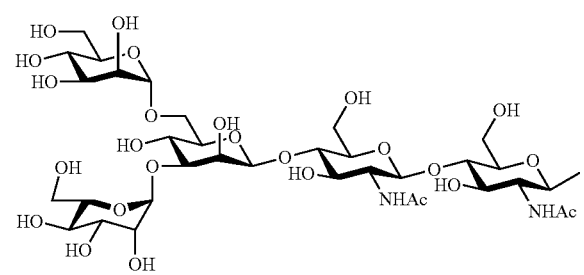

The biantennary complex-type sugar chain is more preferably a disialo sugar chain or an asialo sugar chain, most preferably a disialo sugar chain.

The complex-type sugar chain of the present invention also includes, in addition to the biantennary complex-type sugar chain (complex-type sugar chain having two branches), triantennary complex-type sugar chains (complex-type sugar chains having three branches) and tetraantennary complex-type sugar chains (complex-type sugar chains having four branches). Examples of the triantennary and tetraantennary complex-type sugar chains can include trisialo sugar chains represented by the following structural formulas:

[Formula 12]
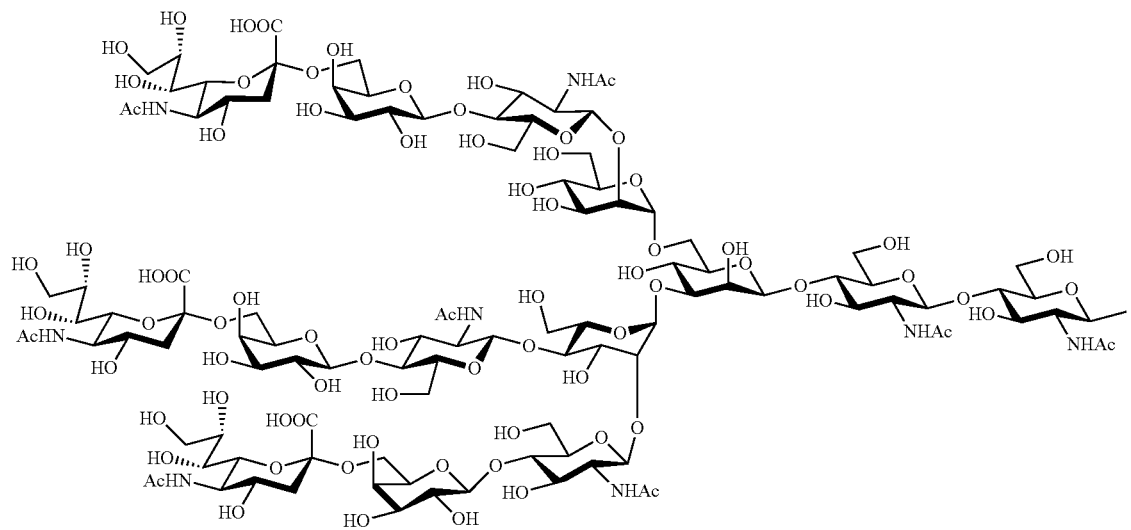
[Formula 13]
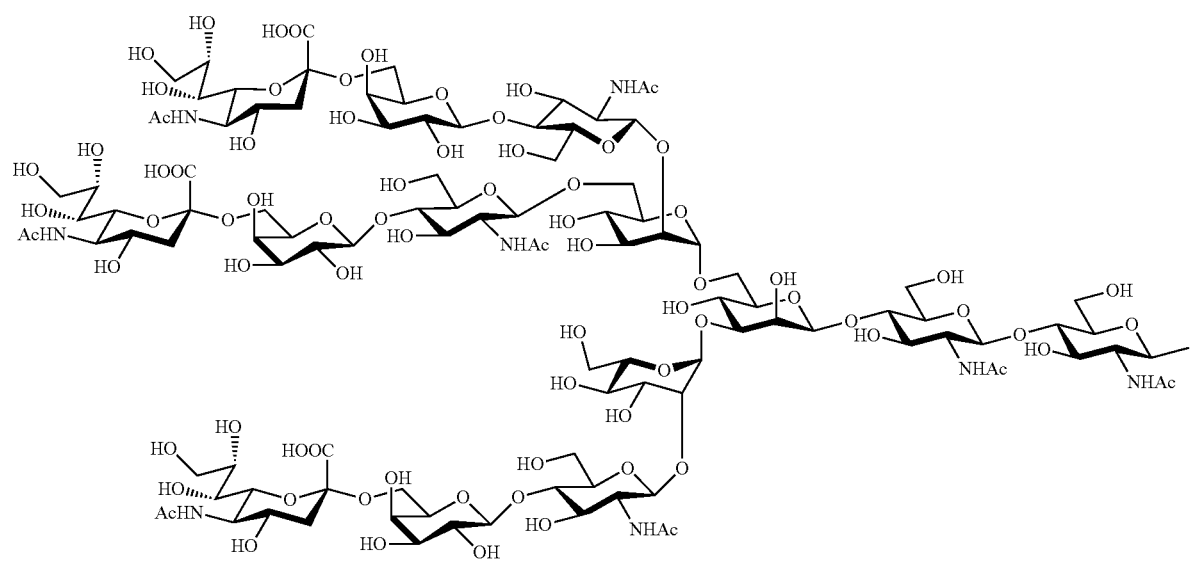

and tetrasialo sugar chains represented by the following structural formula:

[Formula 14]

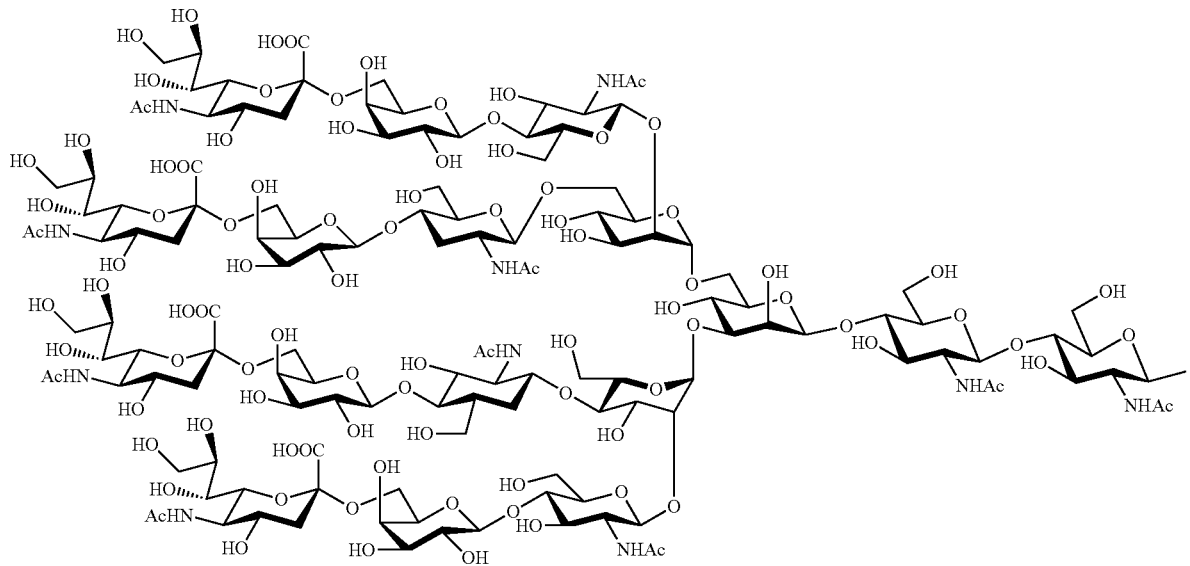

Further examples of the triantennary and tetraantennary complex-type sugar chains can include sugar chains derived from these trisialo sugar chains or tetrasialo sugar chains by the deletion of one or more sugar residues from the non-reducing end.

The complex-type sugar chain of the present invention further includes fucose-attached complex-type sugar chains. Examples of the fucose-attached complex-type sugar chains can include fucose-containing complex-type sugar chains represented by the following structural formulas:

[Formula 15]

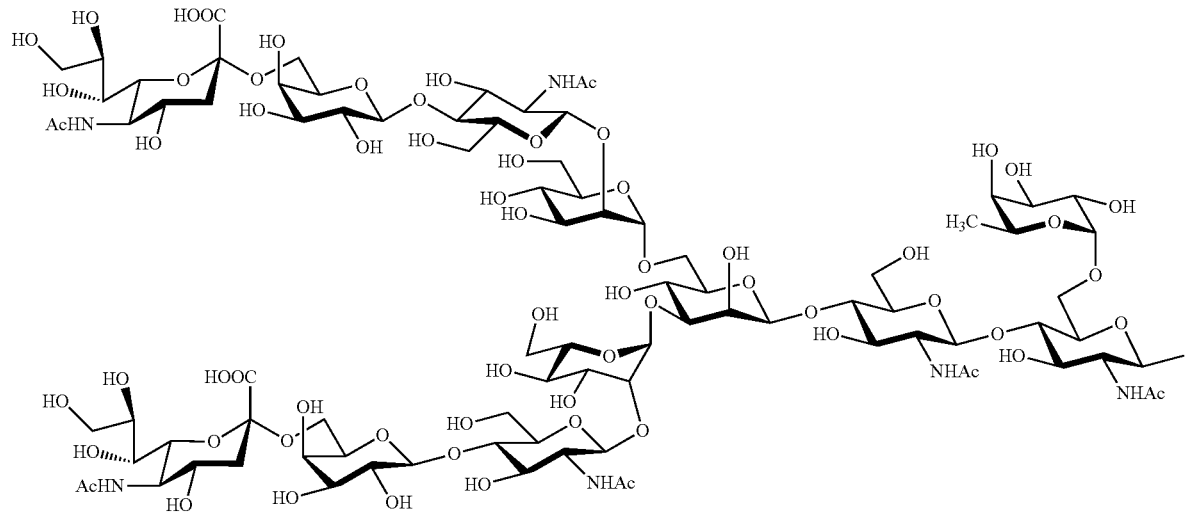

[Formula 16]
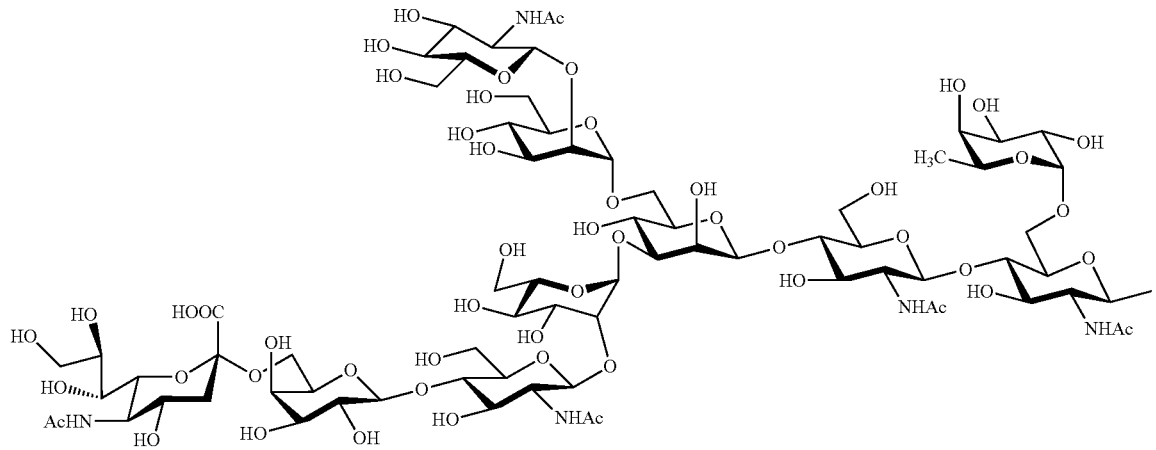
[Formula 17]
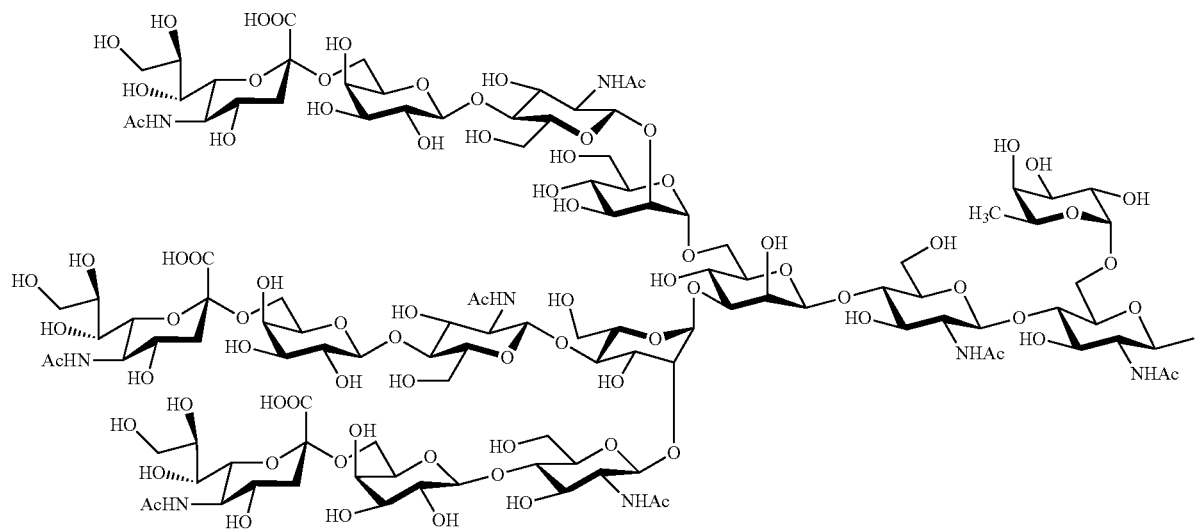
[Formula 18]
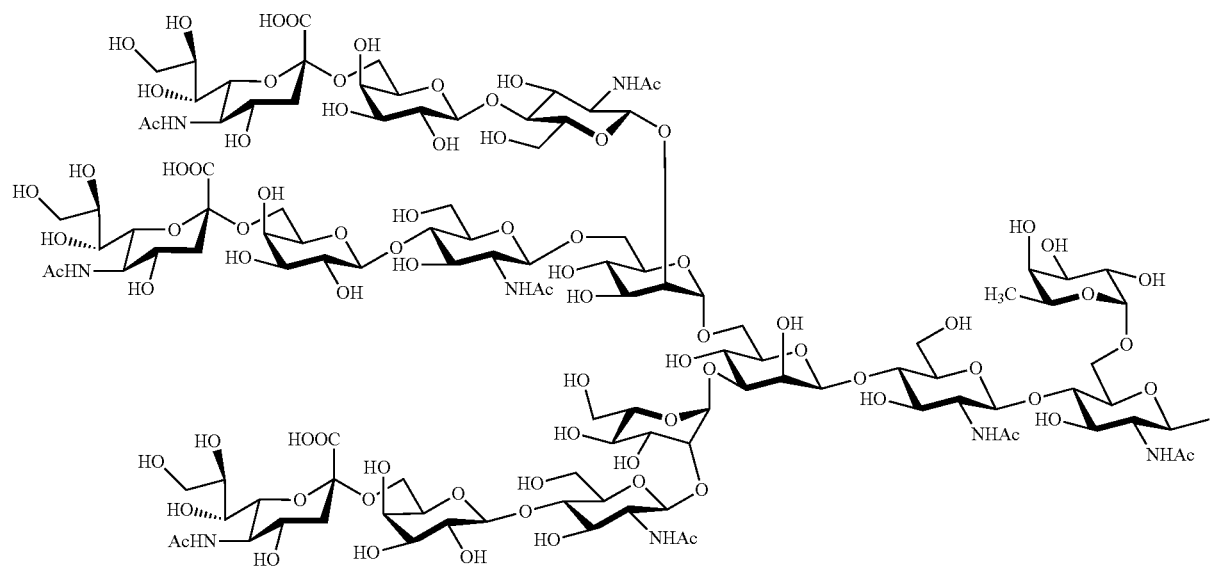

-continued

[Formula 19]

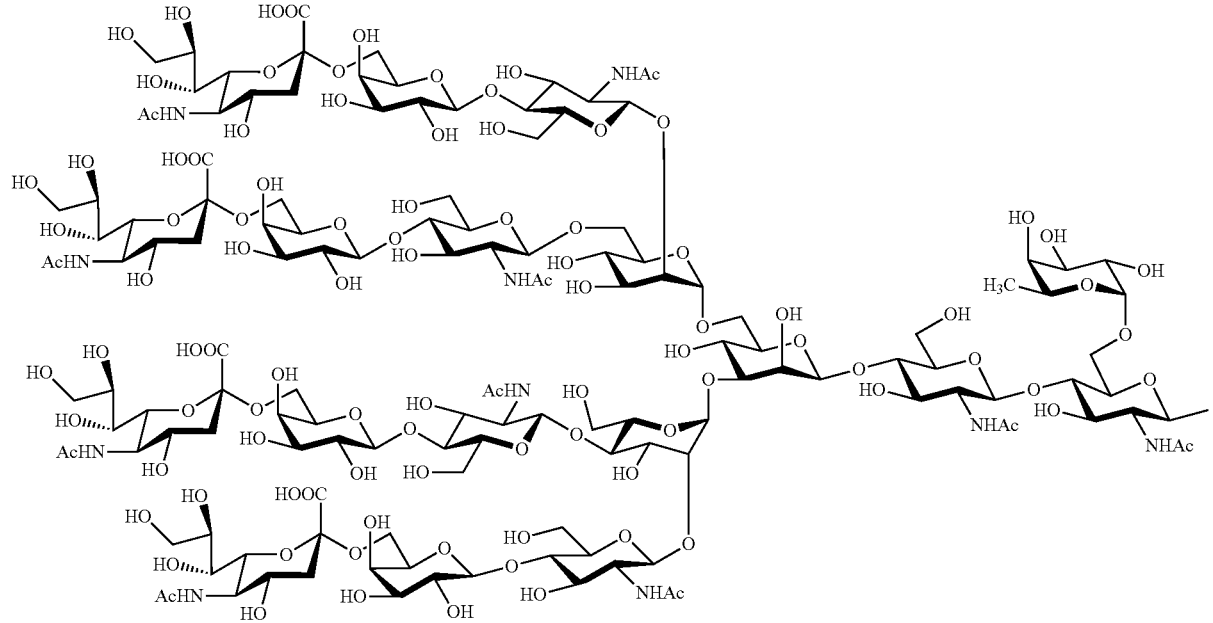

Further examples thereof can include sugar chains derived from these fucose-containing complex-type sugar chains by the deletion of one or more sugars from the non-reducing end.

In the present specification, the "biantennary complex-type sugar chain", the "disialo sugar chain", the "monosialo sugar chain", the "asialo sugar chain", the "di-GlcNAc sugar chain", the "dimannose sugar chain", the "triantennary complex-type sugar chain", the "tetraantennary complex-type sugar chain", and the "fucose-containing containing complex-type sugar chain" include, in addition to those shown in the above chemical formulas, sugar chains differing in binding pattern from the examples represented by the chemical formulas. Such a sugar chain is also preferably used as the sugar chain of the present invention. Examples of such a sugar chain include disialo sugar chains and monosialo sugar chains in which sialic acid and galactose are bonded through a (α2→3) bond.

The complex-type sugar chain of the present invention also includes sugar chains having a polylactosamine structure or a sialylpolylactosamine structure represented by the following formula:

[Formula 20]

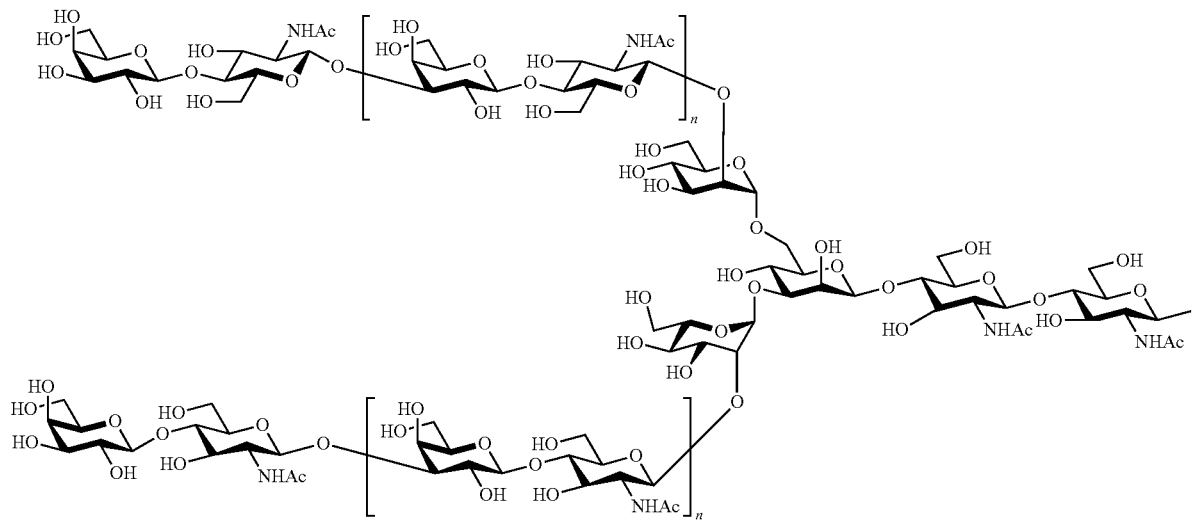

wherein n represents an integer of 2 to 3

[Formula 21]

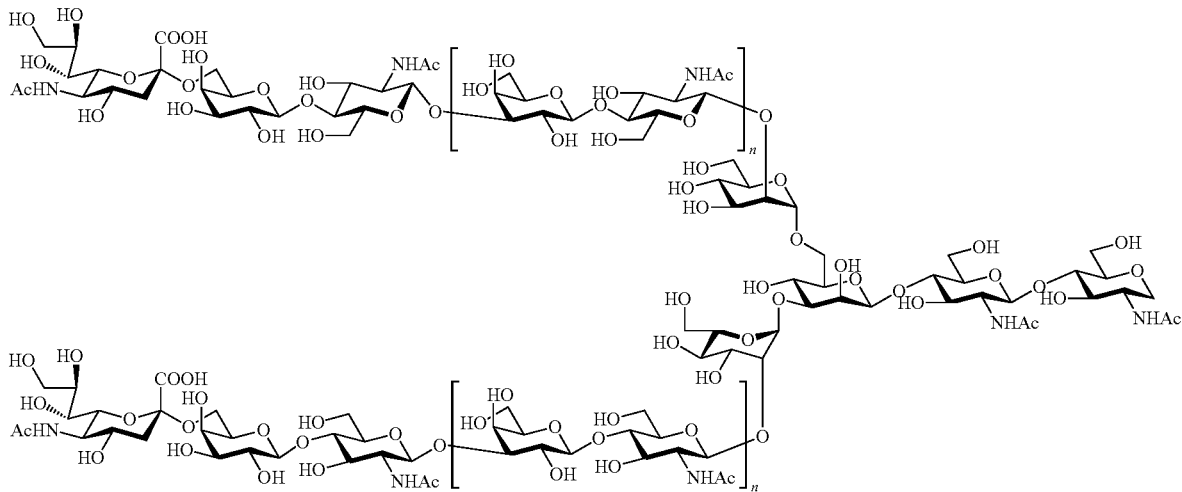

wherein n represents an integer of 2 to 3.

The high-mannose-type sugar chain used in the present invention is a sugar chain in which two or more mannose residues are further bonded to the basic structure of the complex-type sugar chain mentioned above. Since the high-mannose-type sugar chain is bulky, a peptide bonded to the high-mannose-type sugar chain may have higher stability in blood. The high-mannose-type sugar chain is preferably a sugar chain containing 5 to 9 mannose residues as found in mammals and may be a sugar chain containing a larger number of mannose residues as found in yeasts. Examples of the high-mannose-type sugar chain preferably used in the present invention can include high-mannose-5 (M-5):

[Formula 22]

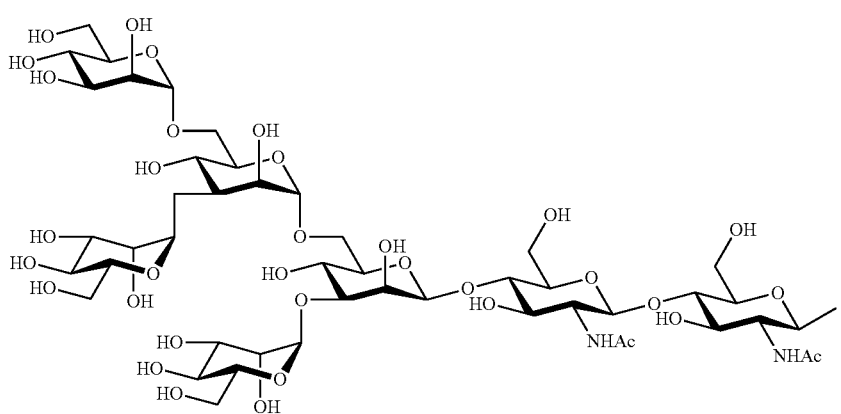

and high-mannose-9 (M-9):

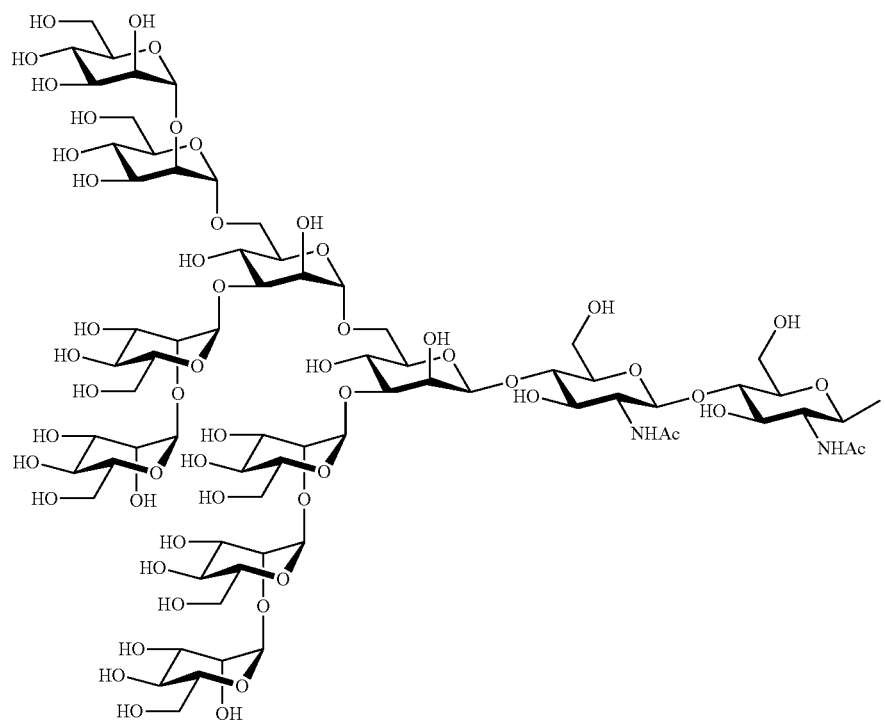

[Formula 23]

In the present invention, preferred examples of the sugar chain can also include sugar chains structurally identical (sugar chains identical in the types of constituent sugars and binding patterns thereof) to sugar chains that are bonded to proteins to form glycoproteins in human bodies (e.g., sugar chains described in "FEBS LETTERS Vol. 50, No. 3, February 1975"), and sugar chains derived from these sugar chains by the deletion of one or more sugars from the non-reducing end. Specific examples thereof can include sugar chains listed below.

[Formula 21]

1S2S-11NC, 1

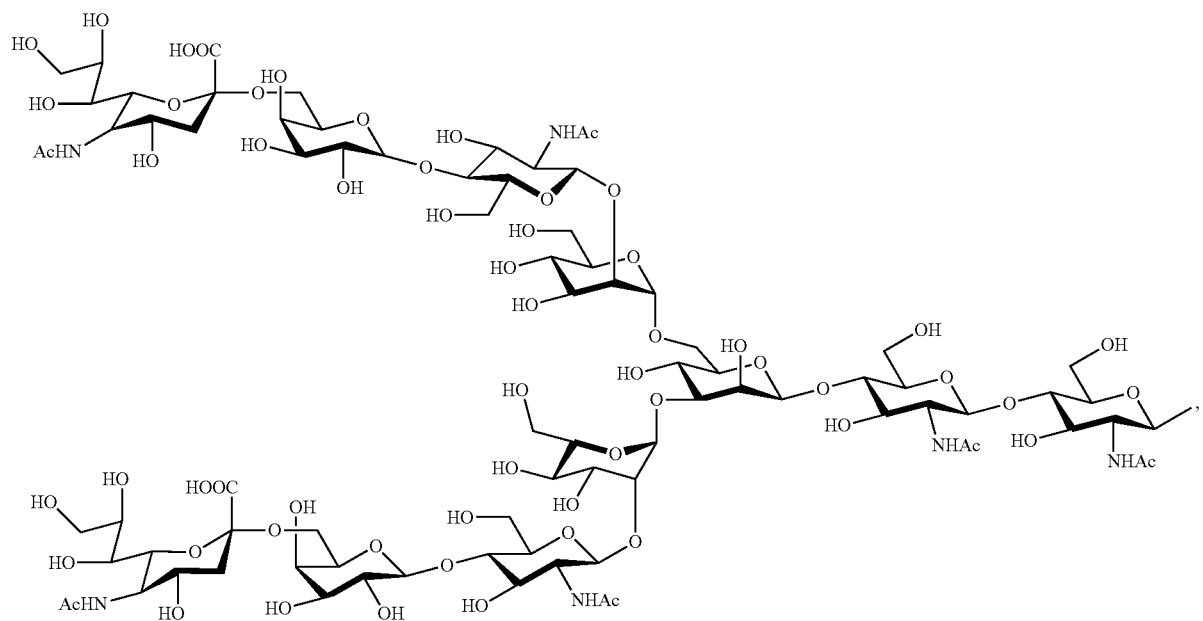

-continued
1S2G-10NC, 2
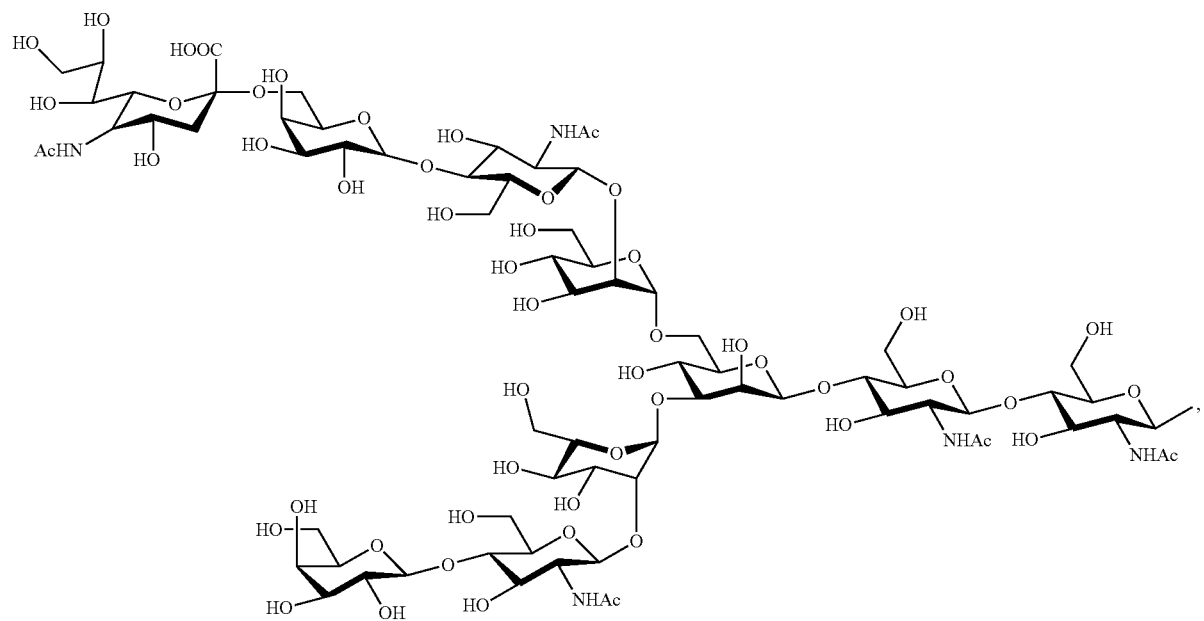
1S2GN-9NC, 3
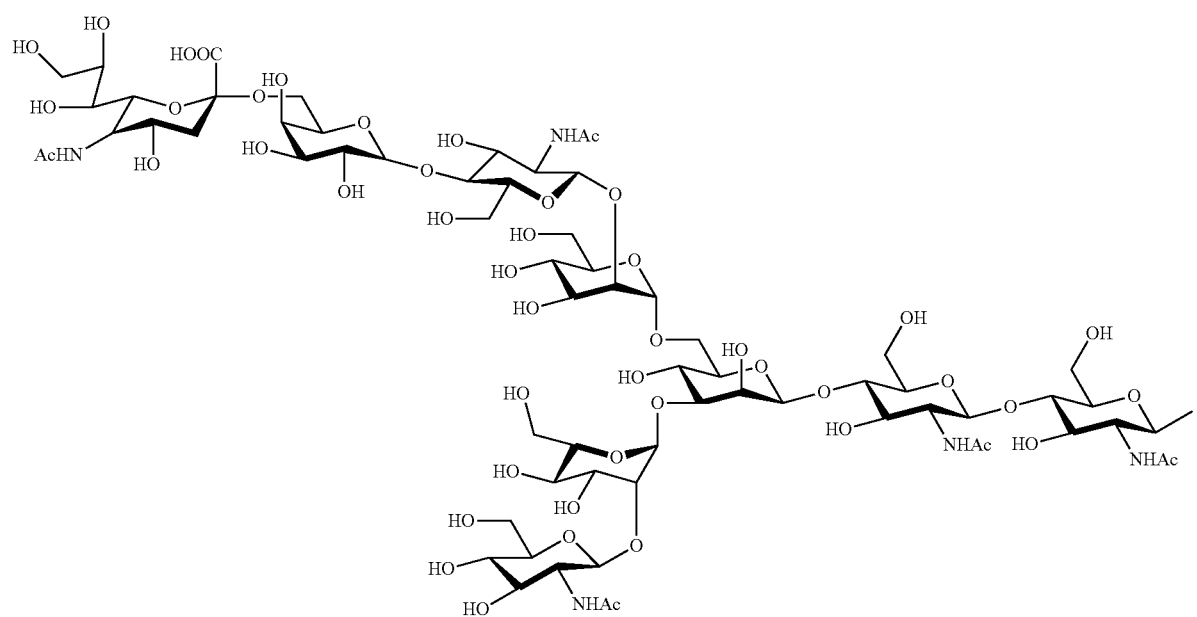

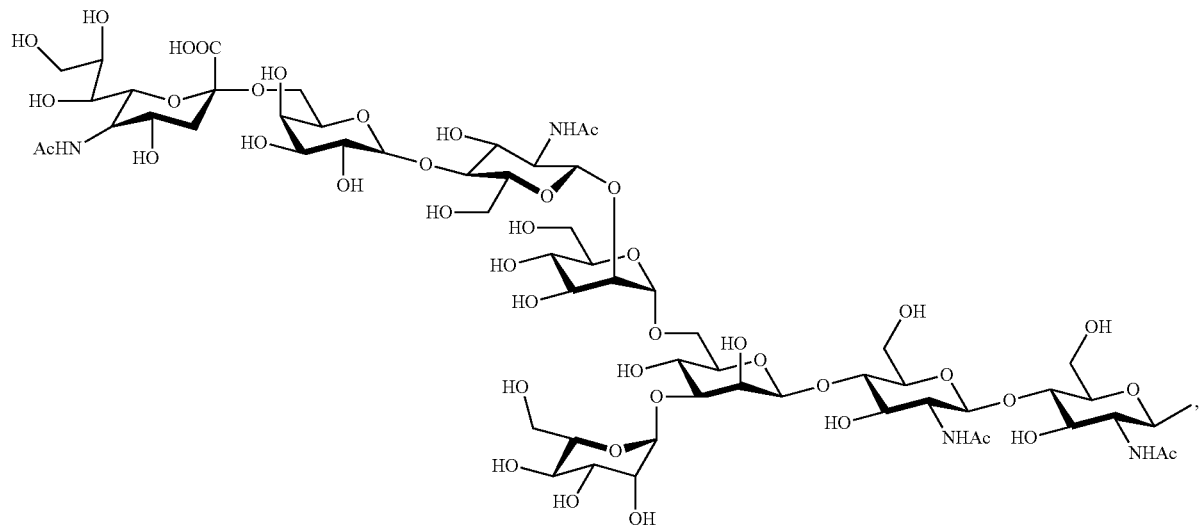
1S2M-8NC, 4
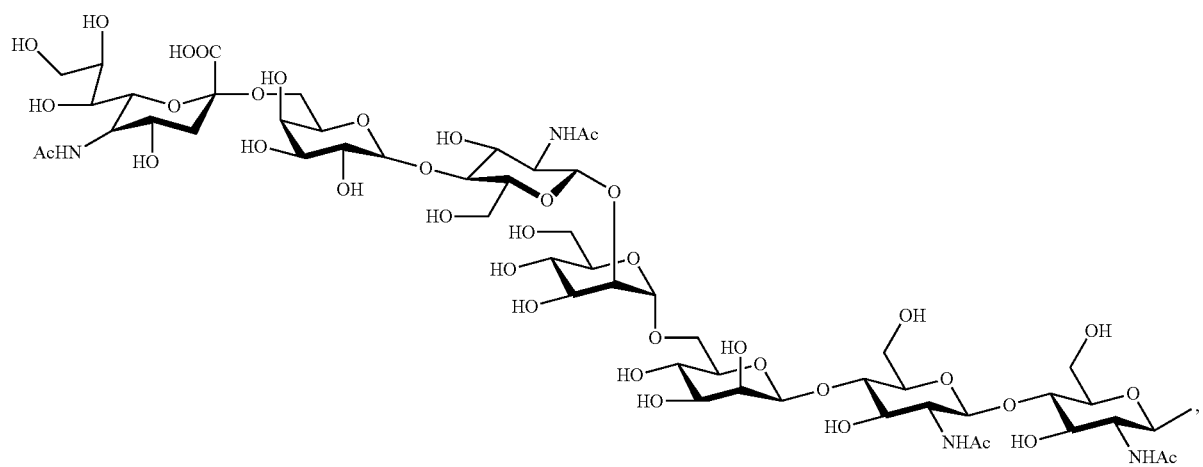
1S-7NC, 5
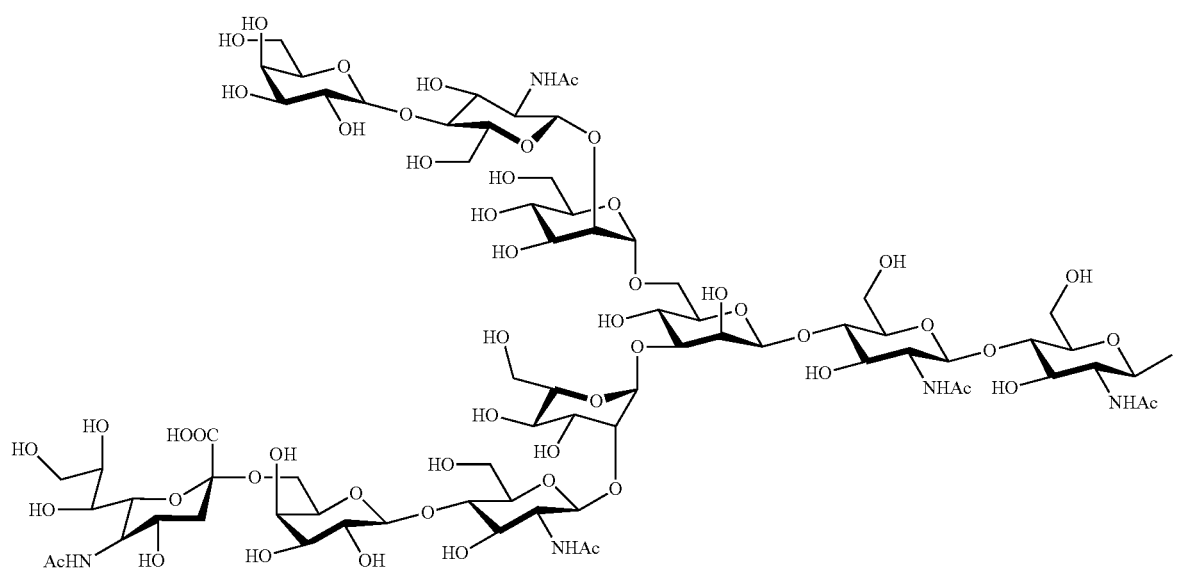
1G2S-10NC, 6

-continued
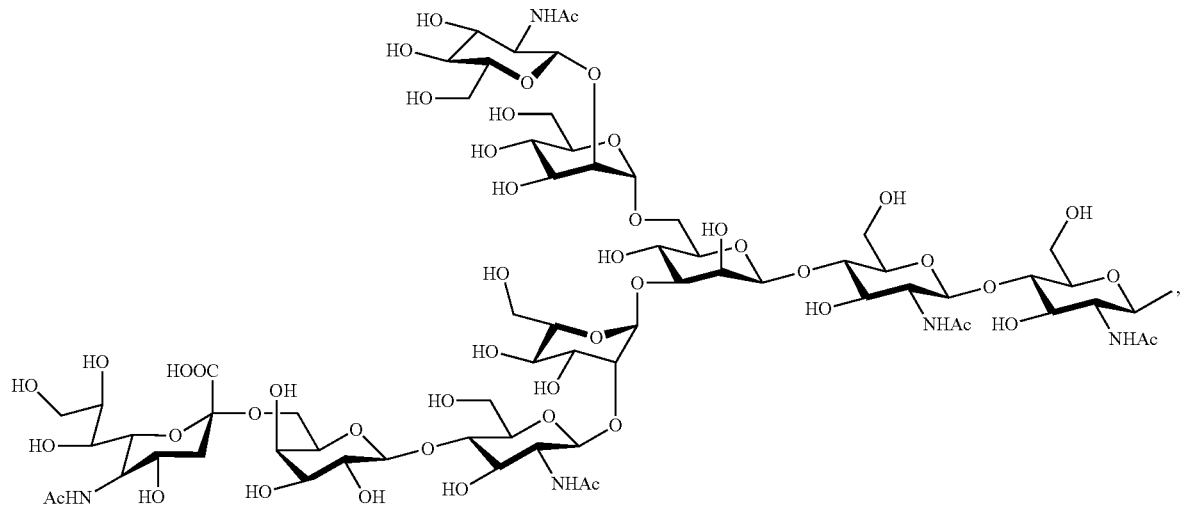
1GN2S-9NC, 7
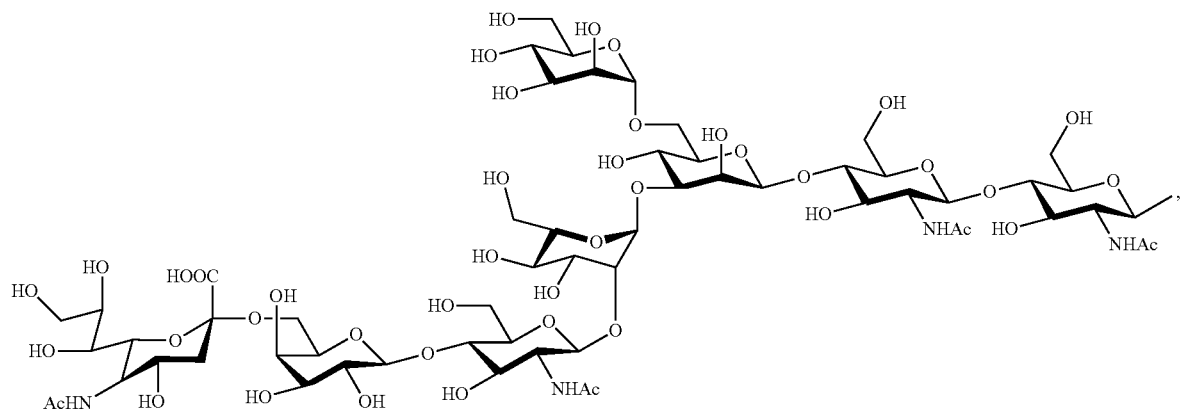
1M2S-8NC, 8
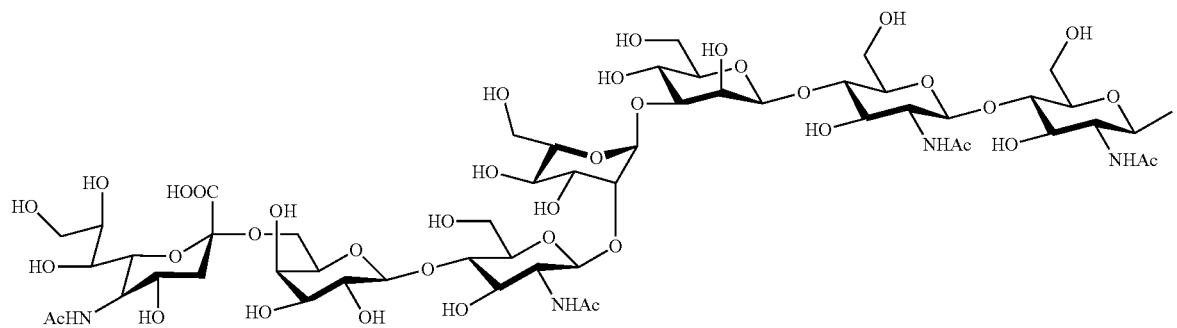
2S-NC, 9

-continued
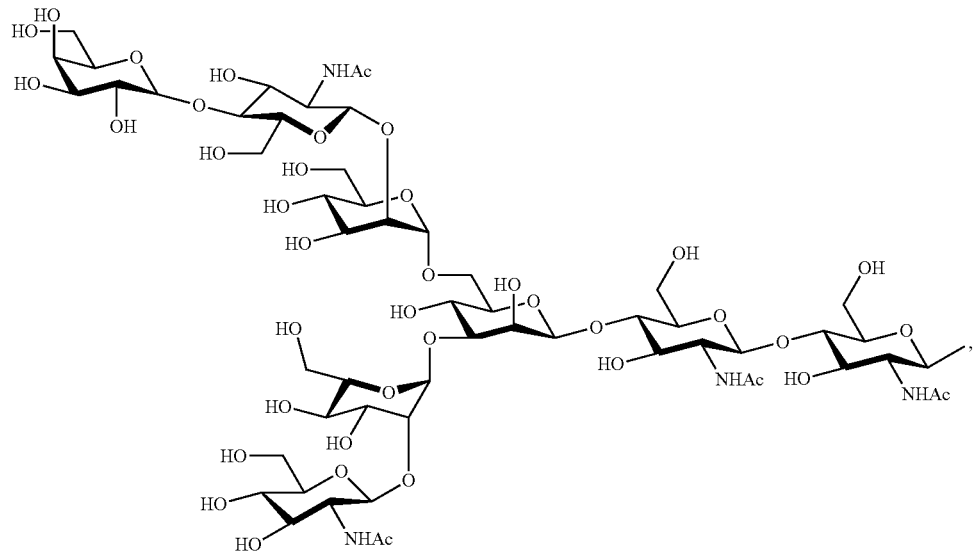
1G2GN-8NC, 10
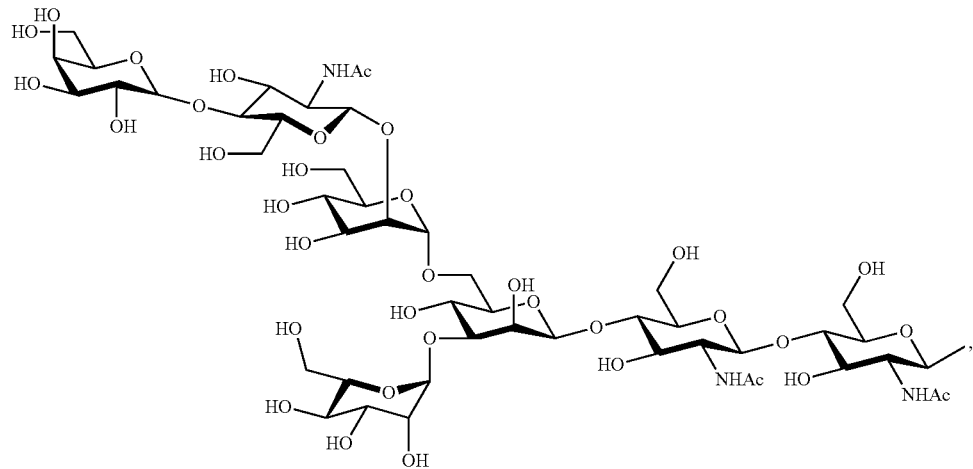
1G2M-7NC, 11
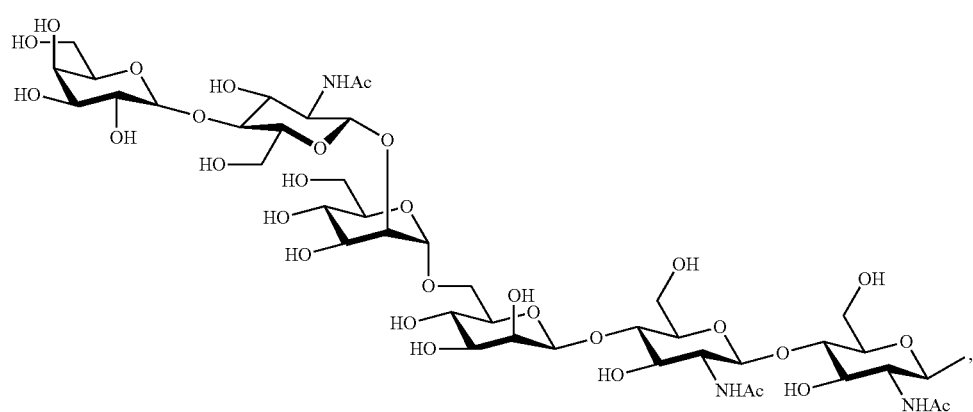
1G-6NC, 12

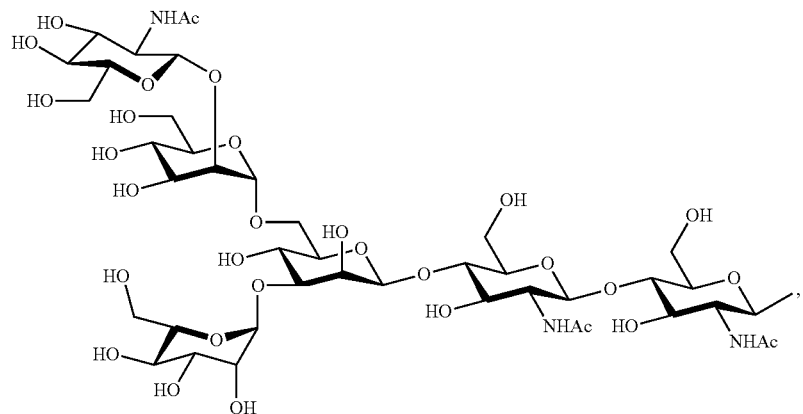
1GN2M-6NC, 13
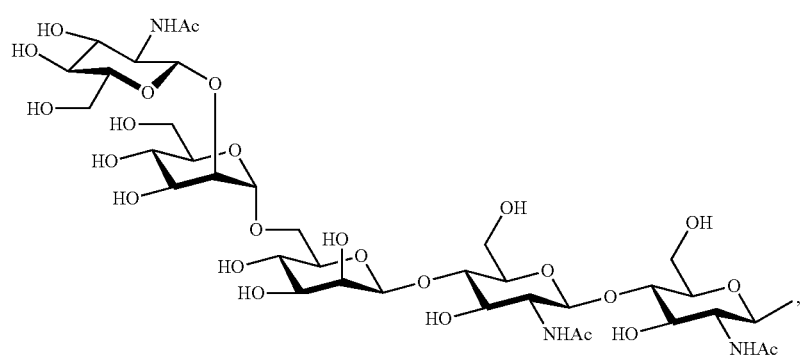
1G2-5NC, 14
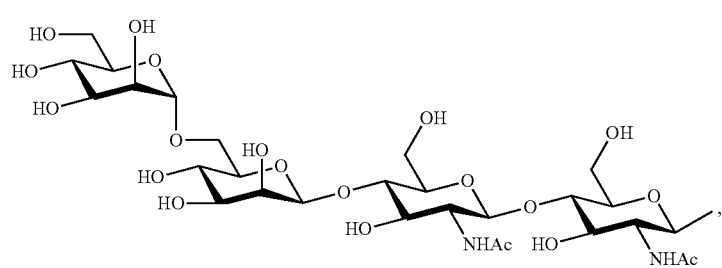
1M-4NC, 15
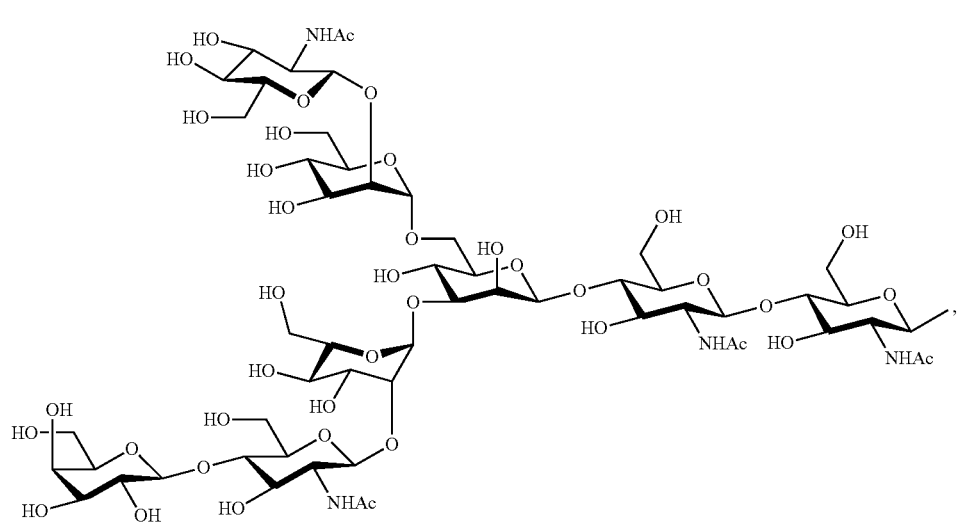
1GN2G-8NC, 16

-continued
1M2G-7NC, 17
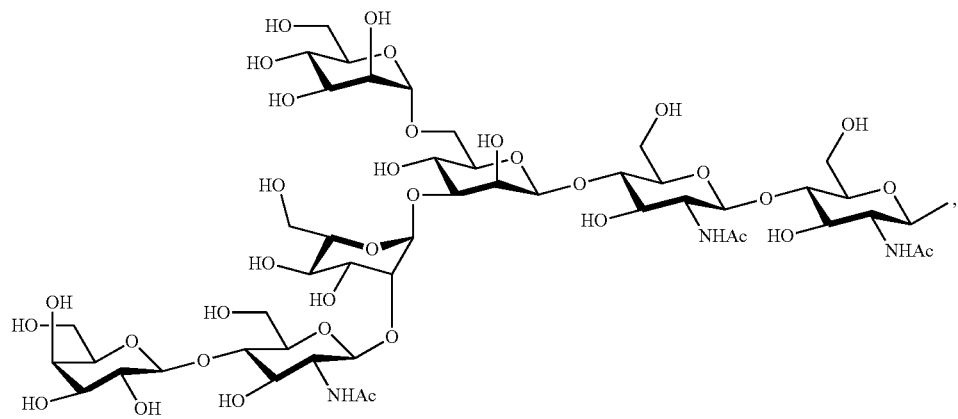
2G-6NC, 18
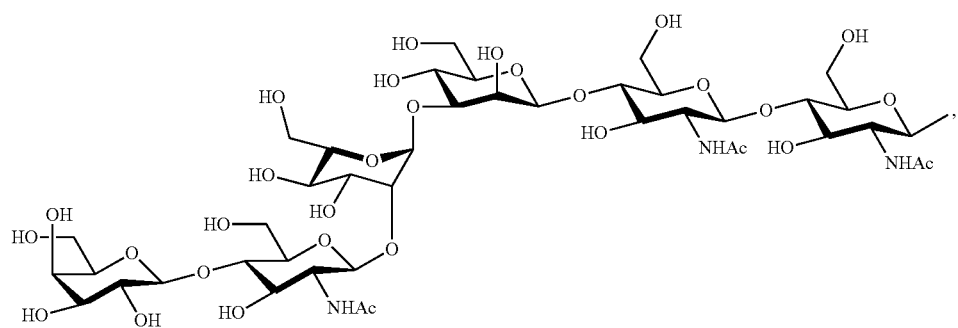
1M2GN-5NC, 19
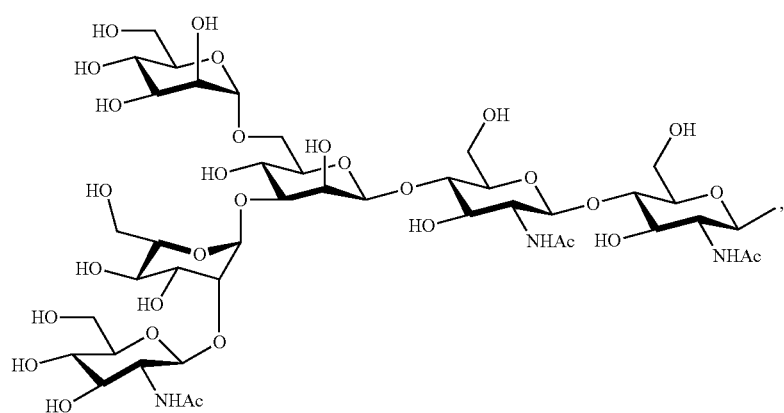
2GN-5NC, 20
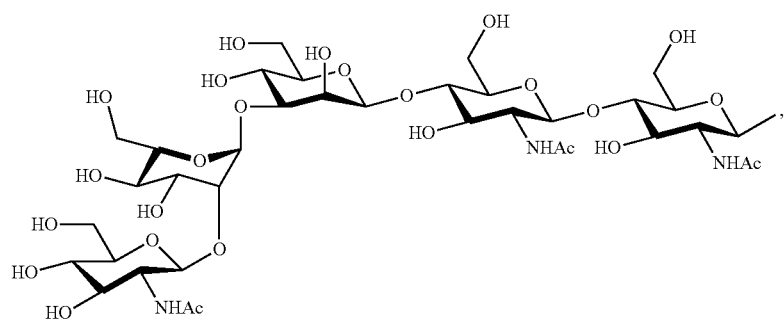

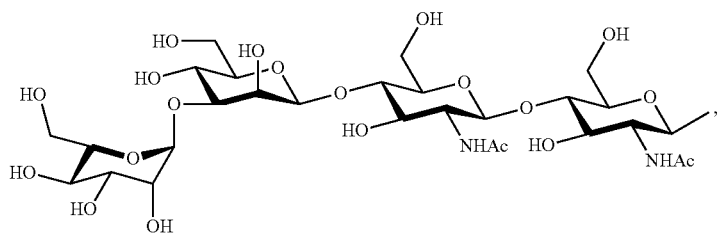
2M-4NC, 21
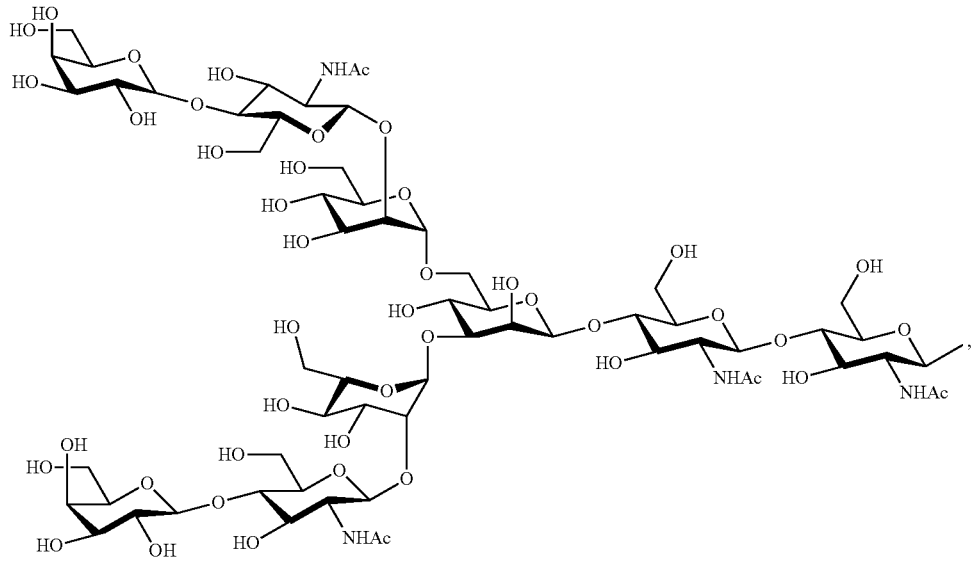
1G2G-9NC, 22
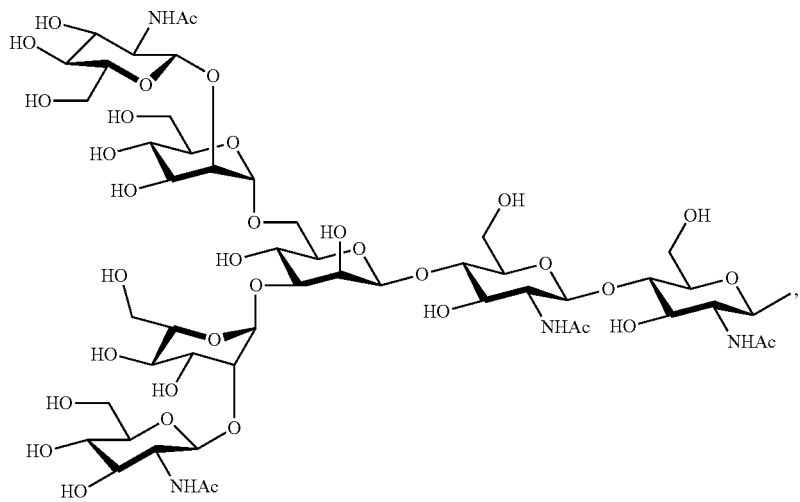
1GN2GN-7NC, 23
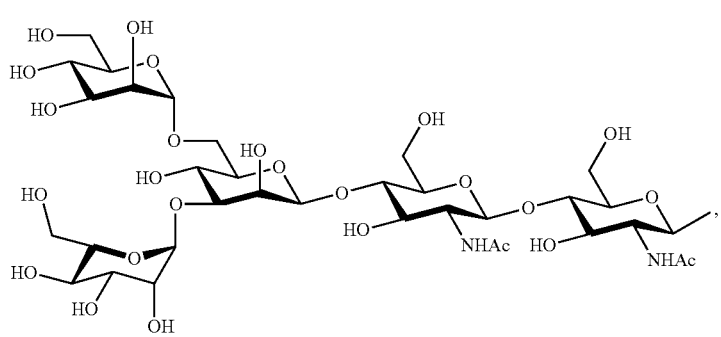
1M2M-5NC, 24

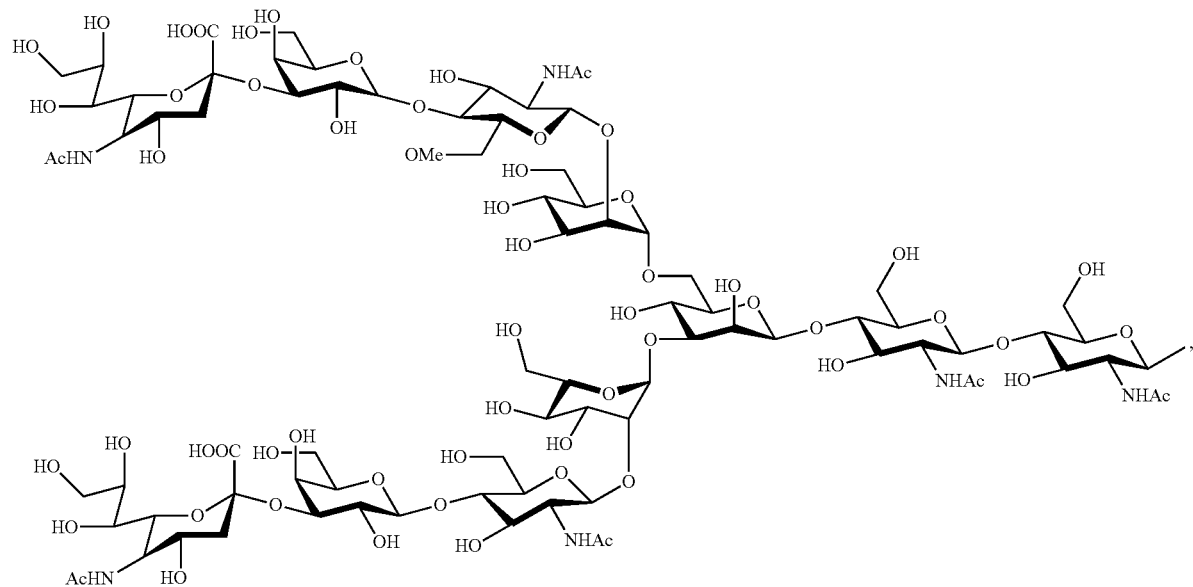
1S(3)2S(3)-11NC, 25
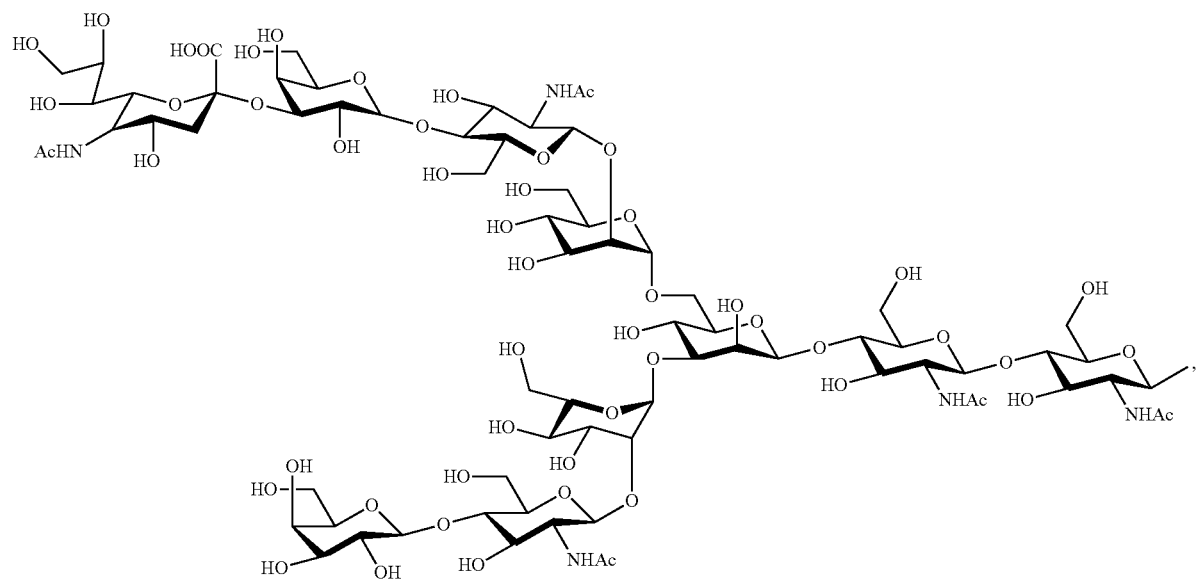
1S(3)2G-10NC, 26

-continued
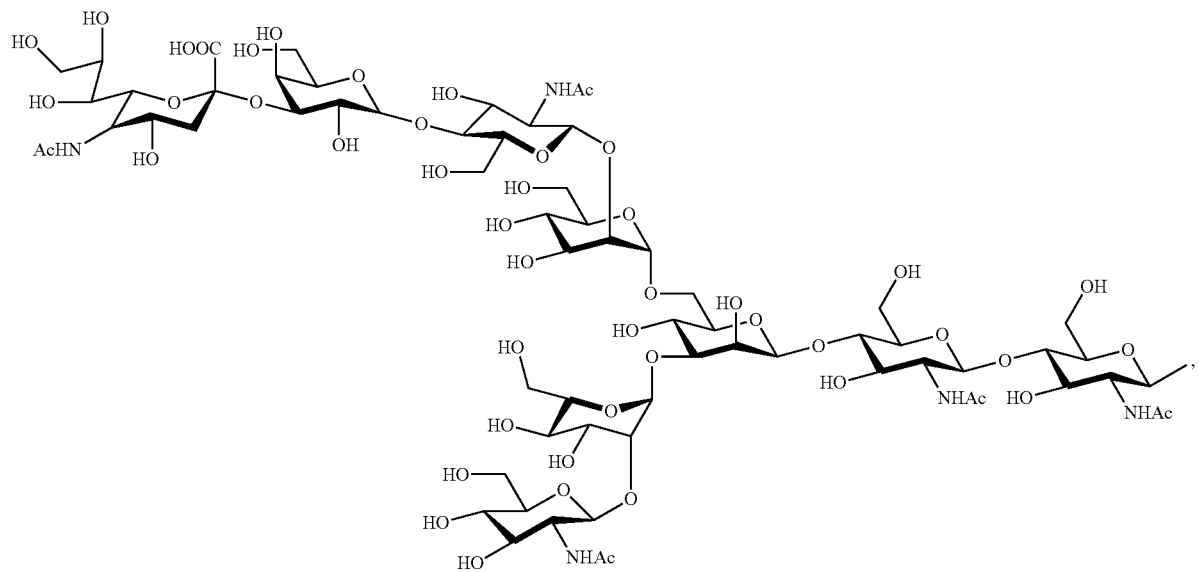
1S(3)2GN-9NC, 27
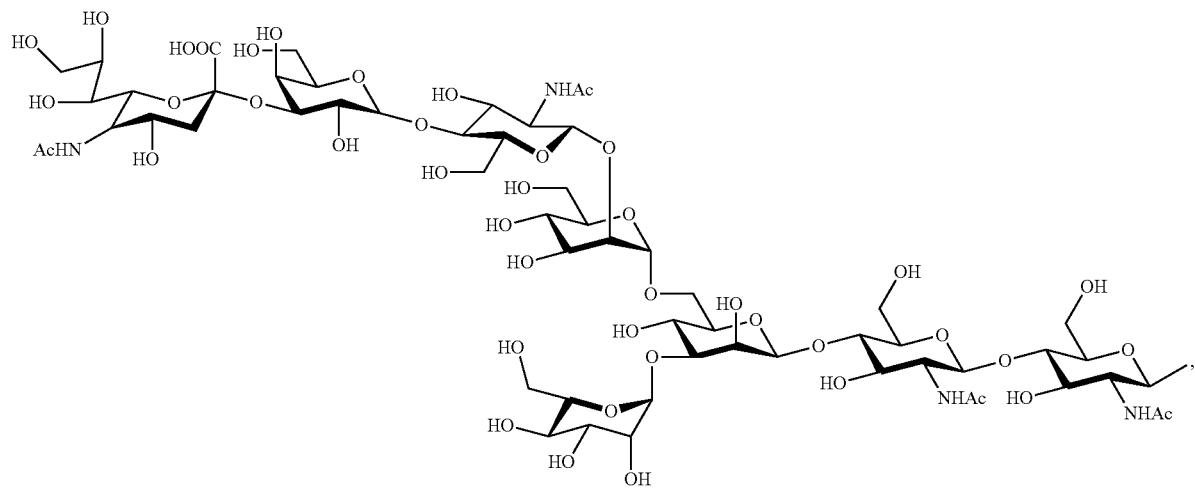
1S(3)2M-8NC, 28
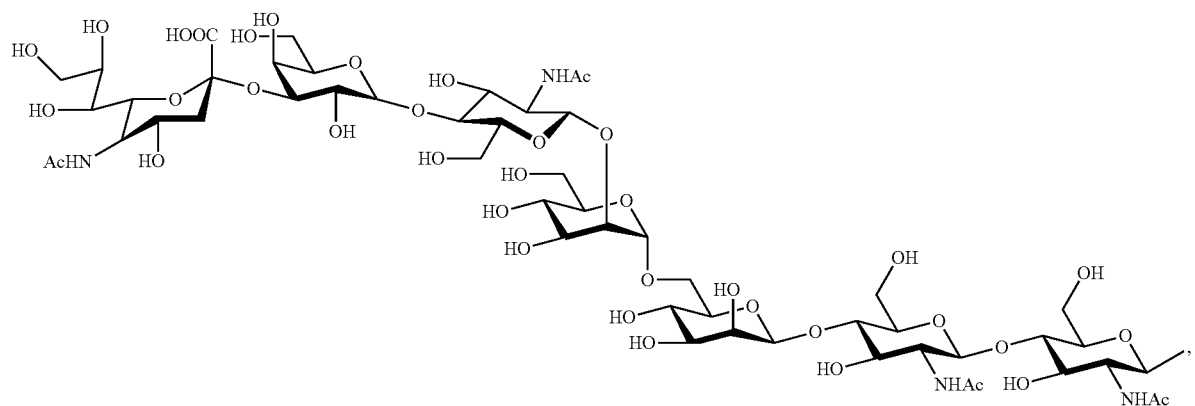
1S(3)-7NC, 29

-continued
1G2S(3)-10NC, 30
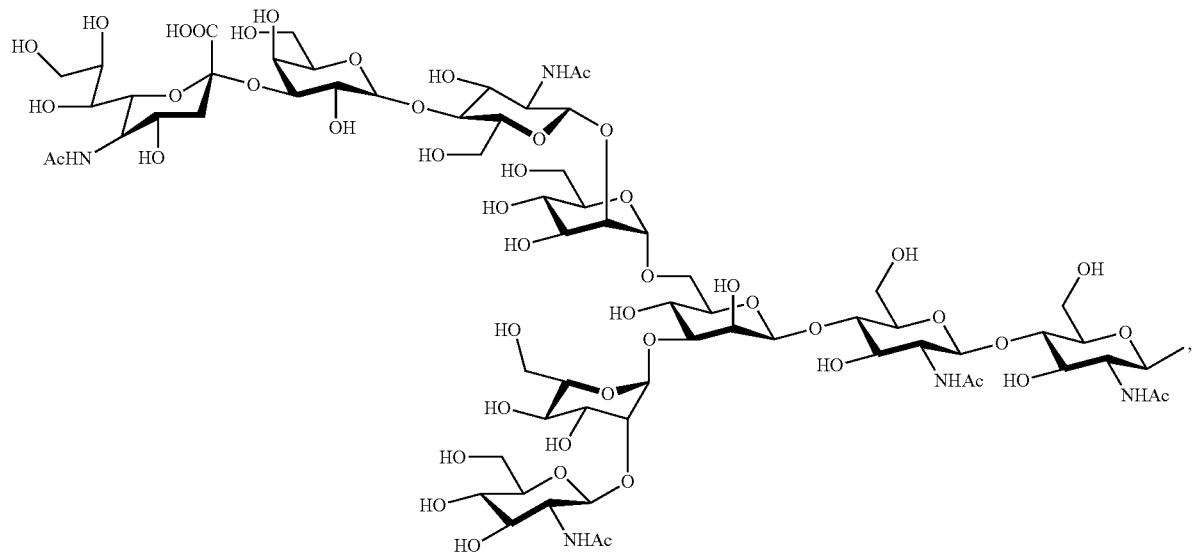
1GN2S(3)-9NC, 31
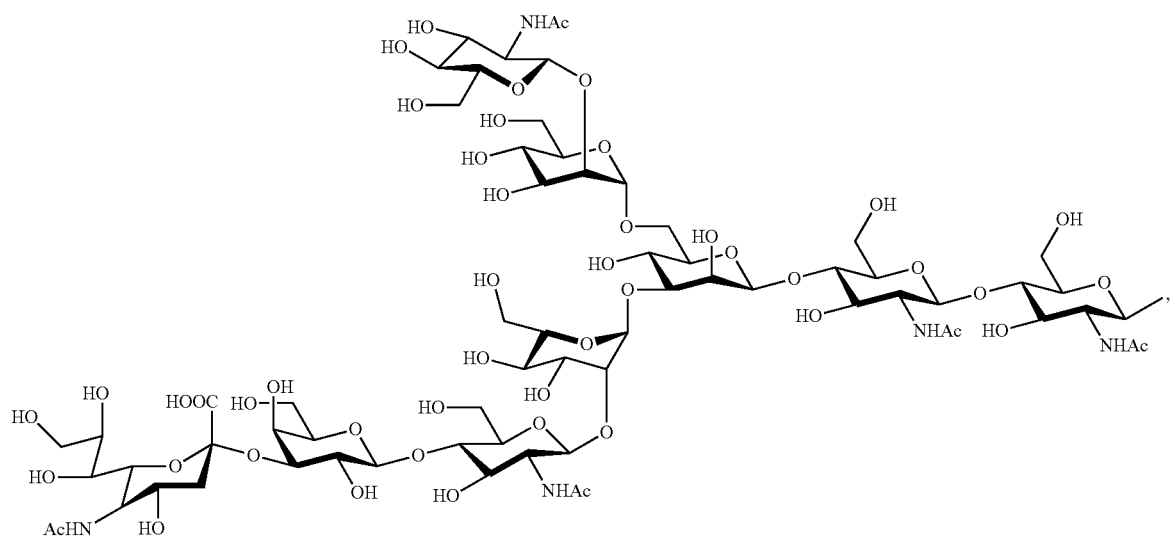
1M2S(3)-8NC, 32
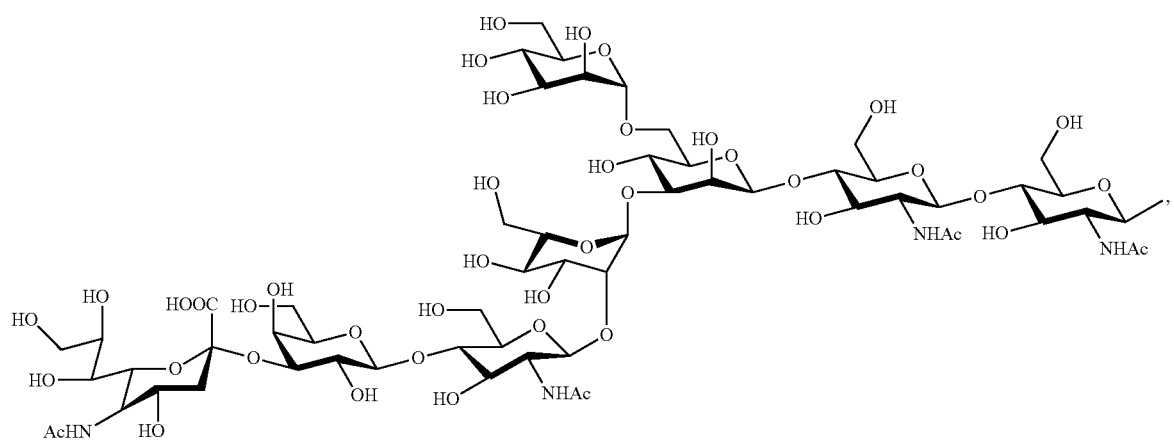

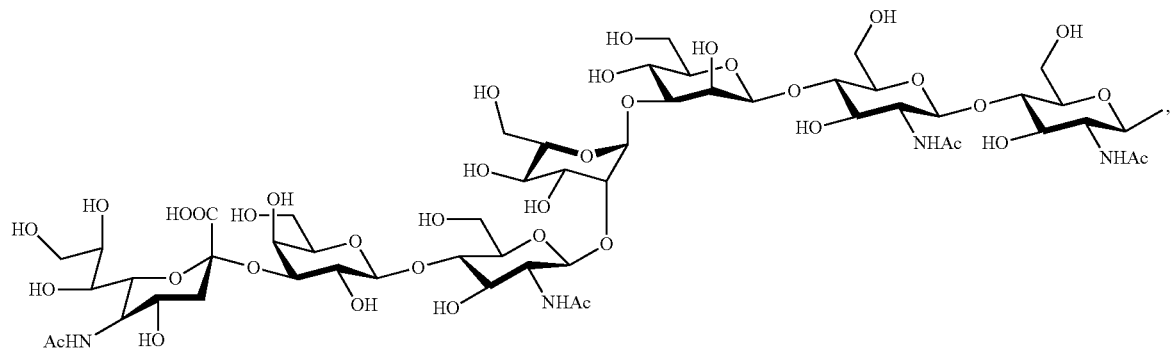
2S(3)-7NC-, 33
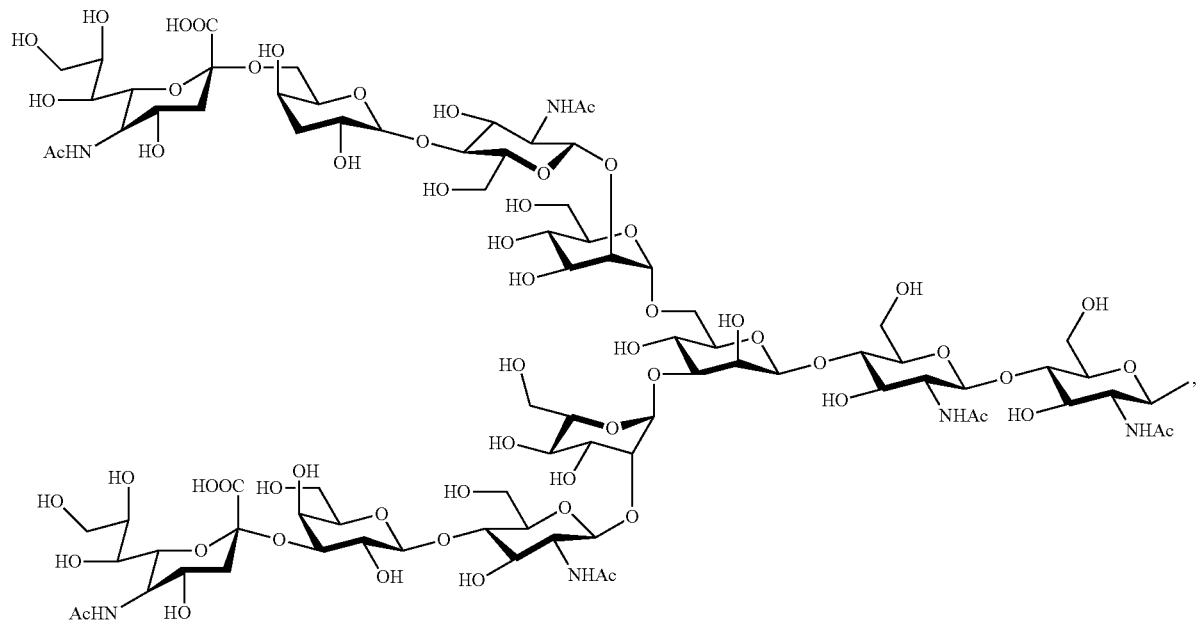
1S2S(3)-11NC, 34
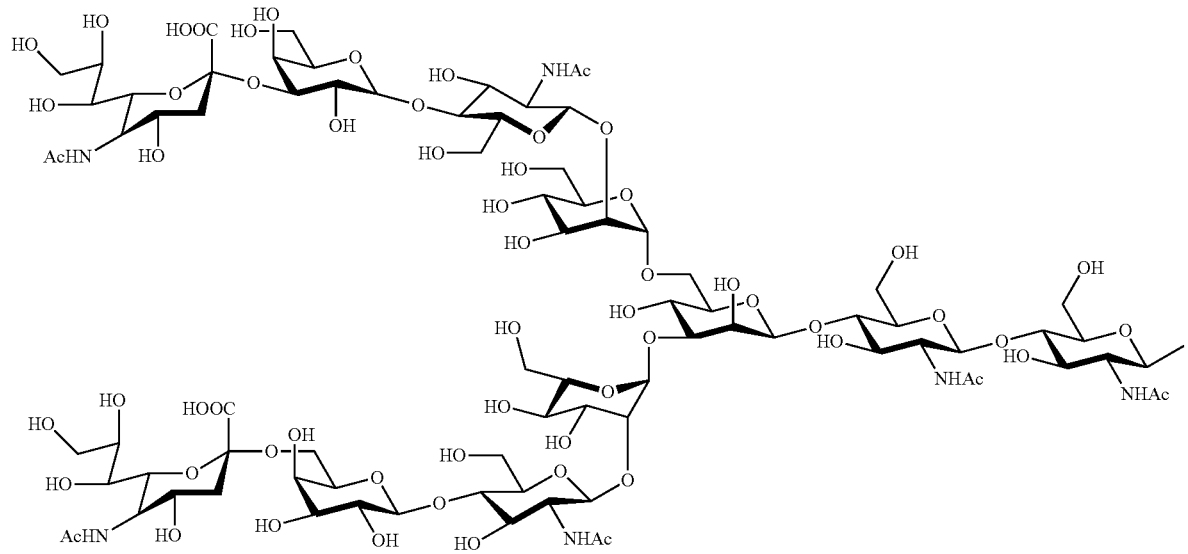
1S(3)2S-11NC, 35
According to one embodiment, the sugar chain of the present invention is preferably a sugar chain having a linear structure. Examples of such a sugar chain include oligohyaluronic acid. In the present specification, the oligohyaluronic acid refers to a sugar chain in which 2 to 32 sugars, preferably 2 to 16 sugars, more preferably 4 to 8 sugars, alternating between N-acetylglucosamine and glucuronic acid are bonded in a linear form.

Particularly preferred examples of the oligohyaluronic acid used in the present invention include sugar chains of 2 units (4 sugars) or more and 8 units (16 sugars) or less when a unit consisting of N-acetylglucosamine and glucuronic acid is defined as 1 unit. A sugar chain of 2 units (4 sugars) to 4 units (8 sugars) is further preferred, and a sugar chain of 2 units (4 sugars) is most preferred.

Examples of the hyaluronic acid preferably used in the present invention include oligohyaluronic acid of 4 sugars:

[Formula 28]

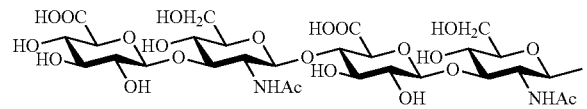

and oligohyaluronic acid of 8 sugars:

[Formula 29]

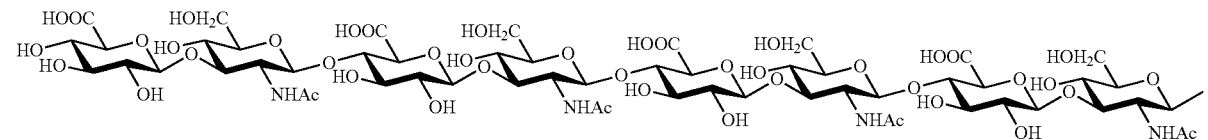

For the sugar chains specifically listed above, a hydroxy group and/or a carboxy group in each sugar residue constituting each sugar chain may be protected with a protective group. The protective group is, for example, a protective group generally known to those skilled in the art which is introduced for the purpose of protecting the hydroxy group and/or the carboxy group in the sugar residue through chemical reaction. More specific examples thereof can include, but are not limited to, an alkyl group (methyl group, ethyl group, etc.), a benzyl group, an acyl group (acetyl group, benzoyl group, pivaloyl group, etc.), a tert-butyldimethylsilyl group, a tert-butyldiphenylsilyl group, a phenacyl group, and an allyl group.

In the present specification, the "glycosylated amino acid" is an amino acid bonded to a sugar chain. In the present specification, the "amino acid" is used in the broadest sense and includes natural amino acids, for example, serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro) as well as nonnatural amino acids such as amino acid variants and derivatives. Considering this broad definition, those skilled in the art should naturally understand that examples of the amino acid used in the present specification include: L-amino acids; D-amino acids; chemically modified amino acids such as amino acid variants and amino acid derivatives; amino acids that do not serve as protein constituents in vivo, such as norleucine, β-alanine, and ornithine; and chemically synthesized compounds having the properties of amino acids generally known to those skilled in the art. Examples of the nonnatural amino acids include α-methylamino acids (α-methylalanine, etc.), D-amino acids (D-aspartic acid, D-glutamic acid, etc.), histidine-like amino acids (2-amino-histidine, β-hydroxy-histidine, homohistidine, α-fluoromethyl-histidine, α-methyl-histidine, etc.), amino acids having extra methylene in their side chains ("homo" amino acids), and amino acids in which a carboxylic acid functional group amino acid in a side chain is replaced by a sulfonic acid group (cysteic acid, etc.).

In the present specification, the binding site between the sugar chain and the amino acid in the "glycosylated amino acid" is not particularly limited and is preferably the reducing end of the sugar chain to which the amino acid is bonded. The amino acid to be bonded to the sugar chain is not particularly limited by its type, and any of natural amino acids, nonnatural amino acids, and D-amino acids can also be used. The glycosylated amino acid is preferably glycosylated Asn as in a N-linked sugar chain, or glycosylated Ser or glycosylated Thr as in an O-linked sugar chain, from the viewpoint that the glycosylated amino acid is structurally identical or similar to an in vivo glycopeptide (glycoprotein).

The sugar chain and the amino acid may be bonded to each other without the mediation of a linker or may be bonded to each other via a linker. When the sugar chain and the amino acid are bonded to each other via a linker, the amino acid in the glycosylated amino acid is preferably an amino acid having two or more carboxy groups in the molecule, such as aspartic acid or glutamic acid; an amino acid having two or more amino groups in the molecule, such as lysine, arginine, asparagine, histidine, or tryptophan; an amino acid having a hydroxy group in the molecule, such as serine, threonine, or tyrosine; an amino acid having a thiol group in the molecule, such as cysteine; or an amino acid having an amide group in the molecule, such as asparagine or glutamine, from the viewpoint of easy bonding to the linker. Particularly, the amino acid in the glycosylated amino acid is preferably aspartic acid, glutamic acid, lysine, arginine, serine, threonine, cysteine, asparagine, or glutamine, more preferably cysteine or asparagine, from the viewpoint of reactivity.

When the sugar chain and the amino acid are bonded to each other via a linker, any linker used in the art can be widely used. Examples of the linker can include:

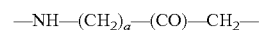

wherein a represents an integer and is preferably an integer of 0 to 4, though there is no limitation unless it inhibits the linker functions of interest;

C1-10 polymethylene;

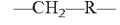

wherein R represents a group formed by the elimination of one hydrogen atom from a group selected from the group consisting of alkyl, substituted alkyl, alkenyl, substituted alkenyl, alkynyl, substituted alkynyl, aryl, substituted aryl, a carbocyclic group, a substituted carbocyclic group, a heterocyclic group, and a substituted heterocyclic group; and —(CO)—(CH$_2$)$_a$—(CO)— wherein a represents an integer and is preferably an integer of 0 to 4, though there is no limitation unless it inhibits the linker functions of interest.

According to one embodiment, when the sugar chain and the amino acid are bonded without the mediation of a linker in the glycosylated amino acid according to the present invention, for example, a hydrogen atom on the side chain amino group of asparagine may be replaced by the reducing end of the sugar chain. In this case, a leaving group present in the reducing end of the sugar chain is not limited and may be, for example, chlorine, bromine, or fluorine.

According to one embodiment, when the sugar chain and the amino acid are bonded via a linker in the glycosylated amino acid according to the present invention, for example, a hydrogen atom on the side chain thiol group of cysteine is bonded to the reducing end of the sugar chain via the linker (e.g., in the case of a linker —CH$_2$—CONH—, the reducing end of the sugar chain is bonded to the nitrogen atom in the linker). In this case, a leaving group in the linker bonded to the reducing end of the sugar chain is not limited and may be, for example, chlorine, bromine, or fluorine.

In the present specification, the "glycosylated polypeptide" is not particularly limited as long as the glycosylated polypeptide is a compound in which at least one sugar chain is added to a protein (or polypeptide or peptide). In the present specification, the glycosylated polypeptide may be used interchangeably with a "glycoprotein" or a "glycopeptide". The glycosylated polypeptide may be a polypeptide containing the glycosylated amino acid mentioned above. The binding manner between the sugar chain and the amino acid in the glycosylated polypeptide, and the types of amino acids constituting the polypeptide, etc., may be defined similarly to those in the glycosylated amino acid according to the present invention. The amino acid (residue) at which the polypeptide is bonded to the sugar chain is not limited to the N or C terminus of the polypeptide and may be any appropriate amino acid (residue) constituting the polypeptide. The amino acid residues in the glycosylated polypeptide according to the present invention may be preferably 2 to 100 amino acid residues, more preferably 2 to 10 amino acid residues. In the glycosylated polypeptide according to the present invention, the amino acids other than the amino acid at which the polypeptide is bonded to the sugar chain can be relatively arbitrarily selected. Those skilled in the art understand that according to one embodiment, the amino acid at which the polypeptide is bonded to the sugar chain is, for example, asparagine, cysteine, lysine, or glutamine, while the amino acids other than the amino acid at which the polypeptide is bonded to the sugar chain (e.g., an amino acid to be bonded to the (glycosylated) linker moiety) are not particularly limited.

The amino acid constituting the glycosylated amino acid or the glycosylated polypeptide according to the present invention is preferably an amino acid present in vivo, from the viewpoint of administering the compound of the present invention or the salt thereof into an organism.

According to one embodiment, the glycosylated linker of the present invention can be a thioalkyl-type glycosylated linker.

In the present specification, the thioalkyl-type glycosylated linker refers to a glycosylated linker that is capable of binding to the physiologically active substance via a thioester bond and has an alkyl structure in its structure.

In the present specification, the thioalkyl-type glycosylated linker also includes a glycosylated linker that is capable of binding to the physiologically active substance via a thioester bond and has an alkynyl or alkenyl structure in its structure.

More specifically, the thioalkyl-type glycosylated linker is a glycosylated linker represented by the formula (A) wherein X represents a sulfur atom (S) having a leaving group;

R$^1$ is substituted or unsubstituted C$_1$-C$_5$ alkyl, substituted or unsubstituted C$_2$-C$_5$ alkenyl, or substituted or unsubstituted C$_2$-C$_5$ alkynyl, or R$^1$ represents —R$^3$—R$^4$—, —R$^4$—R$^5$—, or —R$^3$—R$^4$—R$^5$—, wherein R$^3$ and R$^5$ each represent substituted or unsubstituted C$_1$-C$_5$ alkyl, substituted or unsubstituted C$_2$-C$_5$ alkenyl, or substituted or unsubstituted C$_1$-C$_5$ alkynyl, and R$^4$ represents substituted or unsubstituted C$_5$-C$_{16}$ aryl, substituted or unsubstituted C$_5$-C$_{16}$ heteroaryl, or a sulfur atom (S);

Y may be present or absent in the formula (A), and when Y is present in the formula (A), Y represents —CO— or —CONH— (provided that C is bonded to R$^1$ in the formula (A) and N is bonded to R$^2$ in the formula (A)); and R$^2$ is a sugar chain, a glycosylated amino acid, or a glycosylated polypeptide, or R$^2$ represents —R$^6$—R$^7$, wherein R$^6$ represents a sugar chain, a glycosylated amino acid, or a glycosylated polypeptide, and R$^7$ represents a hydrogen atom (H), —NH$_2$, substituted or unsubstituted C$_1$-C$_5$ alkyl, substituted or unsubstituted C$_5$-C$_{16}$ aryl, substituted or unsubstituted C$_5$-C$_{16}$ heteroaryl, a nucleic acid, or PEG.

According to one embodiment, the glycosylated linker of the present invention can be a thioaryl-type glycosylated linker.

In the present specification, the thioaryl-type glycosylated linker refers to a glycosylated linker that is capable of binding to the physiologically active substance via a thioester bond and has an aryl structure in its structure.

More specifically, the thioalkyl-type glycosylated linker is a glycosylated linker represented by the formula (A) wherein X represents a sulfur atom (S) having a leaving group;

R$^1$ represents substituted or unsubstituted C$_1$-C$_5$ aryl or substituted or unsubstituted C$_5$-C$_{16}$ heteroaryl;

Y may be present or absent in the formula (A), and when Y is present in the formula (A), Y represents —CO— or —CONH— (provided that C is bonded to R$^1$ in the formula (A) and N is bonded to R$^2$ in the formula (A)); and R$^2$ is a sugar chain, a glycosylated amino acid, or a glycosylated polypeptide, or R$^2$ represents —R$^6$—R$^7$, wherein R$^6$ represents a sugar chain, a glycosylated amino acid, or a glycosylated polypeptide, and R$^7$ represents a hydrogen atom (H), —NH$_2$, substituted or unsubstituted C$_1$-C$_5$ alkyl, substituted or unsubstituted C$_5$-C$_{16}$ aryl, substituted or unsubstituted C$_5$-C$_{16}$ heteroaryl, a nucleic acid, or PEG.

According to a preferred embodiment of the present invention, sugar chains in the compound comprising a glycosylated linker moiety and a physiologically active substance moiety according to the present invention or the salt thereof are preferably homogeneous. In the present specification, "sugar chains are homogeneous" means that the glycosylation site, the type of each sugar constituting the sugar chain, binding order, and binding pattern between sugars are identical among glycosylated linker moieties when sugar chains are compared among the glycosylated linker moieties. In the case of preparation intended to add a plurality of identical sugar chains into a glycosylated linker moiety, "sugar chains are homogeneous" also means that the type of each sugar constituting the sugar chain, binding order, and binding pattern between sugars are identical when the structures of the added plurality of sugar chains are compared within the glycosylated linker moiety. Specifically, "sugar chains are homogeneous" means that at least 90% or more, preferably 95% or more, more preferably 99% or more sugar chains are structurally uniform when sugar chains are compared among the glycosylated linker moieties or within the glycosylated linker moiety.

The ratio of homogeneous sugar chains or the ratio of homogeneously glycosylated linkers can be measured by a method using, for example, HPLC, capillary electrophoresis, NMR, or mass spectrometry.

The glycosylated amino acid or the glycosylated polypeptide in which amino acid sequence and/or sugar chains are substantially homogeneous, used in the present invention, can be produced by a glycosylation step in combination with a peptide production method generally known to those skilled in the art, such as solid-phase synthesis, liquid-phase synthesize, cell-based synthesis, separation and extraction of a natural product. For such a method for producing the glycosylated polypeptide, see, for example, International Publication Nos. WO 2010/021126 and WO 2004/005330.

For the method for producing the sugar chain for use in the glycosylation step, see, for example, International Publication Nos. WO 03/008431, WO 2004/058984, WO 2004/008431, WO 2004/058824, WO 2004/070046, and WO 2007/011055.

According to one embodiment, the glycosylated polypeptide used in the present invention may include, but is not limited to, for example: glycosylated amino acids or glycosylated polypeptides in which a sugar chain unbound with an amino acid is bonded directly or via a linker to an amino acid or an amino acid on a polypeptide; glycosylated polypeptides derived from these glycosylated amino acids or glycosylated polypeptides as a result of elongating the already added sugar chain by the further addition of a sugar or a sugar chain to the added sugar chain; glycosylated polypeptides in which one or more (e.g., 2 to 30, preferably 2 to 10) amino acids are bonded to, for example, an amino group and/or a carboxy group, in a glycosylated amino acid and an amino acid or a polypeptide is further linked thereto; and glycosylated polypeptides in which a sugar chain bound with an amino acid is bonded to an amino acid on a polypeptide via a linker.

Alternatively, the glycosylated amino acid or the glycosylated polypeptide having the desired sugar chain structure may be efficiently obtained by the transfer of various sugars (e.g., fucose) to the glycosylated amino acid or the glycosylated polypeptide according to the present invention using glycosyltransferase. For example, the glycosylated amino acid or the glycosylated polypeptide having the desired sugar chain structure containing fucose can be obtained by the transfer of fucose using glycosyltransferase (fucosyltransferase). Also, the glycosylated amino acid or the glycosylated polypeptide having the desired sugar chain structure with a distinctive binding pattern can be obtained depending on the glycosyltransferase used.

Generally commercially available fucose or chemically synthesized fucose can be used as the fucose.

Generally commercially available, naturally occurring, or genetically recombined fucosyltransferase can be used. The fucosyltransferase used can be appropriately selected according to the type of the fucose to be transferred. Specific examples thereof can include fucosyltransferase V (human, recombinant, plasma-derived, serum-derived, milk-derived, or liver-derived), which is an enzyme transferring fucose to N-acetylglucosamine at the non-reducing end of sugar chain asparagine. Alternatively, fucose may be transferred by shifting the equilibrium by pH adjustment or the like using fucose hydrolase.

In the present specification, the "nucleic acid" refers to DNA or RNA in which nucleotides each composed of a base (adenine, guanine, thymine, cytosine, or uracil), a sugar residue, and phosphate are bonded through a phosphoester bond, and has 2 to 2000 nucleotide residues.

In the present specification, the "PEG" is a polymer of ethylene glycol and can be represented by, for example, "(—CH2-CH2-O-)n" (wherein n represents an integer of 2 to 10000).

According to one embodiment, the glycosylated linker of the present invention is preferably a glycosylated linker represented by the formula (A): X—$R^1$—Y—$R^2$, wherein X represents an oxygen atom (O) having a leaving group or a sulfur atom (S) having a leaving group;

$R^1$ is aryl such as benzyl or tolyl, or $R^1$ represents —$R^3$—$R^4$—$R^5$—, wherein $R^3$ represents —$CH_2CH_2$—, $R^4$ represents a sulfur atom (S), and $R^5$ represents —$CH_2$— (i.e., $R^1$ is thioether represented by —$CH_2CH_2SCH_2$—);

Y represents —CO—; and $R^2$ represents NH-sugar chain, glycosylated Asn, glycosylated Cys, or glycosylated Asn or glycosylated Cys with one or more (e.g., 2, 3, 4, or 5) amino acids added to the C terminus.

The glycosylated linker of the present invention can be produced by solid-phase synthesis, liquid-phase synthesis, or the like.

In the case of producing the glycosylated linker represented by the formula (A): X—$R^1$—Y—$R^2$ by, for example, solid-phase synthesis, appropriate compounds are bonded onto a resin in the order of $R^2$, Y (only in the case where Y is present), $R^1$, and X on the resin. In this operation, $R^2$, Y, $R^1$, and X may be sequentially bonded onto the resin on a constituent basis, or a compound corresponding to two or more consecutive constituents may be bonded onto the resin. As an example of bonding a compound corresponding to two or more consecutive constituents onto the resin, for example, $R^2$ having a leaving group is first bonded onto the resin. Next, one compound of X—$R^1$—Y having a leaving group at the end of Y can be condensed with $R^2$ on the resin so that the leaving groups of $R^2$ and Y are eliminated to prepare the glycosylated linker represented by the formula (A): X—$R^1$—Y—$R^2$ on the resin. The compound corresponding to two or more consecutive constituents is not limited to X—$R^1$—Y and also includes other combinations of two or more selected from the 4 constituents X, $R^1$, Y, and $R^2$.

Hereinafter, a more specific production example by the solid-phase synthesis method will be shown.

Specifically, the production method by the solid-phase synthesis method comprises the steps of:

bonding a compound of $R^2$ (sugar chain, glycosylated amino acid, glycosylated polypeptide, etc.) having a leaving group onto a resin;

bonding Y having at least two leaving groups to $R^2$ on the resin, wherein $R^2$ and Y bind to each other by the elimination of the leaving groups of $R^2$ and Y;

bonding a compound corresponding to the $R^1$ moiety having at least two leaving groups to Y—$R^2$ on the resin, wherein Y and $R^1$ bind to each other by the elimination of the leaving groups of Y and $R^1$;

bonding a compound corresponding to the X moiety having at least two leaving groups to $R^1$—Y—$R^2$ on the resin, wherein $R^1$ and X bind to each other by the elimination of the leaving groups of $R^1$ and X; and separating X—$R^1$—Y—$R^2$ synthesized on the resin from the resin.

In a production example in which, for example, one compound corresponding to the X—$R^1$—Y moiety is used and bonded onto a resin in the method for producing the glycosylated linker by the solid-phase synthesis method, the glycosylated linker can be prepared by a production method comprising the steps of:

bonding a compound of $R^2$ (sugar chain, glycosylated amino acid, glycosylated polypeptide, etc.) having a leaving group onto a resin;

bonding a compound of X—$R^1$—Y having a leaving group at the end of Y to $R^2$ on the resin so that Y is condensed with $R^2$ by the elimination of the leaving groups of $R^2$ and Y to form X—$R^1$—Y—$R^2$ on the resin; and separating X—$R^1$—Y—$R^2$ synthesized on the resin from the resin.

In the method for producing the glycosylated linker by the solid-phase synthesis method, the glycosylated linker formed on the resin can be further linked to an amino acid (more specifically, the oxygen atom having a leaving group or the sulfur atom having a leaving group, represented by X can be further linked to an amino acid) without being cleaved from the resin. This eliminates the need of separating the glycosylated linker from the resin and can produce the compound comprising a physiologically active substance moiety and a glycosylated linker moiety on the resin.

The resin for use in solid-phase synthesis can be any resin usually used in solid-phase synthesis. For example, chlorine-functionalized 2-chlorotrityl chloride resin (manufactured by Merck KGaA), amino group-functionalized Amino-PEGA resin (manufactured by Merck KGaA), NovaSyn TGT alcohol resin having a hydroxy group (manufactured by Merck KGaA), Wang resin (manufactured by Merck KGaA), HMPA-PEGA resin (manufactured by Merck KGaA), or Link Amide resin (manufactured by Merck KGaA) can be used. Alternatively, a linker may be located between the Amino-PEGA resin and the amino acid. Examples of such a linker can include 4-hydroxymethyl-phenoxyacetic acid (HMPA) and 4-(4-hydroxymethyl-3-methoxyphenoxy)-butylacetic acid (HMPB). For example, H-Cys(Trt)-Trityl NovaPEG resin (manufactured by Merck KGaA), which is a resin bonded in advance at a C-terminal amino acid, may be used.

In the case of amidating the C terminus of an amino acid or a peptide present in the glycosylated linker produced by solid-phase synthesis, for example, amino group-functionalized Rink-Amide-PEGA resin (manufactured by Merck KGaA) can be used. The C-terminal amino acid of the amino acid or the peptide in the glycosylated linker can be amidated by the cleavage between this resin and the peptide with an acid.

The 2-chlorotrityl chloride resin is preferred because the racemization of terminal Cys can be prevented when a peptide chain is elongated in solid-phase synthesis.

When the step of bonding a compound corresponding to the $R^2$ moiety (sugar chain, glycosylated amino acid, glycosylated polypeptide, etc.) onto the resin involves bonding a glycosylated amino acid onto the resin, a glycosylated amino acid with an amino acid protected with a lipid-soluble protective group is bonded thereto. In the case of bonding a glycopolypeptide onto the resin, desired amino acids and glycosylated amino acids can be sequentially bonded onto the resin to synthesize the glycosylated polypeptide on the resin.

Examples of the lipid-soluble protective group can include carbonate or amide protective groups such as a 9-fluorenylmethoxycarbonyl (Fmoc) group, a t-butyloxycarbonyl (Boc) group, a benzyl group, an allyl group, an allyloxycarbonyl group, and an acetyl group. In the case of introducing the lipid-soluble protective group to the amino acid, for example, an Fmoc group, 9-fluorenylmethyl-N-succinimidyl carbonate and sodium bicarbonate can be added and reacted to introduce the Fmoc group. The reaction is preferably carried out at 0 to 50° C., preferably at room temperature, for approximately 1 to 5 hours.

A commercially available product also can be used as the amino acid protected with the lipid-soluble protective group. Examples thereof can include Fmoc-Ser-OH, Fmoc-Asn-OH, Fmoc-Val-OH, Fmoc-Leu-OH, Fmoc-Ile-OH, Fmoc-Ala-OH, Fmoc-Tyr-OH, Fmoc-Gly-OH, Fmoc-Lys-OH, Fmoc-Arg-OH, Fmoc-His-OH, Fmoc-Asp-OH, Fmoc-Glu-OH, Fmoc-Gln-OH, Fmoc-Thr-OH, Fmoc-Cys-OH, Fmoc-Met-OH, Fmoc-Phe-OH, Fmoc-Trp-OH, Fmoc-Pro-OH, Boc-Ser-OH, Boc-Asn-OH, Boc-Val-OH, Boc-Leu-OH, Boc-Ile-OH, Boc-Ala-OH, Boc-Tyr-OH, Boc-Gly-OH, Boc-Lys-OH, Boc-Arg-OH, Boc-His-OH, Boc-Asp-OH, Boc-Glu-OH, Boc-Gln-OH, Boc-Thr-OH, Boc-Cys-OH, Boc-Met-OH, Boc-Phe-OH, Boc-Trp-OH, and Boc-Pro-OH.

Examples of the amino acid protected with the lipid-soluble protective group in which the protective group is introduced in the side chain can include Fmoc-Arg(Pbf)-OH, Fmoc-Asn(Trt)-OH, Fmoc-Asp(OtBu)-OH, Fmoc-Cys(Acm)-OH, Fmoc-Cys(StBu)-OH, Fmoc-Cys(tBu)-OH, Fmoc-Cys(Trt)-OH, Fmoc-Glu(OtBu)-OH, Fmoc-Gln(Trt)-OH, Fmoc-His(Trt)-OH, Fmoc-Lys(Boc)-OH, Fmoc-Ser(tBu)-OH, Fmoc-Thr(tBu)-OH, Fmoc-Trp(Boc)-OH, Fmoc-Tyr(tBu)-OH, Boc-Arg(di-Z)—OH, Fmoc-Asp(OBzl)-OH, Boc-Cys(Bzl)-OH, Boc-Glu(OBzl)-OH, Boc-His(Dnp)-OH, Boc-Lys(2-Cl—Z)—OH, Boc-Ser(Bzl)-OH, Boc-Thr(Bzl)-OH, Boc-Trp(For)-OH, and Boc-Tyr(Bzl)-OH.

Examples of the glycosylated amino acid with an amino acid protected with a lipid-soluble protective group can include Fmoc-glycosylated Asn and Boc-glycosylated Asn.

Amino acids glycosylated by the sugar chains mentioned above having identical sugar chain structures are used as these glycosylated amino acids. Such sugar chains can be obtained by any method known in the art. For example, the chemical synthesis of sugar chains (see, e.g., J. Seifert et al. Angew Chem Int. Ed. 2000, 39, pp. 531-534), separation from a natural or artificial sugar chain source, or a commercially available product can be used as a specific approach, though there is no limitation. The glycosylated amino acids having identical structures in the approach are not limited, and, for example, the separation of sugar chains having identical structures from a natural or artificial sugar chain source can be carried out by a method described in, for example, WO 2004/058789. Specifically, a mixture containing sugar chain asparagine (sialylglycopeptide (SGP)) is isolated from a natural sugar chain source such as a chicken egg by a method described in, for example, Seko et al., Biochim Biophys Acta. 1997; 1335 (1-2): 23-32. A lipid-soluble protective group (e.g., Fmoc) is introduced into the sugar chain asparagine to obtain a sugar chain asparagine derivative mixture. This mixture can be subjected to chromatography so that sugar chains having various structures contained in the mixture are separated according to their structures. Alternatively, sugar chain asparagine having a particular structure with or without various protective groups is available from, for example, GlyTech, Inc.

The reaction for bonding the amino acid or the glycosylated amino acid to the resin is preferably carried out, for example, by placing a resin in a solid-phase column, washing this resin with a solvent, and then adding an amino acid solution thereto. Examples of the solvent for washing can include dimethylformamide (DMF), 2-propanol, and dichloromethane. Examples of the solvent for dissolving the amino acid can include dimethyl sulfoxide (DMSO), DMF, and dichloromethane. The binding reaction between the resin and the amino acid or the glycosylated amino acid can be carried out at 0 to 50° C., preferably at room temperature, for approximately 10 minutes to 30 hours, preferably approximately 15 minutes to 24 hours.

In this reaction, a condensing agent can be used, such as dicyclohexylcarbodiimide (DCC), 1-ethyl-3-(3-dimethylaminopropyl)carbodiimide hydrochloride (WSC/HCl), diphenylphosphorylazide (DPPA), carbonyldiimidazole (CDI), diethyl cyanophosphonate (DEPC), 1,3-diisopropylcarbodiimide (DIC), benzotriazol-1-yloxy-trispyrrolidinophosphonium hexafluorophosphate (PyBOP), 3-diethoxyphosphoryloxy-1,2,3-benzotriazin-4(3H)-one (DEPBT), 1-hydroxybenzotriazole (HOBt), hydroxysuccinimide (HOSu), dimethylaminopyridine (DMAP), 1-hydroxy-7-azabenzotriazole (HOAt), 3-hydroxy-4-oxo-3,4-dihydro-5-azabenzo-1,2,3-triazine (HODhbt), hydroxyphthalimide (HOPht), pentafluorophenol (Pfp-OH), 2-(1H-benzotriazol-1-yl)-1,1,3,3-tetramethyluronium hexafluorophosphate (HBTU), O-(6-chloro-1H-benzotriazol-1-yl)-N,N,N',N'-tetramethyluronium hexafluorophosphate (HCTU), O-(7-azabenzotriazol-1-yl)-1,1,3,3-tetramethyluronium hexafluorophosphonate (HATU), or O-benzotriazol-1-yl-1,1,3,3-tetramethyluronium tetrafluoroborate (TBTU). The ratio between the amino acid or the glycosylated amino acid and the dehydration condensation agent used is usually 1 to 10 parts by weight, preferably 2 to 5 parts by weight, of the dehydration condensation agent with respect to 1 part by weight of the amino acid or the glycosylated amino acid.

When a sugar chain having sialic acid at the non-reducing end is used, the sialic acid may be dissociated by acid treatment in a cleavage step from the resin. Accordingly, for introducing the sugar chain having sialic acid to the linker moiety prior to the cleavage step using an acid, it is preferred to use a sugar chain in which the carboxy group of the sialic acid on the sugar chain to be introduced is protected with a protective group. Examples of the protective group for the carboxyl group of the sialic acid include an aryl group including a benzyl (Bn) group or the like, an alkyl group including an ethyl group (Et) and a methyl group (Me) or the like, a diphenylmethyl group, a phenacyl group, an alkoxy group, and a phenacyl group in which a hydrogen atom bonded to ring structure-forming carbon is substituted by a nitro group or the like. More specifically, a protective group that protects the carboxy group of the sialic acid as shown in, for example, —COOBn, —COOEt, —COOMe, —COOCH(Ph)$_2$, —COOCH$_2$COPh, —COOCH$_2$PhOMe, —COOCH$_2$Ph(OMe)$_2$, —COOCH$_2$PhNO$_2$, or —COOCH$_2$Ph(NO$_2$)$_2$ is preferred. Such protection of the carboxy group of the sialic acid with a benzyl group or the like can prevent the elimination of the acid-labile sialic acid.

The protection reaction of the carboxy group of the sialic acid on the sugar chain can be carried out by a method well known to those skilled in the art. The protective group in the carboxy group of the sialic acid protected with, for example, a benzyl group, a diphenylmethyl group, or a phenacyl group can also be deprotected by a method well known to those skilled in the art. For example, the deprotection reaction can be carried out by hydrolysis under basic conditions, though there is no limitation. The deprotection reaction is preferably carried out at usually 0 to 50° C., preferably 0 to 40° C., more preferably 0 to 30° C. Usually, the reaction time is preferably approximately 5 minutes to 5 hours. After the completion of the reaction, the reaction product is preferably neutralized with a weak acid such as phosphoric acid or acetic acid and then appropriately purified by a method known in the art (e.g., high-performance liquid column chromatography (HPLC)).

When $R^2$ is a nucleic acid or PEG, the corresponding compound can also be appropriately bonded to the resin by a method well known to those skilled in the art.

When $R^2$ is a sugar chain, a non-glycosylated linker structure is synthesized on a resin, and a sugar chain can be added to the end of the linker after cleavage and isolation from the resin to produce the glycosylated linker. The linker to be glycosylated is designed so as to have, for example, a thiol group at the end. As a result, the thiol group present at the end of the linker after the isolation from the resin can be bonded to a haloacetylated complex-type sugar chain derivative (or a haloacetamidated complex-type sugar chain derivative) to introduce the sugar chain to the end of the linker.

Also, when $R^2$ is a nucleic acid or PEG, a non-nucleic acid- or non-PEG-added linker structure is synthesized on a resin, and a nucleic acid or PEG can be added to the end of the linker after cleavage and isolation from the resin to produce the nucleic acid- or PEG-added linker. The linker to which a nucleic acid or PEG is to be added is designed so as to have, for example, a thiol group at the end. As a result, the thiol group present at the end of the linker after the isolation from the resin can be bonded to a nucleic acid or PEG in a haloacetylated form (or a haloacetamidated form) or the like to introduce the nucleic acid or PEG.

Even when $R^2$ is a glycosylated amino acid or a glycosylated polypeptide, only a non-glycosylated linker structure may be synthesized beforehand on a resin, and a sugar chain can then be bonded to the $R^2$ moiety. The reaction for bonding the sugar chain to $R^2$ may be carried out on the resin subsequently to the solid-phase synthesis or may be carried out after separation from the resin. When the sugar chain is bonded thereto on the resin subsequently to the solid-phase synthesis, the glycosylation step may be carried out after synthesis of the physiologically active substance moiety or may be carried out before synthesis of the physiologically active substance moiety.

In order to add a sugar chain to the synthesized compound having a linker or linker moiety and a physiologically active substance moiety, a haloacetylated complex-type sugar chain derivative (or a haloacetamidated complex-type sugar chain derivative) can be reacted with the linker (containing unprotected Cys) or the compound (containing unprotected Cys) having a linker moiety and a physiologically active substance moiety, as mentioned above, so that the sugar chain is reacted with the thiol group of the unprotected Cys for bonding to the peptide. This reaction is preferably carried out at usually 0 to 80° C., preferably 10 to 60° C., more preferably 15 to 35° C., in a phosphate buffer solution, a tris-HCl buffer solution, a citrate buffer solution, acetonitrile, DMSO, or a mixed solution thereof. The reaction time is usually approximately 10 minutes to 24 hours, preferably, usually approximately 30 minutes to 5 hours. After the completion of the reaction, preferably, the reaction product is appropriately purified by a method known in the art (e.g., HPLC).

The haloacetylated complex-type sugar chain derivative (or the haloacetamidated complex-type sugar chain derivative) is a compound in which a hydroxy group bonded to carbon at the position 1 of the reducing end of, for example, a complex-type asparagine-linked sugar chain is substituted by —NH—(CH$_2$)$_a$—(CO)—CH$_2$X (wherein X represents a halogen atom, and a represents an integer and is preferably an integer of 0 to 4, though there is no limitation unless it inhibits the linker functions of interest).

As a more specific example, the reaction between the haloacetylated complex-type sugar chain derivative and the Cys-containing peptide can be carried out at room temperature in a phosphate buffer solution. After the completion of the reaction, a glycosylated polypeptide substituted by glycosylated Cys can be obtained by HPLC purification.

Alternatively, the reaction may be carried out in a mixed solution of an organic solvent such as DMSO, DMF, methanol, or acetonitrile with the buffer solution mentioned above. In this respect, the organic solvent can be added at a ratio ranging from 0 to 99% (v/v) to the buffer solution. For an unprotected Cys-containing peptide low soluble in the buffer solution, the addition of such an organic solvent is preferred because the solubility in the reaction solution can be improved.

Also, the reaction may be carried out in an organic solvent such as DMSO, DMF, methanol, or acetonitrile, or a mixed solution thereof. In this respect, the reaction is preferably carried out in the presence of a base. Examples of the base can include DIPEA, triethylamine, pyridine, and 2,4,6-collidine.

Furthermore, the reaction may be carried out in a mixed solution of a buffer solution supplemented with guanidine hydrochloride or urea. The guanidine hydrochloride or the urea can be added at a final concentration of 1 M to 8 M to the buffer solution. The addition of this guanidine hydrochloride or urea is also preferred because the solubility of the peptide low soluble in the buffer solution can be improved.

The reaction between the nucleic acid or PEG in a haloacetylated form (or a haloacetamidated form) or the like and the Cys-containing peptide can also be appropriately carried out by a method generally known to those skilled in the art.

For the step of bonding a compound corresponding to the Y moiety to R$^2$ on the resin, the step of bonding a compound corresponding to the R$^1$ moiety to Y—R$^2$ on the resin, and the step of bonding a compound corresponding to the X moiety to R$^1$—Y—R$^2$ on the resin, those skilled in the art can appropriately design and select the compound corresponding to each constituent and condense the compound with R$^2$ on the resin.

For bonding a compound corresponding to two or more consecutive constituents onto the resin, those skilled in the art can also appropriately design and select the compound and reaction conditions.

A moiety corresponding to X (an oxygen atom having a leaving group or a sulfur atom having a leaving group) in the glycosylated linker may require a protective group for synthesis. Examples of the protective group for the oxygen atom can include a trityl group, a methoxytrityl group, a t-butyl group, and a benzyl group. Examples of the protective group for the sulfur atom can include a trityl group, a methoxytrityl group, a t-butyl group, a t-butylthio group, and an Acm group. The protective group can be introduced thereto by a well known conventional method.

The step of separating the glycosylated linker (represented by the formula (A): X—R$^1$—Y—R$^2$) synthesized on the resin from the resin is preferably carried out by treatment with an acid. Examples of the acid can include a mixed solution of trifluoroacetic acid (TFA), triisopropylsilane, ethanedithiol, and water (90:5:2.5:2.5), a mixed solution of acetic acid and trifluoroethanol (50:50), and HCl.

When a compound in which a glycosylated linker and a physiologically active substance are bonded to each other is synthesized on a resin, the step of separating the compound from the resin is also preferably carried out by treatment with an acid. The acid used and the reaction conditions can be set to the same as the conditions for separating the glycosylated linker from the resin.

The glycosylated linker thus produced binds, at the oxygen atom having a leaving group or the sulfur atom having a leaving group, to a physiologically active substance. The glycosylated linker can enhance the water solubility of a physiologically active substance by binding to the physiologically active substance as described above. In addition, the glycosylated linker can preferably reduce the antigenicity of the physiologically active substance.

The glycosylated linker bonded to the physiologically active substance can release the physiologically active substance within a given time under particular temperature and pH conditions depending on its structure. This released physiologically active substance maintains its original functions. The physiologically active substance released from the glycosylated linker exerts its original functions, for example, in vivo.

When the bonding between the glycosylated linker moiety and the physiologically active substance moiety is a thioester bond rather than an ester bond, the hydrolysis rate can be accelerated. Also, a glycosylated linker having a thioaryl structure among the thioester bonds is hydrolyzed more rapidly than a glycosylated linker having a thioalkyl structure.

Those skilled in the art can design a glycosylated linker having a desired release time of the physiologically active substance by appropriately changing the structure of the glycosylated linker moiety.

In the present invention, the physiologically active substance can bind to the glycosylated linker moiety as a result of partial alteration (modification) of the structure of the physiologically active substance. However, once the glycosylated linker moiety is cleaved, the physiologically active substance is released. Preferably, the released physiologically active substance is structurally the same as the compound before the bonding to the glycosylated linker moiety (before the modification). In the present specification, the physiologically active substance unbound with the glycosylated linker is referred to as an "unmodified physiologically active substance". Preferably, the unmodified physiologically active substance has the original pharmacokinetic, immunogenic, toxicological, or pharmacological properties of the physiologically active substance itself. The properties may be altered or modified, for example. Preferably, the "compound comprising a glycosylated linker moiety and a physiologically active substance moiety, or the salt thereof" according to the present invention releases the unmodified physiologically active substance through the cleavage of the glycosylated linker moiety under predetermined conditions.

Preferably, the glycosylated linker of the present invention has no adverse effect on the pharmacokinetic, immunogenic, toxicological, or pharmacological properties, etc., of its binding partner physiologically active substance.

In the present specification, the "physiologically active substance" is not limited and means a substance that has a certain effect or influence either directly or indirectly on the physiological activity of an organism. The physiologically active substance may be intended to be used in vitro and in vivo. The physiologically active substance may exert no function in itself in vivo. In a certain embodiment, the physiologically active substance may be used interchangeably with a drug. The physiologically active substance may include substances useful as vaccines or medicines as well as substances that have no direct effect or influence on the physiological activity of an organism, for example, diagnostic agents. Also, the physiologically active substance may include naturally occurring substances as well as partial deletion, modification, or substitution products (also referred to as derivatives) thereof. The physiologically active substance may further include artificially synthesized substances (e.g., substances produced by a biological approach such as recombinant DNA technology or by a chemical synthetic approach such as a solid-phase peptide synthesis method) and fusion products of a portion of a naturally occurring substance and a portion of an artificially synthesized substance. Thus, the physiologically active substance according to the present invention also includes substances fused with, for example, a reporter protein such as GFP (green fluorescent protein) or a fluorescent dye such as fluorescein.

The physiologically active substance according to the present invention has at least one carboxy group. The physiologically active substance according to the present invention binds at the at least one carboxy group carried by the physiologically active substance to the glycosylated linker. The physiologically active substance according to the present invention is preferably a low-molecular physiologically active substance or a biopolymer having at least one carboxy group.

In the present specification, the "biopolymer" may mean a macromolecular organic compound among the physiologically active substances. On the other hand, the "low-molecular physiologically active substance" may mean a low-molecular organic compound among the physiologically active substances. The biopolymer may be, for example, a polymer compound such as a protein, a nucleic acid, or a polysaccharide, or a portion thereof, or may be artificially synthesized. The low-molecular physiologically active substance may be, for example, a substance that can interact with the biopolymer in vivo, or may be artificially synthesized. In the present specification, however, the biopolymer and the low-molecular physiologically active substance may be the same as each other in some cases.

According to one embodiment, preferably, the biopolymer according to the present invention is a protein, a polypeptide, a polynucleotide, or a peptide nucleic acid having at least one carboxy group, or contains the "protein, polypeptide, polynucleotide, or peptide nucleic acid" in a portion of its structure. In the present specification, the portion derived from the protein or the polypeptide is also referred to as a "peptide moiety".

In the present specification, the "protein" is not particularly limited as long as the protein is composed of a plurality of amino acids joined through amide bonds. The protein includes known proteins, novel proteins, or their variants. In the present specification, the "variant" is a naturally or artificially partially altered compound of the protein. Examples of such alteration include alkylation, acylation (e.g., acetylation), amidation (e.g., C-terminal amidation of the protein), carboxylation, esterification, disulfide bond formation, glycosylation, lipidation, phosphorylation, hydroxylation, dehydration condensation, or labeling component bonding of one or more amino acid residues in the protein. Alternatively, examples of the variant include partial deletion, substitution, or fusion products of the structures of known proteins or novel proteins. When the biopolymer as the physiologically active substance is a protein, the protein may be synthesized by use of, but not limited to, a method generally known to those skilled in the art, for example, solid-phase synthesis, liquid-phase synthesis, cell-based synthesis, or separation and extraction of a naturally occurring protein.

In the present specification, the "polypeptide" and the "peptide" are used interchangeably with the protein, as a rule. However, the polypeptide and the peptide may be used to represent a portion of the structure of the protein or to represent a relatively short amino acid chain without assuming a higher order structure (a fragment of the protein). The polypeptide or the peptide according to the present invention may also include, for example, dipeptide composed of 2 amino acids joined, tripeptide composed of 3 amino acids joined, tetrapeptide composed of 4 amino acids joined, and oligopeptide typically composed of 10 or less amino acids joined.

In the present specification, the "polynucleotide" includes, but is not limited to: single- or double-stranded DNA or RNA having 2 to 2000 nucleotide residues; single- or double-stranded siRNA, miRNA, or nucleic acid (DNA or RNA) aptamers; and chemically modified compounds thereof. Examples of such modification include, but are not limited to, modification with other chemical groups that further impart electric charge, polarizability, hydrogen bond, electrostatic interaction, or fluxionality to the whole or a portion of the polynucleotide. The polynucleotide may be an oligonucleotide having 20 base pairs or a smaller size.

In the present specification, the "peptide nucleic acid" is not limited and means a modified nucleic acid having a N-(2-aminoethyl)glycine backbone converted from the sugar phosphate backbone of a nucleic acid (DNA or RNA). The peptide nucleic acid may be further modified by a method generally known to those skilled in the art.

According to one embodiment, the biopolymer according to the present invention includes, but is not limited to, for example, adrenocorticotropic hormone (ACTH), oxytocin, adenosine deaminase, agalsidase, al antitrypsin, al protease inhibitor, alteplase, amylin, Symlin, anistreplase, ancrod serine protease, antithrombin III, antitrypsin, aprotinin, asparaginase, atosiban, biphalin, bivalirudin, bone morphogenetic protein, pancreatic trypsin inhibitor, cadherin fragment, calcitonin (e.g., salmon-derived), collagenase, complement C1 esterase inhibitor, conotoxin, cytokine receptor fragment, DNase, dynorphin A, endorphin, enfuvirtide, enkephalin, erythropoietin, exendin (exendin-3 or exendin-4, etc.), factor VII, factor VIIa, factor VIII, factor VIIIa, factor IX, fibrinolysin, fibroblast growth factor (FGF), growth hormone-releasing peptide 2 (GHRP-2), follicle-stimulating hormone, gramicidin, ghrelin, desacyl ghrelin, granulocyte colony-stimulating factor (G-CSF), galactosidase, glucagon, glucagon-like peptide (exenatide, GLP-1, GLP-2, etc.), glucocerebrosidase, granulocyte macrophage colony-stimulating factor (GM-CSF), heat shock protein (HSP), phospholipase-activating protein (PLAP), chorionic gonadotropin, hemoglobin, hirudin, human serine protease inhibitor, hyaluronidase, iduronidase, immunoglobulin (IgG Fc region, etc.), interleukin (1α, 1β, 2, 3, 4, 5, 7, 8, 9, 10, 11, 12, 13, 14, 15, 17, 18, or 21, etc.), IL-1 receptor antagonist (IL-1ra), insulin, insulin-like growth factor, insulin-like growth factor-binding protein (IGFBP), interferon (α (α2a, α2b, α2c, etc.), β (β1a and β1b), γ (γ1a and γ1b), λ, ω, ε, κ, etc.), intracellular adhesion molecule, keratinocyte growth factor (KGF), P-selectin glycoprotein ligand (PSGL), transforming growth factor, lactase, leptin, leuprolide, luteinizing hormone, natriuretic peptide (ANP, BNP, or CNP, or fragments thereof), neuropeptide Y, pancrelipase, pancreatic polypeptide, papain, parathyroid hormone (parathormone, etc.), platelet-derived growth factor (PDGF), pepsin, peptide YY, platelet-activating factor acetylhydrolase (PAF-AH), prolactin, protein A, protein C, thymosin al, octreotide, selectin, sermorelin, soluble tumor necrosis factor receptor, superoxide dismutase (SOD), somatropin (growth hormone), somatoprim, somatostatin, streptokinase, sucrase, terlipressin, tetanus toxin C fragment, tilactase, thrombin, thymosin, thyroid-stimulating hormone, thyrotropin, tumor necrosis factor (TNF), TNF receptor, tissue plasminogen activator (tPA), thyroid hormone (calcitonin, etc.), urodilatin, urate oxidase, urokinase, hapten, vaccines containing antigens or the like (cancer vaccines, HIV antigens, hepatitis A vaccines, hepatitis B vaccines (HBs antigens, etc.), influenza vaccines, Lyme disease vaccines, etc.), vascular endothelial growth factor (VEGF), chemerin), HER2 protein (human epithelial growth factor receptor), epithelial growth factor (EGF), vasoactive intestinal peptide, vasopressin, ziconotide, lectin, choline esterase, amylase, and pepsin, and variants thereof, and fragments thereof.

According to one embodiment, examples of the low-molecular physiologically active substance according to the present invention include central nervous system stimulants, anti-infective agents, anti-allergic agents, immune-regulating agents, anti-obesity agents, anticoagulants, antidiabetic agents, anticancer agents, antineoplastic agents, antimicrobial agents, antimycotic agents, analgesics, contraceptives, anti-inflammatory agents, steroids, vasodilators, vasoconstrictors, and cardiovascular agents having at least one carboxy group.

According to one embodiment, the low-molecular physiologically active substance according to the present invention includes, but is not limited to, for example, acarbose, alaproclate, alendronate, amantadine, amikacin, amineptine, aminoglutethimide, amisulpride, amlodipine, amotosalen, amoxapine, amoxicillin, amphetamine, amphotericin B, ampicillin, amprenavir, amrinone, anileridine, apraclonidine, apramycin, articaine, atenolol, atomoxetine, avizafone, baclofen, benazepril, benserazide, benzocaine, betaxolol, bleomycin, bromfenac, brofaromine, carvedilol, cathine, cathinone, carbutamide, cephalexin, clinafloxacin, ciprofloxacin, deferoxamine, delavirdine, desipramine, daunorubicin, dexmethylphenidate, dexmethylphenidate, diaphenylsulfone, dizocilpine, dopamine, dobutamine, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecainide, fluvoxamine, fosamprenavir, frovatriptan, furosemide, fluoxetine, gabapentin, gatifloxacin, gemifloxacin, gentamycin, grepafloxacin, hexylcaine, hydralazine, hydrochlorothiazide, icofungipen, idarubicin, imiquimod, isoproterenol, isradipine, kanamycin A, ketamine, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantrone, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazine, sulfamerazine, sertraline, spectinomycin, sulfalene, sulfamethoxazole, tacrine, tamsulosin, terbutaline, timolol, tirofiban, tobramycin, tocainide, tosufloxacin, trandolapril, tranexamic acid, tranylcypromine, trimetrexate, trovafloxacin, valaciclovir, valganciclovir, vancomycin, viomycin, viloxazine, zalcitabine, penicillin, cephalosporin, streptomycin, destomycin, kasugamycin, tylosin, erythromycin, oleandomycin, spiramycin, lincomycin, colistin, bacitracin, salinomycin, monensin, lasalocid, tetracycline, chloramphenicol, virginiamycin, sulfadimethoxine, oxolinic acid, piromidic acid, difurazone, zearalenone, deoxynivalenol, patulin, fumonisin, ochratoxin, tetrodotoxin, okadaic acid, saxitoxin, and gonyautoxin.

The compound of the present invention in which a glycosylated linker and a physiologically active substance are bonded to each other can be produced by bonding the physiologically active substance to the glycosylated linker synthesized and isolated by the method mentioned above.

The bonding between the glycosylated linker and the physiologically active substance is achieved via an ester bond or a thioester bond through the condensation reaction of the oxygen atom (O) having a leaving group or the sulfur atom (S) having a leaving group in the glycosylated linker with at least one carboxy group of the physiologically active substance.

The conditions for this condensation reaction can be appropriately set by those skilled in the art. For example, a condensing agent such as PyBOP, DMAP, or HCTU can be used in the condensation reaction. For example, a solvent such as DMF, DMSO, or dichloromethane can also be used in the condensation reaction. The condensation reaction can be carried out, for example, by dissolving a peptide with protected amino acid side chains and a glycosylated linker having a thiol group in DMF and adding PyBOP and DIPEA to the solution. When the physiologically active substance is a peptide, this reaction is preferably carried out at a low temperature (−15° C. to −30° C.) because the isomerization of the C-terminal amino acid of the peptide can be suppressed.

When the physiologically active substance is a peptide, each side chain of the peptide is preferably protected with a protective group. The protective group with which the side chain of the peptide is protected can be deprotected after the bonding between the glycosylated linker and the peptide. A protective group well known to those skilled in the art can be used for protecting the side chain of the peptide, and, for example, the protective group for the amino acid used in the solid-phase synthesis mentioned above can be used. Those skilled in the art can appropriately carry out the introduction of the protective group to the peptide and its deprotection.

When the physiologically active substance is a polypeptide or the like, amino acids, etc., constituting the physiologically active substance can be sequentially bonded directly to the glycosylated linker bonded on the resin during the solid-phase synthesis to produce the compound comprising a glycosylated linker moiety and a physiologically active substance moiety. The reaction conditions for synthesizing the physiologically active substance moiety by the solid-phase synthesis method on the resin can be appropriately set by those skilled in the art.

According to one embodiment, the present invention preferably provides a compound or a salt thereof obtainable by any of the production methods mentioned above. The obtainable compound or salt thereof is not limited to those produced by any of the production methods mentioned above and also includes those produced by other production methods.

According to another embodiment, the present invention preferably provides a compound or a salt thereof obtained by any of the production methods mentioned above.

According to a preferred embodiment, by use of the glycosylated linker of the present invention, a physiologically active substance can be readily dissolved, as the "compound comprising a glycosylated linker moiety and a physiologically active substance moiety, or the salt thereof", in an aqueous solution or an emulsion prepared from the aqueous solution, regardless of whether or not the physiologically active substance is poorly soluble. After the dissolution, the glycosylated linker moiety can be cleaved to release the unmodified physiologically active substance.

The glycosylated linker moiety according to the present invention is cleaved through hydrolysis reaction from the "compound comprising a glycosylated linker moiety and a physiologically active substance moiety, or the salt thereof". According to a preferred embodiment, the glycosylated linker moiety may be cleaved by autohydrolysis from the "compound comprising a glycosylated linker moiety and a physiologically active substance moiety, or the salt thereof" through its intramolecular catalysis. However, the cleavage is not intended to exclude, for example, biological cleavage such as cleavage by an enzyme present in vivo (e.g., examples of the enzyme include esterase that cleaves an ester bond).

According to a preferred embodiment, a feature of the compound of the present invention or the salt thereof is that after the dissolution in an aqueous solution or an emulsion, the cleavage of the glycosylated linker moiety is accelerated in a manner dependent on pH and/or temperature (pH- and/or temperature-dependent cleavage). The compound of the present invention or the salt thereof and the glycosylated linker of the present invention may be preserved, for example, at a low temperature (e.g., −80° C. to 4° C.) and/or a low pH (e.g., pH 1 to pH 4). The step of preparing the "compound comprising a glycosylated linker moiety and a physiologically active substance moiety, or the salt thereof" by bonding the physiologically active substance to the glycosylated linker moiety may be carried out, for example, at a low temperature (e.g., 0° C. to 25° C.) and/or a low pH (e.g., pH 1 to pH 7). The "compound comprising a glycosylated linker moiety and a physiologically active substance moiety, or the salt thereof" and the glycosylated linker may be stabilized by the protection of the N-terminal amino group of the glycosylated amino acid with a protective group such as a $C_1$-$C_{16}$ acyl group, an Fmoc group, or an Alloc group.

Preferably, the compound of the present invention or the salt thereof may be used at a temperature and a pH close to physiological conditions (e.g., the in vivo physiological environment of a mammal or a similar environment, for example, 35° C. to 43° C. and pH 6.8 to 7.8).

According to a preferred embodiment, by use of the compound of the present invention or the salt thereof, the physiologically active substance can be efficiently dissolved in an aqueous solution or an emulsion prepared from the aqueous solution. Thus, according to a preferred embodiment, by use of the compound of the present invention or the salt thereof, even a low water-soluble (poorly soluble) physiologically active substance can be filter-sterilized. According to a preferred alternative embodiment, by use of the compound of the present invention or the salt thereof, even a low water-soluble physiologically active substance can be administered to an organism.

According to a preferred alternative embodiment, by use of the compound of the present invention or the salt thereof, even a highly water-soluble physiologically active substance can be dissolved with higher efficiency in an aqueous solution or an emulsion prepared from the aqueous solution. Thus, advantageously, the present invention reduces "losses" that may be caused by the insolubility, etc., of a substance in the course of preparing a preparation containing an expensive physiologically active substance or administering such a preparation.

According to a preferred alternative embodiment, the glycosylated linker of the present invention having a known half-life in a solvent can be appropriately selected, thereby controlling the release duration and timing of the unmodified physiologically active substance to be released into an in vitro environment or an in vivo environment. The glycosylated linker of the present invention is also advantageous to the delivery of, for example, a physiologically active substance desired to exert its effects immediately at the desired site after administration to an organism.

According to a particularly preferred embodiment, the "compound comprising a glycosylated linker moiety and a physiologically active substance moiety, or the salt thereof" according to the present invention can provide improved water solubility compared with an unmodified physiologically active substance. The improved water solubility is preferably 2 times to 1,000,000 times, more preferably 10 times to 1,000,000 times, further preferably 100 times to 1,000,000 times, still further preferably 500 times to 1,000,000 or more times the water solubility of the unmodified physiologically active substance in terms of molar concentration. Those skilled in the art can appropriately select the "compound comprising a glycosylated linker moiety and a physiologically active substance moiety, or the salt thereof" or the glycosylated linker having necessary water solubility according to the use and purpose of the physiologically active substance.

The molar absorption coefficient (specific absorbance) necessary for determining the solubility of the "compound comprising a glycosylated linker moiety and a physiologically active substance moiety, or the salt thereof" according to the present invention, or the unmodified physiologically active substance may be determined by ultraviolet-visible spectroscopy (e.g., a wavelength in the ultraviolet-visible region, such as 280 nm) using, as a sample, a solution having a known protein concentration measured by a method generally known to those skilled in the art, for example, an amino acid composition analysis method or a nitrogen quantification method.

According to one aspect, the present invention also provides a composition comprising the compound comprising a glycosylated linker moiety and a physiologically active substance moiety, or the salt thereof.

The "composition" of the present invention comprises one or more compounds of the present invention or salts thereof and optionally contains one or more additional components (active and/or inert ingredient(s)). The composition of the present invention is not particularly limited by its use and may be used in, for example, an assay system (e.g., an in vitro assay system).

According to one embodiment of the present invention, the sugar chain structure of the glycosylated linker moiety can be homogeneous, as described above. In this case, preferably, the glycosylated linker moiety contained in the composition comprising the compound comprising this glycosylated linker moiety and a physiologically active substance moiety, or the salt thereof is not only homogeneous in sugar chain structure but also in its whole structure. "The structure of the glycosylated linker moiety are homogeneous" means that the glycosylation site in the glycosylated linker moiety, the type of each sugar constituting the sugar chain, the binding order of the sugar chain, the binding pattern between sugars, and the structure constituting the linker moiety are identical among glycosylated linker moieties contained in the composition(s) when sugar chains and linker moieties are compared among these glycosylated linker moieties. Specifically, "the structure of the glycosylated linker moiety are homogeneous" means that at least 90% or more, preferably 95% or more, more preferably 99% or more sugar chain structures and linker moieties are uniform among the glycosylated linker moieties contained in the composition(s).

Particularly, the composition or the like comprising the glycosylated linker moiety in which sugar chains are homogeneous has constant quality and is particularly preferred in the field of the production of medicines, assays, etc. The ratio of homogeneous sugar chains or the ratio of homogeneously glycosylated linkers can be measured by a method using, for example, HPLC, capillary electrophoresis, NMR, or mass spectrometry.

The "pharmaceutical composition" of the present invention is a composition suitable for medical uses and is formulated in the form of an ordinary pharmaceutical composition using diluents or excipients usually used, such as a filler, an expander, a binder, a wetting agent, a disintegrant, a surfactant, and a lubricant. Examples of such a pharmaceutical composition include, but are not limited to, tablets, pills, powders, solutions, suspensions, emulsions, granules, capsules, suppositories, and injections. The medical uses of the pharmaceutical composition may target diseases or disorders involving a physiologically active substance contained as the physiologically active substance moiety in the composition. When the physiologically active substance is, for example, GLP-1 or its derivative, the medical uses may target diabetes mellitus or the like. Those skilled in the art can similarly understand other medical uses, also in view of the types of diseases or disorders involving each physiologically active substance.

In the present specification, the "pharmacologically acceptable carrier" is not particularly limited. The addition of the pharmacologically acceptable carrier may influence the absorbability or concentration in blood of the "compound comprising a glycosylated linker moiety and a physiologically active substance moiety, or the salt thereof" according to the present and cause change in its disposition.

Particularly preferably, when an antigen is used as the physiologically active substance, the compound of the present invention or the salt thereof and the pharmaceutical composition of the present invention comprising the same may be used as a vaccine. According to a preferred embodiment, for example, even a poorly soluble antigen can be dissolved, as the compound of the present invention or the salt thereof, in an aqueous solution or an emulsion. In addition, the unmodified antigen can be released after cleavage of the glycosylated linker moiety in vivo. Preferably, the compound of the present invention or the salt thereof and the glycosylated linker of the present invention can be used in the development of various vaccines such as peptide vaccines.

In the present specification, the "vaccine" (also called "immunogenic composition") means a substance capable of causing immune response when inoculated into an animal. The vaccine may contain an antigen or may express the antigen, thereby inducing immune response against the antigen. The pharmaceutical composition of the present invention used as a vaccine can be used not only in the prevention or treatment of viral infections, bacterial infections (sepsis, etc.), and communicable diseases but in the treatment, etc., of any disease that may be related to immune response, for example, cancers and autoimmune diseases (e.g., type I diabetes mellitus, multiple sclerosis, and articular rheumatism).

The "antigen" is a molecule containing one or more epitopes and can be any molecule capable of inducing antigen-specific immune response by stimulating the immune system of a host. The immune response may be humoral immune response and/or cellular immune response. Although approximately 3 to several (e.g., 5 or 6) amino acids may serve as one epitope, one epitope in a protein typically contains 7 to 15 amino acids, for example, 8, 9, 10, 12, or 14 amino acids. According to one embodiment, the antigen is preferably a peptide or an epitope. When the antigen is used in the treatment of cancers, such a peptide is also called cancer peptide.

Also, the pharmaceutical composition of the present invention (including that for use as a vaccine) may be administered to an organism. The pharmaceutical composition of the present invention is not particularly limited by its administration method and is administered by a method suitable for various dosage forms, the age, sex, and disease severity of a patient, and other conditions. Examples of methods for administering tablets, pills, solutions, suspensions, emulsions, granules, and capsules include oral administration. Alternatively, an injection can be administered either alone or as a mixture with an ordinary fluid replacement such as glucose or an amino acid through an intravenous, intramuscular, intracutaneous, subcutaneous, or intraperitoneal route. A suppository is administered into the rectum. Particularly, the pharmaceutical composition of the present invention used as a vaccine may be administered through subcutaneous injection, intramuscular injection, an oral route, a stump form, intracutaneous injection, or the like.

The dose of the pharmaceutical composition of the present invention (including that for use as a vaccine) can be appropriately selected according to the usage, the age, sex, and disease severity of a patient, and other conditions. The frequency of administration can be appropriately selected according to the usage, the age, sex, and disease severity of a patient, and other conditions. For example, 3 times/day, twice/day, once/day, or less frequent administration (e.g., once/week or once/month) according to the stability thereof in blood may be selected. The pharmaceutical composition of the present invention may confer sustained release properties to the physiologically active substance by gradual cleavage of the sugar chain linker moiety. Alternatively, the pharmaceutical composition of the present invention may confer fast acting properties to the physiologically active substance by rapid cleavage of the sugar chain linker moiety.

In a certain aspect, the present invention also relates to use of the glycosylated linker or the "compound comprising a glycosylated linker moiety and a physiologically active substance moiety, or the salt thereof" for the production of a therapeutic or preventive drug for diseases or disorders targeted by a physiologically active substance. In an alternative aspect, the present invention also relates to use of the glycosylated linker or the "compound comprising a glycosylated linker moiety and a physiologically active substance moiety, or the salt thereof" for the treatment or prevention, etc., of diseases or disorders targeted by a physiologically active substance. When the physiologically active substance is, for example, HER2 or its derivative, the targeted disease may be cancer or the like (e.g., breast cancer). Those skilled in the art can similarly understand the types of diseases or disorders targeted by each of other physiologically active substances.

The glycosylated linker of the present invention configured to contain an added sugar chain having biodegradable nature has a reduced adverse effect on organisms compared with a linker configured to contain added PEG. As a result, long-term administration as a pharmaceutical composition to organisms is expected.

In the present specification, the aqueous solution may be any liquid of a substance (e.g., acetate) dissolved in water as a solvent and includes every aqueous solution generally known to those skilled in the art and every novel aqueous solution.

In the present specification, the emulsion is not limited and may be any preparation from the aqueous solution. The emulsion may be an oil-in-water (O/W) emulsion or a water-in-oil (W/O) emulsion, though there is no limitation. Methods generally known to those skilled in the art may be used as methods for dispersion and emulsification in the aqueous solution.

The "subject" to which the compound of the present invention or the salt thereof, or the pharmaceutical composition of the present invention is administered (applied) includes, but is not limited to, animals (humans, nonhuman mammals (e.g., mice, rats, dogs, cats, rabbits, cattle, horses, sheep, goats, and pigs), and non-mammalian animals (e.g., fish, reptiles, amphibians, and bird)), plants, insects, bacteria, and cells derived therefrom(including cultured cells), tissues, and organs, etc. Alternatively, the "subject" may be an artificial environment (e.g., an in vitro reaction system). Preferably, the "subject" according to the present invention is a human.

The term "aspect" or "embodiment" (e.g., "one aspect", "one embodiment", or "another embodiment") used in the present specification indicates a preferred profile of the present invention and is not intended to limit the scope of the present invention to the predetermined aspect or embodiment. Those skilled in the art should naturally understand that every combination of the aforementioned aspects and embodiments of the present invention is possible unless there is a technical contradiction. Those skilled in the art understand that, for example, every combination of substituents is disclosed in an aspect or an embodiment unless there is a technical contradiction.

The terms used in the present specification are given for illustrating particular embodiments and are not intended to limit the present invention.

The term "comprising" used in the present specification means that described items (members, steps, factors, numbers, etc.) are present, and does not exclude the presence of the other items (members, steps, factors, numbers, etc.), unless the context evidently requires different interpretation.

All terms (including technical terms and scientific terms) used herein have the same meanings as those understood in a broad sense by those skilled in the art to which the present invention belongs, unless otherwise defined. The terms used herein should be interpreted as having meanings consistent with meanings in the present specification and related technical fields and should not be interpreted in an idealized or excessively formal sense, unless otherwise defined.

The embodiments of the present invention may be described with reference to a schematic diagram. However, such a schematic diagram may be exaggerated for the purpose of clear illustration.

The terms such as "first" or "second" are used for expressing various factors. However, these terms are understood to be not limited by these terms. These terms are used merely for differentiating one factor from the other factors. For example, the first factor may be described as the second factor, and vice versa, without departing from the scope of the present invention.

Hereinafter, the present invention will be described in more detail with reference to Examples. However, the present invention can be embodied in various aspects and must not be interpreted as being limited to Examples described herein.

EXAMPLES

Some abbreviations used in Examples will be described below:

Ac: Acetyl (group)
AcOH: Acetic acid
Asn: Asparagine
Boc: tert-Butyloxycarbonyl group
BrAc: Bromoacetamide
Cys: Cysteine
DIC: Diisopropylcarbodiimide
DIPEA: N,N-Diisopropylethylamine
DMAP: 4-Dimethylaminopyridine
DMF: N,N-Dimethylformamide
DMSO: Dimethyl sulfoxide
DTT: Dithiothreitol
ESI-MS: electrospray ionization mass spectrometry
Fmoc (group): 9-Fluorenylmethyloxycarbonyl (group)
HCL: Hydrochloric acid
HCTU: O-(6-Chloro-1H-benzotriazol-1-yl)-N,N,N',N'-tetramethyluronium hexafluorophosphate
HMPB: 4-Hydroxymethyl-3-methoxyphenoxy-butyric acid
HMBA: 4-Hydroxymethyl-benzoic acid
HOBt: 1-Hydroxybenzotriazole
HPLC: High-performance liquid chromatography
$H_2O$: Water
MSNT: 1-(Mesitylene-2-sulfonyl)-3-nitro-1,2,4-triazole(1-(Mesitylene-2-sulfonyl)-3-nitro-1,2,4-triazole)
PBS: Phosphate-buffered saline
Pbf: 2,2,4,6,7-Pentamethyldihydrobenzofuran-5-sulfonyl
SPPS: Solid-phase peptide synthesis
tBu: tert-Butyl group
TFA: Trifluoroacetic acid
Trt: Trityl group In Examples below, a compound in which a glycosylated linker and a physiologically active substance are bonded to each other is referred to as a conjugate. For example, a conjugate in which a glycosylated linker having an asialo sugar chain at cysteine in the linker is bonded to a portion of a physiologically active substance HER2 (portion containing the 8th to 16th amino acids in the amino acid sequence of HER) is referred to as a glycosylated (Cys (asialo)-type) linker-HER2(8-16) conjugate.

HER2(8-16) is a peptide corresponding to the 8th to 16th amino acid residues in the amino acid sequence of the HER2/neu protein, which is a member of the HER (human epidermal growth factor receptor) family. This HER2(8-16) has the ability to bind to HLA-A24, one of HLA (human leukocyte antigen) molecules, and exhibits the ability to induce cytotoxic T lymphocyte (CTL) by HLA-mediated antigen presentation, and this peptide fragment has been identified as a tumor vaccine candidate peptide (Tanaka, H., et al., Brit. J. Cancer, 84 (1), 94-99, 2001).

(Example 1-1: Synthesis of Glycosylated (Cys (Asialo)-Type) Linker-HER2(8-16) Conjugate (Compound 1))
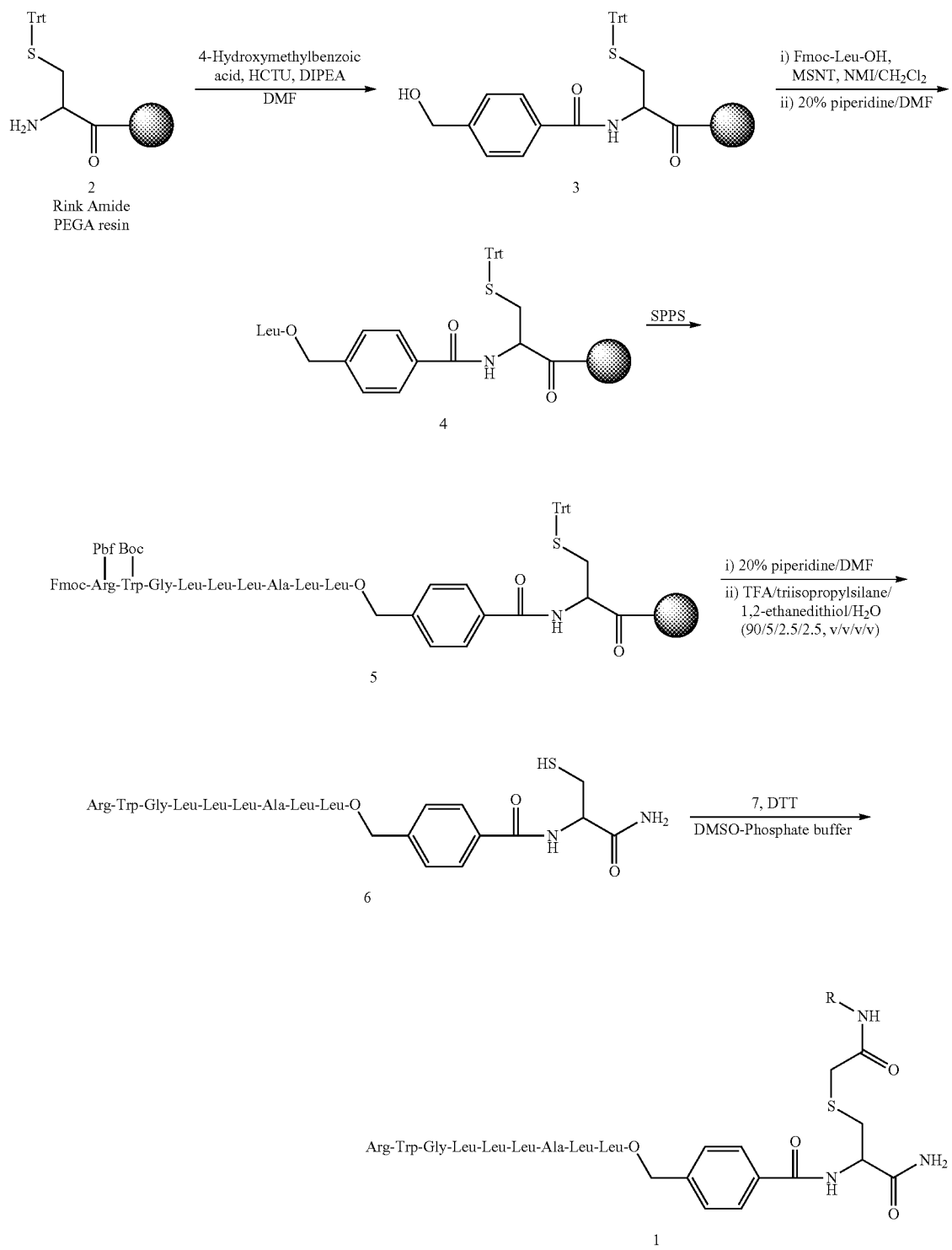

wherein R represents the following chemical formula:
[Formula 31]

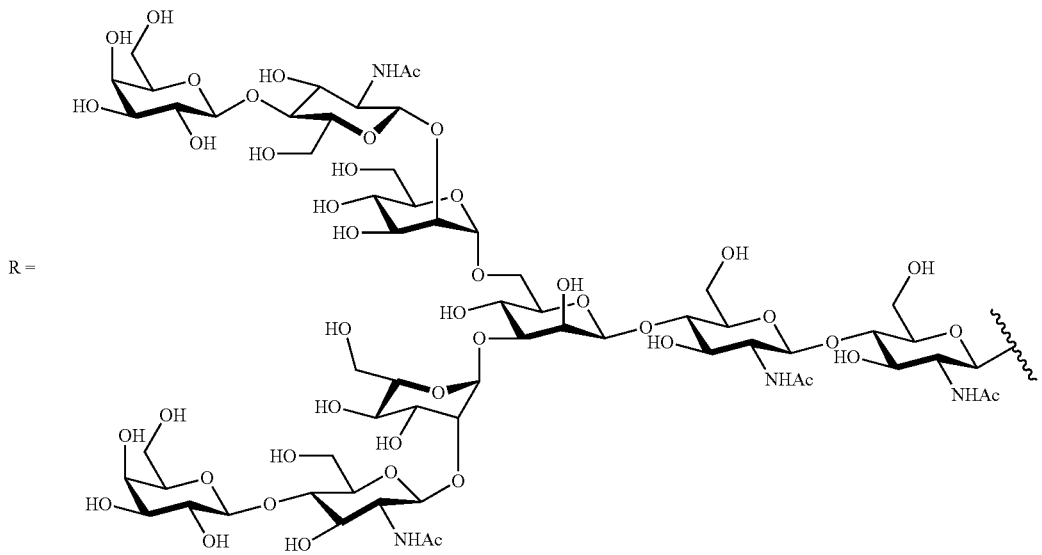

Rink-Amide-PEGA resin (100 µmol) was placed in a column for solid-phase synthesis and washed with dichloromethane and DMF. After the washing, a DMF (2.5 mL) solution containing Fmoc-Cys(Trt)-OH (234 mg, 0.399 mmol), HCTU (157 mg, 0.380 mmol), and 2,4,6-trimethylpyridine (79.6 µL, 0.600 mmol) was added thereto, and the mixture was shaken at room temperature for 10 minutes. After 10 minutes, the resin was washed with DMF, and this condensation operation was then repeated once again. After the completion of the second condensation operation, the resin was washed with DMF and dichloromethane. After the washing, the Fmoc protective group was removed by treatment with 20% piperidine in DMF to obtain resin 2 bonded to Cys(Trt). The resin 2 was washed with DMF. Then, a DMF (2.5 mL) solution of 4-hydroxymethyl-benzoic acid (61.1 mg, 0.402 mmol), HCTU (157.8 mg, 0.381 mmol), and DIPEA (104.5 µL, 0.600 mmol) was added thereto, and the mixture was shaken at room temperature. After 1 hour, the resin was washed with DMF and dichloromethane to obtain compound 3 bonded to HMBA-Cys(Trt) on the resin.

An aliquot of the resin bonded to the compound 3 (100 µmol) was placed in a column for solid-phase synthesis. A dichloromethane (5.0 mL) solution containing Fmoc-Leu-OH (176.7 mg, 0.500 mmol), MSNT (148.2 mg, 0.500 mmol), and N-methylimidazole (27.9 µL, 0.350 mmol) was added thereto, and the mixture was shaken at room temperature for 1 hour. After the shaking for 1 hour, the resin was washed with dichloromethane and DMF. After the washing, the Fmoc protective group was removed by treatment with 20% piperidine in DMF to obtain Leu-HMBA-Cys(Trt) 4 on the resin. After washing with DMF, compound 5: Fmoc-Arg(Pbf)-Trp(Boc)-Gly-Leu-Leu-Leu-Ala-Leu-Leu-HMBA-Cys(Trt) (SEQ ID NO: 1) was synthesized on the resin by a solid-phase peptide synthesis method according to the Fmoc method using a Prelude (trademark) peptide synthesizer. The condensation reaction in the solid-phase synthesis method was carried out in DMF using HCTU as a condensing agent and N-methylmorpholine as a base.

The Fmoc protective group on the compound 5 was removed by treatment with 20% piperidine in DMF. The resin was washed with DMF and dichloromethane. Then, TFA:triisopropylsilane:ethanedithiol:water (=90:5:2.5:2.5) was added thereto, and the mixture was shaken at room temperature for 3 hours. To the filtrate, cooled ether was added to obtain crude peptide 6: Arg-Trp-Gly-Leu-Leu-Leu-Ala-Leu-Leu-HMBA-Cys (SEQ ID NO: 2) as precipitates.

The obtained crude peptide 6 (15.5 mg) was dissolved in a DMSO-0.1 M phosphate buffer solution (pH 7.4) mixed solution (9/1, v/v, 240 µL) containing 50 mM DTT. To the solution, a DMSO-0.1 M phosphate buffer solution (pH 7.4) mixed solution (9/1, v/v, 946 µL) containing 30 mM asialo-BrAc 7 dissolved therein was added thereto, and the mixture was shaken at room temperature for 2 hours.

[Formula 32]

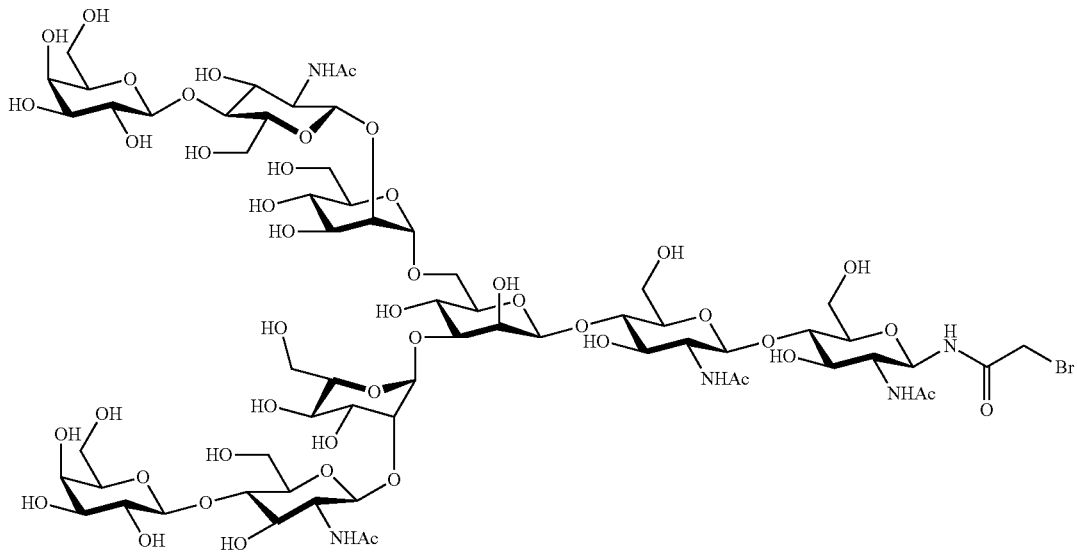

7

The reaction solution was purified by HPLC [column: SHISEIDO CAPCELL PAK C18 UG-120 (5 μm), φ20×250 mm, flow rate: 7.0 mL/min, eluent A: 0.1% TFA in water, eluent B: 0.09% TFA/10% water/90% acetonitrile, gradient A:B=60:40→40:60 (20 min) linear concentration gradient elution] to obtain a fraction containing a glycosylated (Cys (asialo)-type) linker-HER2(8-16) conjugate (compound 1): Arg-Trp-Gly-Leu-Leu-Leu-Ala-Leu-Leu-(sugar chain added-linker: HMBA-Cys (asialo)) (SEQ ID NO: 3).

This fraction was further purified by HPLC [column: SHISEIDO CAPCELL PAK C18 UG-120 (5 μm), φ20×250 mm, flow rate: 7.0 mL/min, eluent A: 0.1% AcOH in water, eluent B: 0.09% AcOH/10% water/90% acetonitrile, gradient A:B=75:25→60:40 (30 min) linear concentration gradient elution] to obtain a glycosylated (Cys (asialo)-type) linker-HER2(8-16) conjugate (compound 1) (17.2 mg, 5.79 μmol).

ESI-MS calcd for $C_{127}H_{204}N_{20}O_{58}S$ $[M+2H]^{2+}$ 1485.7, $[M+3H]^{3+}$ 990.8, $[M+4H]^{4+}$ 743.3. found 1485.7, 990.8, 743.3.

Example 1-2: Synthesis of Glycosylated (Cys (Disialo)-Type) Linker-HER2(8-16) Conjugate (Compound 8)

[Formula 33A]

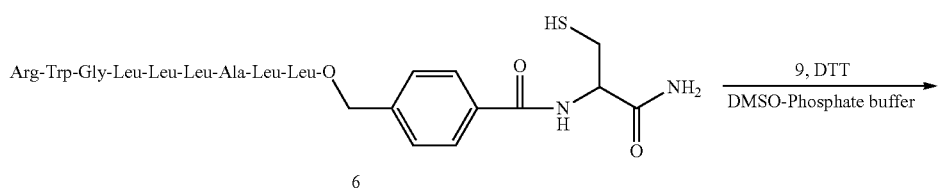

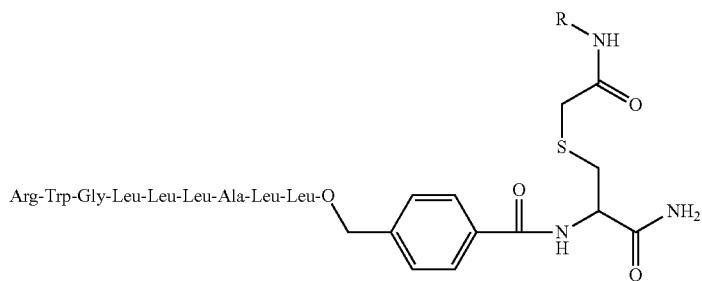

wherein R represents the following chemical formula:

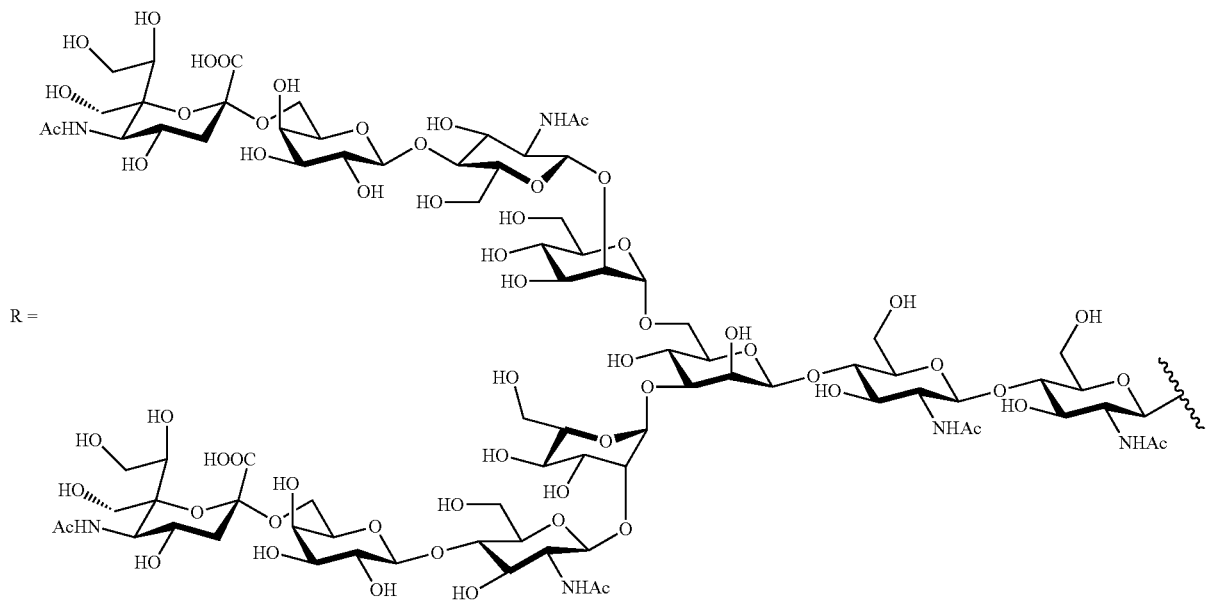

[Formula 33B]

The crude peptide 6 (15.5 mg) obtained in Example 1-1 was dissolved in a DMSO-0.1 M phosphate buffer solution (pH 7.4) mixed solution (9/1, v/v, 240 μL) containing 50 mM DTT. To this mixed solution, a DMSO-0.1 M phosphate buffer solution (pH 7.4) mixed solution (9/1, v/v, 3.8 mL) containing 7.5 mM disialo-BrAc 9 was added, and the mixture was shaken at room temperature for 5 hours.

A:B=62:38→52:48 (30 min) linear concentration gradient elution] to obtain a fraction containing a glycosylated (Cys (disialo)-type) linker-HER2(8-16) conjugate (compound 8): Arg-Trp-Gly-Leu-Leu-Leu-Ala-Leu-Leu-(sugar chain added-linker: HMBA-Cys (disialo)) (SEQ ID NO: 4).

This fraction was further purified by HPLC [column: SHISEIDO CAPCELL PAK C18 UG-120 (5 μm), φ20×250

[Formula 34]

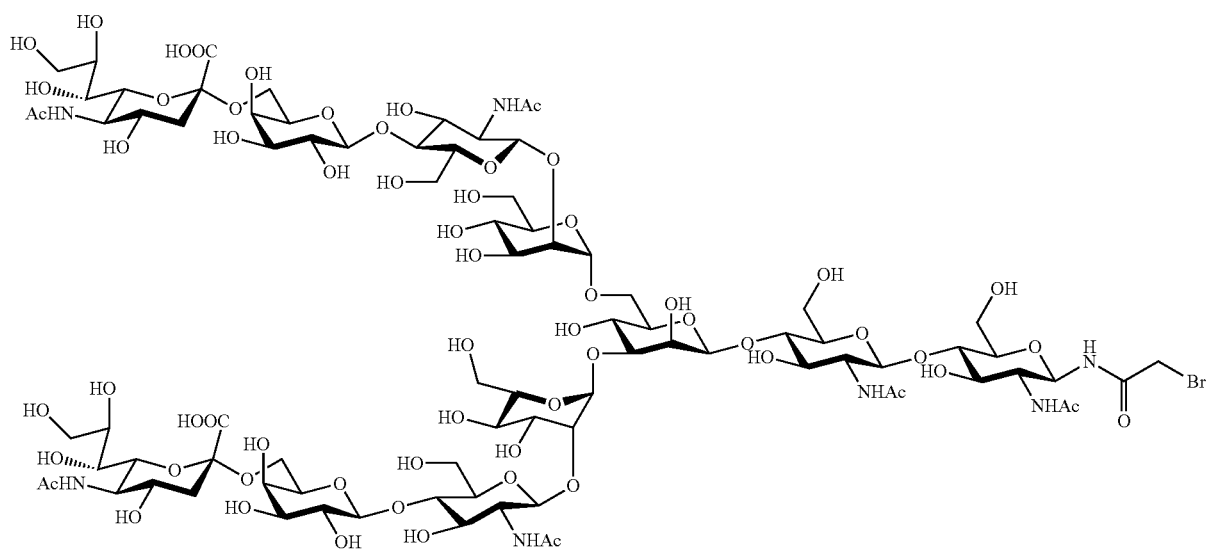

9

The reaction solution was purified by HPLC [column: SHISEIDO CAPCELL PAK C18 UG-120 (5 μm), φ20×250 mm, flow rate: 7.0 mL/min, eluent A: 0.1% TFA in water, eluent B: 0.09% TFA/10% water/90% acetonitrile, gradient mm, flow rate: 7.0 mL/min, eluent A: 0.1% AcOH in water, eluent B: 0.09% AcOH/10% water/90% acetonitrile, gradient A:B=70:30→50:50 (30 min) linear concentration gradient elution] to obtain a glycosylated (Cys (disialo)-type)

linker-HER2(8-16) conjugate (compound 8) (21.8 mg, 6.13 µmol).

ESI-MS calcd for $C_{149}H_{238}N_{22}O_{74}S$ $[M+2H]^{2+}$ 1776.8, $[M+3H]^{3+}$ 1184.8, $[M+4H]^{4+}$ 888.9. found 1776.8, 1184.8, 888.9.

Example 1-3: Solubility Measurement

Solubility in an aqueous solution was measured for the glycosylated (Cys (asialo)-type) linker-HER2(8-16) conjugate (compound 1) and the glycosylated (Cys (disialo)-type) linker-HER2(8-16) conjugate (compound 8) obtained in Examples 1-1 and 1-2, respectively, and an unmodified HER2(8-16) peptide (compound 10) having no glycosylated linker (Arg-Trp-Gly-Leu-Leu-Leu-Ala-Leu-Leu) (SEQ ID NO: 5).

Arg-Trp-Gly-Leu-Leu-Leu-Ala-Leu-Leu 10    [Formula 35]

More specifically, the test subject glycosylated (Cys (asialo)-type) linker-HER2(8-16) conjugate (compound 1), glycosylated (Cys (disialo)-type) linker-HER2(8-16) conjugate (compound 8), or unmodified HER2(8-16) peptide (compound 10) was collected in an amount of approximately 4.5 mg into a microtube, and 30 µL of water was added thereto. The microtube was shaken at 25° C. for 15 minutes and then centrifuged at 16100×g at 25° C. for 10 minutes. After the centrifugation, the absorbance of the supernatant portion at 280 nm was measured in the microtube. From the obtained value, the concentration was calculated to determine solubility. The molar absorption coefficients of the glycosylated (Cys (asialo)-type) linker-HER2(8-16) conjugate (compound 1) and the glycosylated (Cys (disialo)-type) linker-HER2(8-16) conjugate (compound 8) at 280 nm were determined by dividing the absorbance of the peptide chain moiety in the glycosylated (Cys (asialo)-type) linker-HER2 (8-16) conjugate (compound 1) or the glycosylated (Cys (disialo)-type) linker-HER2(8-16) conjugate (compound 8) at 280 nm by a concentration determined by amino acid analysis. The molar absorption coefficient ε280 of the unmodified peptide at 280 nm was calculated according to the following expression generally known to those skilled in the art:

$$\varepsilon_{280}(L \cdot mol^{-1} \cdot cm^{-1}) = n_{Trp} \times 5500 + n_{Tyr} \times 1490 + n_{SS} \times 125$$   [Mathematical 1]

wherein $n_{Trp}$ represents the number of tryptophan residues, $n_{Tyr}$ represents the number of tyrosine residues, and $n_{SS}$ represents the number of disulfide bonds. (Reference: C. N. Pace et al., Prot. Sci., 1995, 4, 2411-2423).

As a result, the HER2(8-16) peptide unbound with the glycosylated linker had a solubility of 0.22 mg/mL ($2.1 \times 10^2$ µM)) in water. In this respect, the precipitation of the HER2(8-16) peptide was able to be visually confirmed in the microtube. On the other hand, the glycosylated (Cys (asialo)-type) linker-HER2(8-16) conjugate (compound 1) was confirmed to have a solubility of 144 mg/mL or higher in water. Surprisingly, the precipitation of the glycosylated (Cys (asialo)-type) linker-HER2(8-16) conjugate (compound 1) was unable to be confirmed even at a concentration of 144 mg/mL. Also, the glycosylated (Cys (disialo)-type) linker-HER2(8-16) conjugate (compound 8) was confirmed to have a solubility of 121 mg/mL or higher in water. Surprisingly, the precipitation of the glycosylated (Cys (asialo)-type) linker-HER2(8-16) conjugate (compound 8) was unable to be confirmed even at a concentration of 121 mg/mL. These results demonstrated that the solubility of the glycosylated (Cys (asialo)-type) linker-HER2(8-16) conjugate (compound 1) and the glycosylated (Cys (disialo)-type) linker-HER2(8-16) conjugate (compound 8) in an aqueous solution is improved by 190 or more times the solubility of the unmodified HER2(8-16) peptide (compound 10) in terms of molar concentration (Table 1A).

TABLE 1A

Solubility of glycosylated linker-HER2(8-16) conjugate in water

| Sample | Solubility (µM) | Solubility (mg/mL) |
|---|---|---|
| Unmodified HER2(8-16) (compound 10) | $2.1 \times 10^2$ | 0.22 |
| Glycosylated (Cys (asialo)-type) linker-HER2(8-16) conjugate (compound 1) | $>4.1 \times 10^4$ | >144 |
| Glycosylated (Cys (disialo)-type) linker-HER2(8-16) conjugate (compound 8) | $>4.7 \times 10^4$ | >121 |

Solubility in a 0.1% aqueous acetic acid (AcOH) solution was further measured for the glycosylated (Cys (asialo)-type) linker-HER2(8-16) conjugate (compound 1), the glycosylated (Cys (disialo)-type) linker-HER2(8-16) conjugate (compound 8), and the unmodified HER2(8-16) peptide (compound 3) having no glycosylated linker in the same way as in the preceding measurement of solubility in the aqueous solution.

As a result, the HER2(8-16) peptide unbound with the glycosylated linker had a solubility of 0.52 mg/mL ($4.9 \times 10^2$ µM)) in the aqueous acetic acid solution. In this respect, the precipitation of the HER2(8-16) peptide was able to be visually confirmed in the microtube. On the other hand, the glycosylated (Cys (asialo)-type) linker-HER2(8-16) conjugate (compound 1) was confirmed to have a solubility of 110 mg/mL or higher in the aqueous acetic acid solution. Surprisingly, the precipitation of the glycosylated (Cys (asialo)-type) linker-HER2(8-16) conjugate (compound 1) was unable to be confirmed even at a concentration of 110 mg/mL. Also, the glycosylated (Cys (disialo)-type) linker-HER2(8-16) conjugate (compound 8) was confirmed to have a solubility of 104 mg/mL or higher in the aqueous acetic acid solution. Surprisingly, the precipitation of the glycosylated (Cys (asialo)-type) linker-HER2(8-16) conjugate (compound 8) was unable to be confirmed even at a concentration of 104 mg/mL. These results demonstrated that the solubility of the glycosylated (Cys (asialo)-type) linker-HER2(8-16) conjugate (compound 1) and the glycosylated (Cys (disialo)-type) linker-HER2(8-16) conjugate (compound 8) in an aqueous solution is improved by 69 or more times the solubility of the unmodified HER2(8-16) peptide (compound 10) in terms of molar concentration (Table 1B).

TABLE 1B

Solubility of glycosylated linker-HER2(8-16) conjugate in aqueous acetic acid solution (0.1% AcOH)

| Sample | Solubility (µM) | Solubility (mg/mL) |
|---|---|---|
| Unmodified HER2(8-16) (compound 10) | $4.9 \times 10^2$ | 0.52 |
| Glycosylated (Cys (asialo)-type) linker-HER2(8-16) conjugate (compound 1) | $>3.7 \times 10^4$ | >110 |
| Glycosylated (Cys (disialo)-type) linker-HER2(8-16) conjugate (compound 8) | $>3.4 \times 10^4$ | >104 |

Example 1-4: Tracing of Hydrolysis Behavior in Aqueous Solution

The hydrolysis behaviors of the glycosylated (Cys (asialo)-type) linker-HER2(8-16) conjugate (compound 1)

and the glycosylated (Cys (disialo)-type) linker-HER2(8-16) conjugate (compound 8) obtained in Examples 1-1 and 1-2, respectively, were traced. Hydrolysis reaction was started by the addition of a buffer solution (acetate buffer solution (pH 4.0) or PBS (pH 7.4)) preset to a reaction temperature (25° C. or 37° C.) to each of the freeze-dried glycosylated (Cys (asialo)-type) linker-HER2(8-16) conjugate (compound 1) and glycosylated (Cys (disialo)-type) linker-HER2(8-16) conjugate (compound 8). The temperature during the reaction was kept at a constant temperature (25° C. or 37° C.) using a block incubator. A given amount of each solution was injected to HPLC at appropriate time intervals to trace the hydrolysis reaction. The relative starting material concentration was determined from an HPLC peak area corresponding to the starting material. The relative concentration of the starting material was plotted against incubation time. As a result, a linear plot was obtained, indicating that the hydrolysis reaction was primary reaction. Also, the terminal half-life $t_{1/2}$ of the starting material was calculated according to the expression $t_{1/2}=\ln(2)/k$ (wherein k represents the slope of the linear plot). The half-lives of the glycosylated (Cys (asialo)-type) linker-HER2(8-16) conjugate (compound 1) and the glycosylated (Cys (disialo)-type) linker-HER2(8-16) conjugate (compound 8) under each condition are shown in Tables 2 and 3.

TABLE 2

Hydrolysis half-life of glycosylated (Cys (asialo)-type) linker-HER2(8-16) conjugate (compound 1)

| Entry | Solvent | Temperature | Half-life |
| --- | --- | --- | --- |
| 1 | Acetate buffer solution (pH 4.0) | 25° C. | >30 days |
| 2 | Acetate buffer solution (pH 4.0) | 37° C. | >30 days |
| 3 | PBS (pH 7.4) | 25° C. | 146 hours |
| 4 | PBS (pH 7.4) | 37° C. | 78 hours |

TABLE 3

Hydrolysis half-life of glycosylated (Cys (disialo)-type) linker-HER2(8-16) conjugate (compound 8)

| Entry | Solvent | Temperature | Half-life |
| --- | --- | --- | --- |
| 1 | Acetate buffer solution (pH 4.0) | 25° C. | >30 days |
| 2 | Acetate buffer solution (pH 4.0) | 37° C. | >30 days |
| 3 | PBS (pH 7.4) | 25° C. | 121 hours |
| 4 | PBS (pH 7.4) | 37° C. | 106 hours |

The glycosylated (Cys (asialo)-type) linker-HER2(8-16) conjugate (compound 1) and the glycosylated (Cys (disialo)-type) linker-HER2(8-16) conjugate (compound 8) were both confirmed to be gradually hydrolyzed to produce the unmodified HER2(8-16) peptide (compound 10). As shown in Tables 2 and 3, the hydrolysis rate was confirmed to be faster at a higher pH (comparison between Entries 1 and 3 (25° C.) and comparison between Entries 2 and 4 (37° C.)). Also, the hydrolysis rate was confirmed to be faster at a higher temperature under the condition of pH 7.4 (comparison between Entries 3 and 4). Both the compound 1 and the compound 8 were very stable under the conditions of pH 4.0 and 37° C., and the formed hydrolysate 10 was only 1% or less of the starting material after the 48-hour tracing, showing that these compounds are hardly hydrolyzed under these conditions. The peptide having the disialo sugar chain-attached linker exhibited a faster hydrolysis rate than that of the peptide having the asialo sugar chain-attached linker under the conditions of pH 7.4 and 25° C. On the other hand, the peptide having the disialo sugar chain-attached linker exhibited a slower hydrolysis rate than that of the peptide having the asialo sugar chain-attached linker under the conditions of pH 7.4 and 37° C. As seen from these results, a preferred hydrolysis rate under particular conditions can also be adjusted by selecting the type of the sugar chain to be added.

(Example 2: Synthesis of Glycosylated (Cys (Asialo)-Type) Linker-HER2(8-16) Conjugate (Compound 1) on Solid Phase)

[Formula 36A]

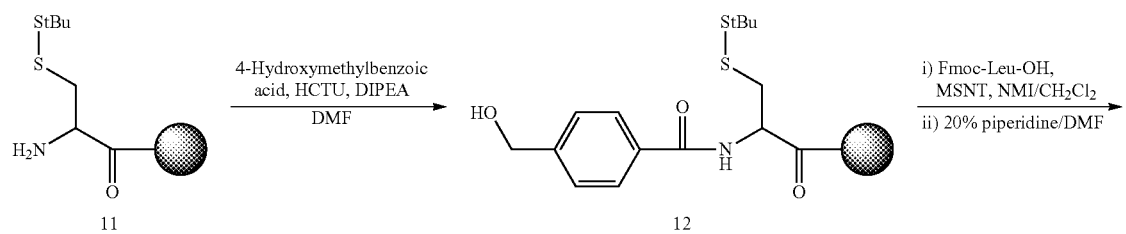

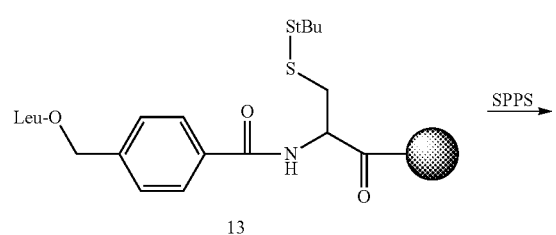

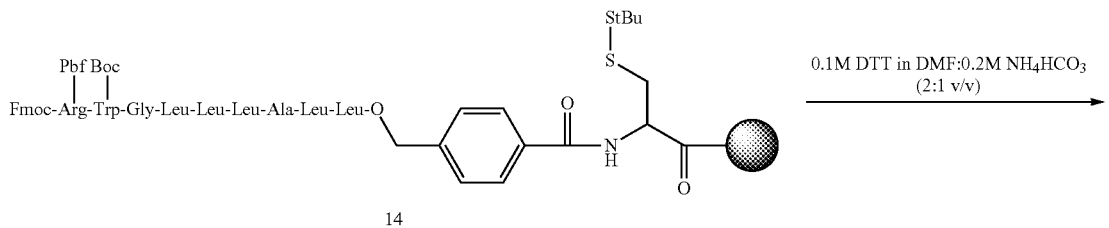
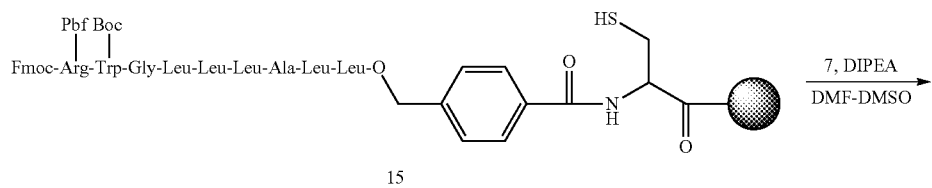
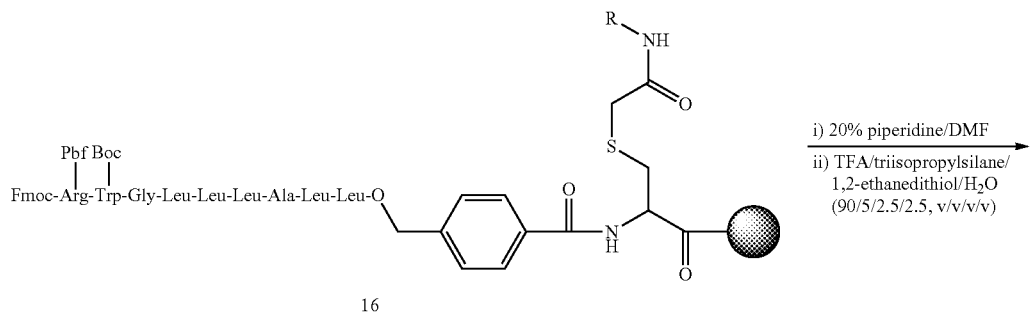
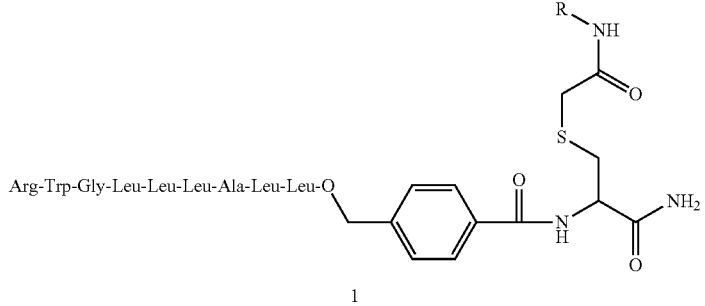

wherein R represents the following chemical formula:
[Formula 36B]

[Formula 36B]

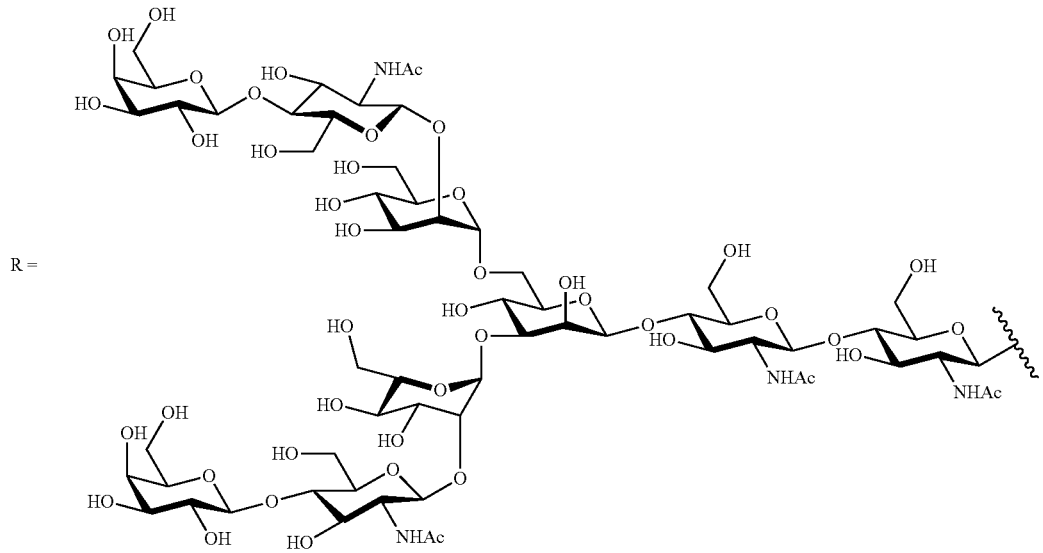

R =

Rink-Amide-PEGA resin (100 µmol) was placed in a column for solid-phase synthesis and washed with dichloromethane and DMF. After the washing, a DMF (2.5 mL) solution containing Fmoc-Cys(tButhio)-OH (173.4 mg, 0.402 mmol), HCTU (157 mg, 0.380 mmol), and 2,4,6-trimethylpyridine (79.6 µL, 0.600 mmol) was added thereto, and the mixture was shaken at room temperature for 10 minutes. After 10 minutes, the resin was washed with DMF. After the washing, the Fmoc protective group was removed by treatment with 20% piperidine in DMF to obtain compound 11 bonded to Cys(StBu(tButhio)) on the resin. The compound 11 on the resin was washed with DMF. Then, a DMF (2.5 mL) solution containing 4-hydroxymethyl-benzoic acid (60.8 mg, 0.400 mmol), HCTU (157 mg, 0.380 mmol), and DIPEA (104.5 µL, 0.600 mmol) was added thereto, and the mixture was shaken at room temperature. After 10 minutes, the resin was washed with DMF and dichloromethane to obtain compound 12 bonded to HMBA-Cys(StBu) on the resin. To the compound 12 on the resin, a dichloromethane (5.0 mL) solution containing Fmoc-Leu-OH (176.3 mg, 0.499 mmol), MSNT (149.0 mg, 0.503 mmol), and N-methylimidazole (27.9 µL, 0.350 mmol) was added, and the mixture was shaken at room temperature for 3 hours. The resin was washed with dichloromethane and DMF, and the Fmoc protective group was then removed by treatment with 20% piperidine in DMF to obtain compound 13 bonded to Leu-HMBA-Cys(StBu) on the resin. After washing with DMF, compound 14: Fmoc-Arg(Pbf)-Trp(Boc)-Gly-Leu-Leu-Leu-Ala-Leu-Leu-HMBA-Cys(StBu) (SEQ ID NO: 6) with protected amino acid side chains was synthesized on the resin bonded to the protected peptide by a solid-phase peptide synthesis method according to the Fmoc method using a Prelude (trademark) peptide synthesizer. The condensation reaction was carried out in DMF using HCTU as a condensing agent and N-methylmorpholine as a base.

A DMF solution (1 mL) containing a 0.2 M aqueous ammonium bicarbonate solution (500 µL) and 0.1 M DTT dissolved therein was added to an aliquot (10 µmol) of the resin bonded to the compound 14, and the mixture was shaken at room temperature. After 6 hours, the resin was washed with DMF to obtain compound 15: Fmoc-Arg(Pbf)-Trp(Boc)-Gly-Leu-Leu-Leu-Ala-Leu-Leu-HMBA-Cys (SEQ ID NO: 7) on the resin. To the compound 15, a DMSO-DMF mixed solution (1/1, v/v, 500 µL) containing asialo-BrAc 7 (52.8 mg, 30.0 µmol) and DIPEA (10.5 µL, 60.3 µmol) dissolved therein was added, and the mixture was shaken at room temperature for 12 hours to obtain compound 16: Fmoc-Arg(Pbf)-Trp(Boc)-Gly-Leu-Leu-Leu-Ala-Leu-Leu-(sugar chain added-linker: HMBA-Cys (asialo)) (SEQ ID NO: 8) on the resin. The resin was washed with DMF, and the Fmoc protective group was then removed by treatment with 20% piperidine in DMF. The resin was washed with DMF and dichloromethane. Then, trifluoroacetic acid:triisopropylsilane:ethanedithiol:water (=90:5:2.5:2.5) was added thereto, and the mixture was shaken at room temperature for 3 hours. To the filtrate, cooled ether was added to obtain crude peptide 1 as precipitates. The obtained crude peptide 1 (15.5 mg) was purified by HPLC [column: SHISEIDO CAPCELL PAK C18 UG-120 (5 µm), φ20×250 mm, flow rate: 7.0 mL/min, eluent A: 0.1% TFA in water, eluent B: 0.09% TFA/10% water/90% acetonitrile, gradient A:B=65:35→53.4:46.6 (24 min) linear concentration gradient elution] to obtain a glycosylated (Cys (asialo)-type) linker-HER2(8-16) conjugate (compound 1): Arg-Trp-Gly-Leu-Leu-Leu-Ala-Leu-Leu-(sugar chain added-linker: HMBA-Cys (asialo)) (5.0 mg, 1.7 µmol).

Example 3-1: Synthesis of Glycosylated Linker-HER2(8-16) Conjugate (Compound 20) Having Thioalkyl Structure <Synthesis of Glycosylated Linker (Compound 17) Having Thiol Group>

[Formula 37]

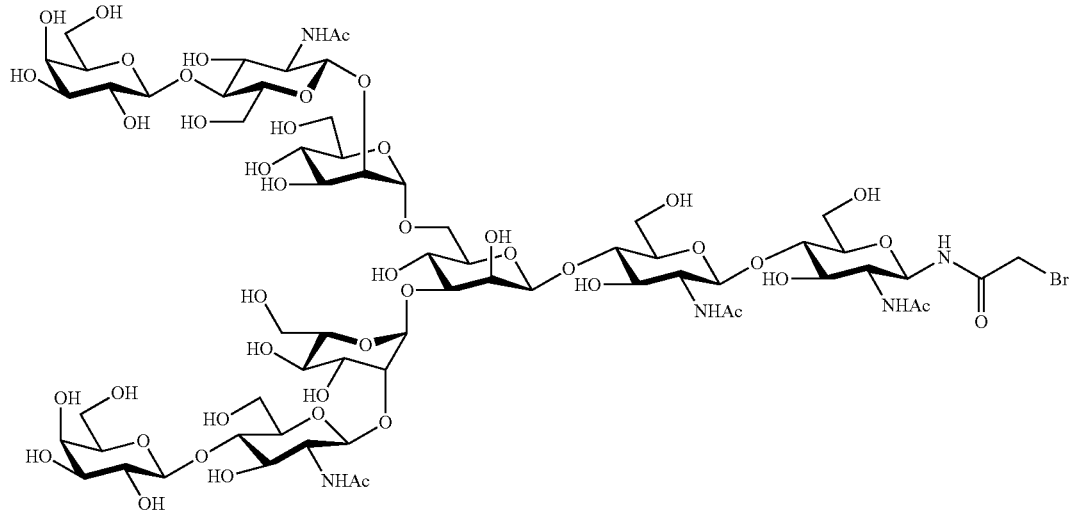

7

↓ 1,2-Ethanedithiol/ Phosphate buffer

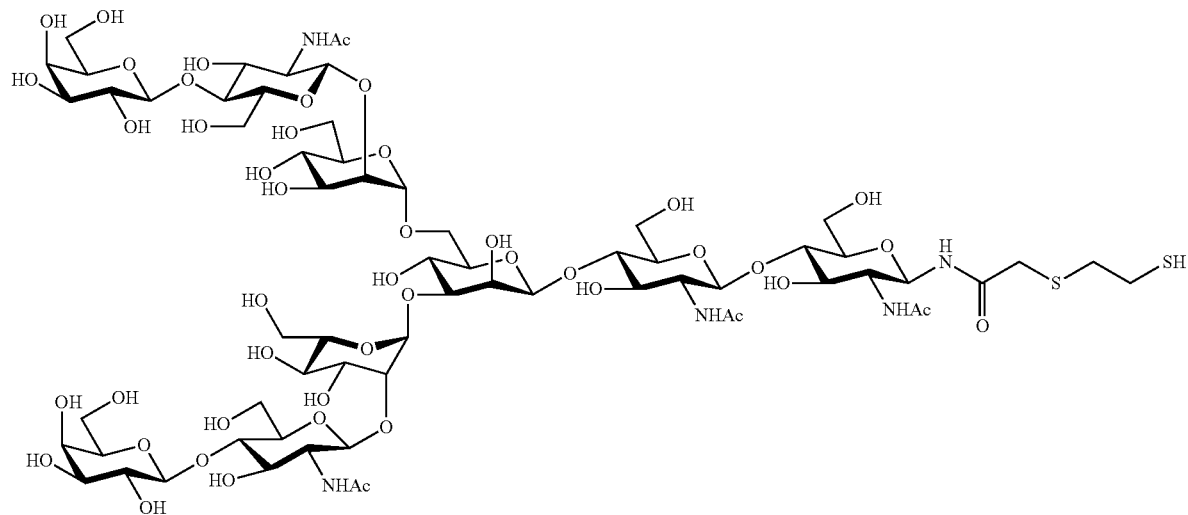

17

The asialo-BrAc 7 (131.7 mg, 75 μmol) dissolved in a phosphate buffer solution (0.1 M, pH 6.72, 4.0 mL) was gradually added dropwise to ethanedithiol (63 μL, 750 μmol, 10 eq) dissolved in a phosphate buffer solution (0.1 M, pH 6.72, 4.0 mL), and reacted at room temperature for 40 minutes. The completion of the reaction was confirmed by HPLC, and the reaction product was then purified by HPLC [column: SHISEIDO CAPCELL PAK C18 UG-120 (5 μm), φ20×250 mm, flow rate: 7.0 mL/min, eluent A: 0.1% TFA in water, eluent B: 0.09% TFA/10% water/90% acetonitrile, gradient A:B=99:1 (0-1 min)→80:20 (30 min)] to obtain the target compound 17 (118.3 mg, yield: 89%) as a glycosylated linker having a thiol group.

ESI-MS calcd for $C_{66}H_{111}N_5O_{46}S_2$: $[M+2H]^{2+}$+888.36, found 888.34.

Synthesis of Thioalkyl-Type Glycosylated Linker-HER2(8-16) Conjugate (Compound 20)

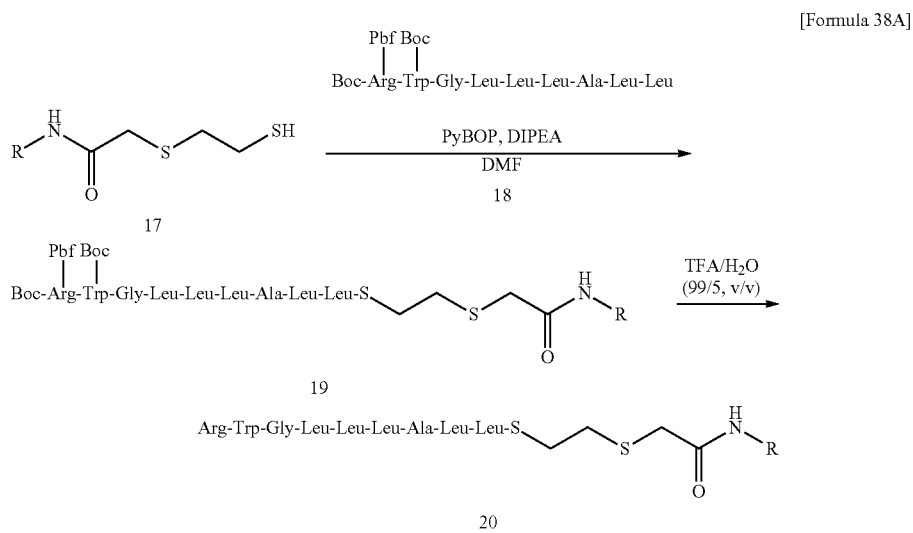

[Formula 38A]

wherein R represents the following chemical formula:

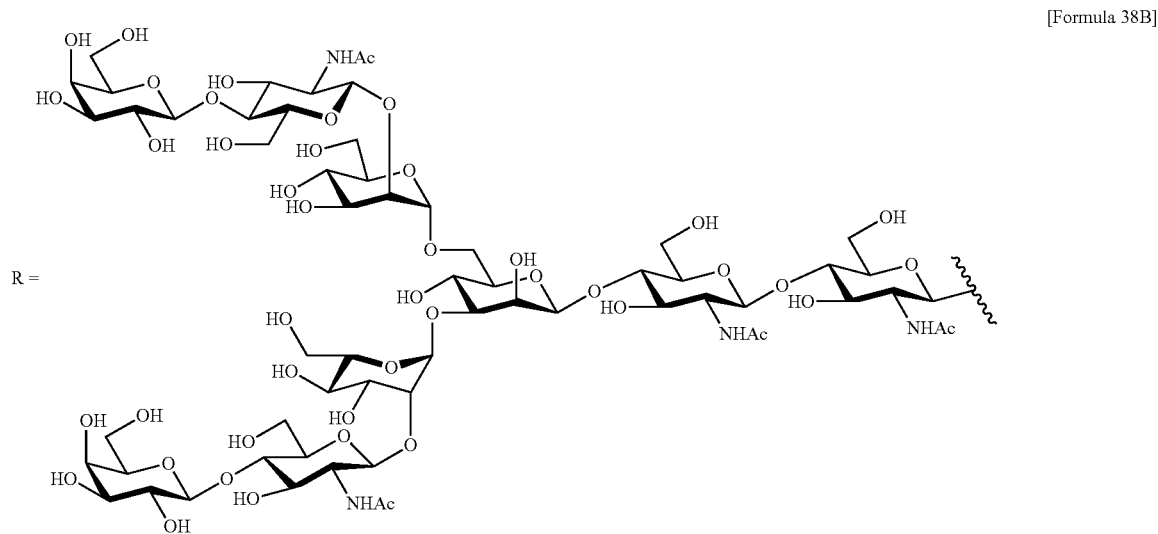

[Formula 38B]

The peptide with protected amino acid side chains synthesized on the resin using a Prelude (trademark) peptide synthesizer was excised from the resin by treatment with an AcOH-TFE (1/1, v/v) solution. The filtrate was concentrated to dryness under reduced pressure to obtain a peptide (compound 18): Boc-Arg(Pbf)-Trp(Boc)-Gly-Leu-Leu-Leu-Ala-Leu-Leu (SEQ ID NO: 9) with protected amino acid side chains.

The obtained peptide (compound 18) (63.5 mg, 41.8 μmol), the glycosylated linker (compound 17) (41.5 mg, 23.4 μmol) having a thiol group, and PyBOP (121.8 mg, 234 μmol) were dissolved in DMF (1 mL) and cooled to −15° C. in a nitrogen atmosphere. To this solution, DIPEA (40.0 μL, 40.7 μmol) was added, and the mixture was stirred at −15° C. After 3 hours, TFA (100 μL) was added thereto, and the mixture was concentrated to dryness under reduced pressure. To the obtained residue, a TFA-H$_2$O (95/5, v/v) solution (1 mL) was added, and the mixture was stirred for 3 hours. To the solution, ether was added to obtain a crude peptide as precipitates. The obtained crude peptide was purified by HPLC [column: SHISEIDO CAPCELL PAK C18 UG-120 (5 μm), φ20×250 mm, flow rate: 7.0 mL/min, eluent A: 0.1% TFA in water, eluent B: 0.09% TFA/10% water/90% acetonitrile, gradient A:B=65:35→35:55 (30 min) linear concentration gradient elution] to obtain a thioalkyl-type glycosylated linker-HER2(8-16) conjugate (compound 20): Arg-Trp-Gly-Leu-Leu-Leu-Ala-Leu-Leu-(sugar chain added-linker: SCH$_2$CH$_2$SCH$_2$CONH (asialo)) (SEQ ID NO: 10) (6.9 mg, yield: 10.5%).

ESI-MS calcd for $C_{118}H_{196}N_{18}O_{55}S_2$: $[M+2H]^{2+}$ 1406.52, $[M+3H]^{3+}$ 938.01. found 1406.10, 937.73.

Example 3-2: Synthesis of Glycosylated Linker-HER2(8-16) Conjugate (Compound 21) Having Thioaryl Structure
[Formula 39A]
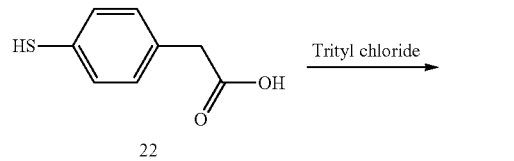
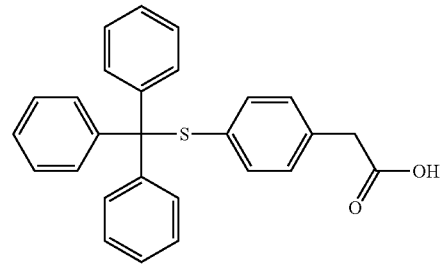
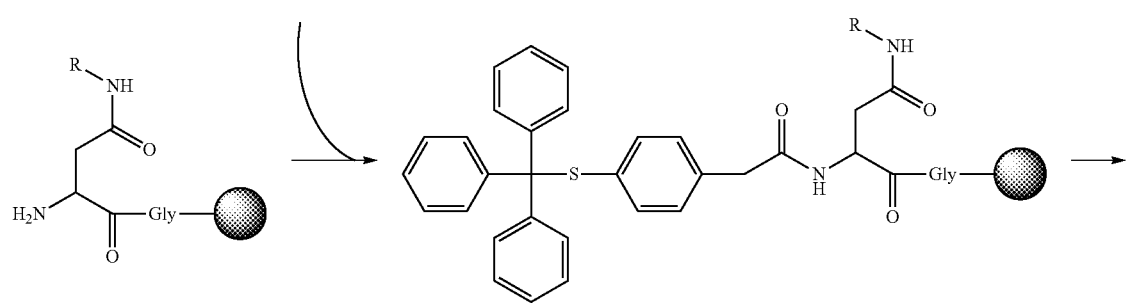
24
Rink Amide
PEGA resin
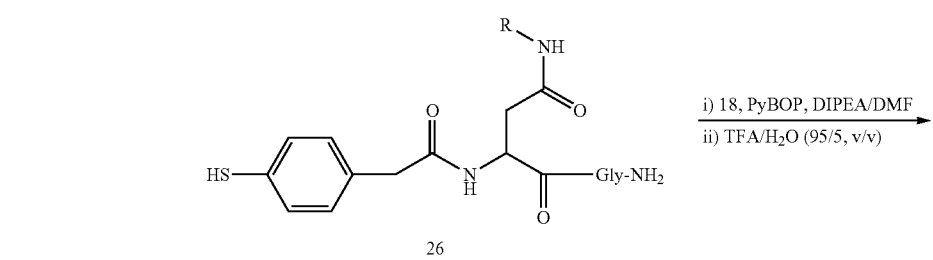

wherein R represents the following chemical formula:

[Formula 39B]

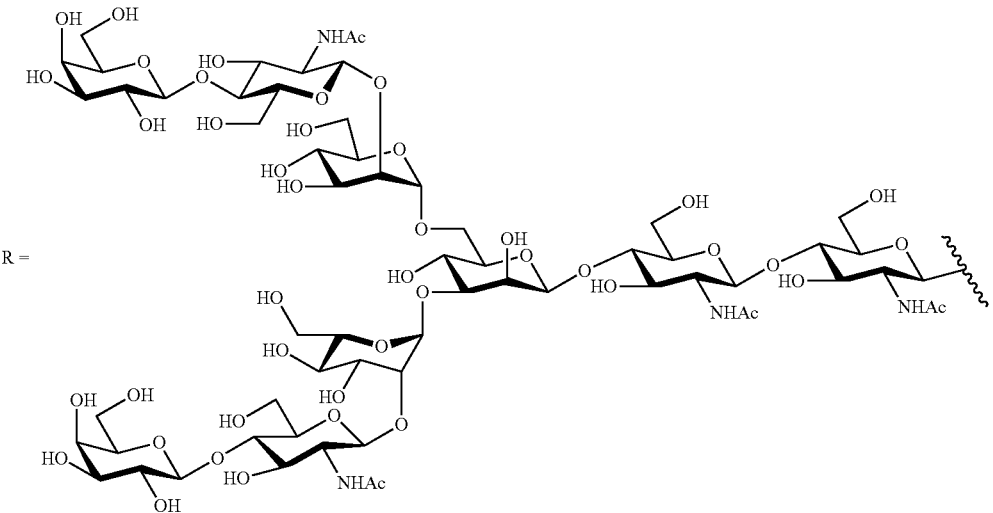

Trityl chloride (2.0 g, 7.1 mmol) was allowed to act on 4-mercaptophenylacetic acid (compound 22) (1.0 g, 6.1 mmol) in dichloromethane to obtain compound 23 (2.8 g). A DMF (2.0 mL) solution containing the compound 23 (320 µmol), HOBt (50.7 mg, 375 µmol), and DIC (54 µL, 522 µmol) was added to compound 24 (62 µmol) bonded to a glycopeptide (Asn(asialo)-Gly) consisting of 2 amino acid residues on Rink-Amide-PEGA resin, and the mixture was shaken at room temperature for 1 hour to obtain compound 25 on the resin. The resin was washed with DMF and dichloromethane. Then, a TFA:triisopropylsilane:water (=92.5:5:2.5) solution was added thereto, and the mixture was shaken at room temperature for 3 hours. Then, the filtrate was concentrated under reduced pressure to obtain compound 26 (19.6 mg, 10 µmol, yield: 16%) as a glycosylated linker.

ESI-MS calcd for $C_{76}H_{120}N_8O_{49}S$: $[M+2H]^{2+}$ 981.34. found 981.37.

The compound 26 (8.6 mg, 4.4 µmol) as a glycosylated linker, the peptide (compound 18) (35.0 mg, 23.0 µmol) with protected amino acid side chains, and PyBOP (22.8 mg, 43.8 µmol) were dissolved in DMF (0.4 mL) and cooled to −15° C. in a nitrogen atmosphere. To this solution, DIPEA (7.5 µL, 76.4 µmol) was added, and the mixture was stirred at −5° C. to −10° C. After 2.5 hours, TFA (50 µL) was added thereto, and the mixture was concentrated to dryness under reduced pressure. To the obtained residue, a TFA-H$_2$O (95/5, v/v) solution (1 mL) was added, and the mixture was stirred for 3 hours. To the solution, ether was added to obtain a crude peptide as precipitates.

The obtained crude peptide was purified by HPLC [column: SHISEIDO CAPCELL PAK C18 UG-120 (5 µm), ϕ20×250 mm, flow rate: 7.0 mL/min, eluent A: 0.1% TFA in water, eluent B: 0.09% TFA/10% water/90% acetonitrile, gradient A:B=65:35→35:55(30 min) linear concentration gradient elution] to obtain a thioaryl-type glycosylated linker-HER2(8-16) conjugate (compound 21): Arg-Trp-Gly-Leu-Leu-Leu-Ala-Leu-Leu-(sugar chain added-linker: 4-thiobenzoic acid-Asn(asialo)-Gly) (SEQ ID NO: 11) (2.3 mg, yield: 17.5%). ESI-MS calcd for $C_{128}H_{205}N_{21}O_{58}S_1$: $[M+2H]^{2+}$ 1500.09, $[M+3H]^+$ 1000.39. found 1499.67, 1000.08.

Example 3-3: Solubility Measurement

The solubility of the thioalkyl-type glycosylated linker-HER2(8-16) conjugate (compound 20) and the thioaryl-type glycosylated linker-HER2(8-16) conjugate (compound 21) in water was measured in the same way as in Example 1-3 except that the thioalkyl-type glycosylated linker-HER2(8-16) conjugate (compound 20) and the thioaryl-type glycosylated linker-HER2(8-16) conjugate (compound 21) were used instead of the glycosylated (Cys (asialo)-type) linker-HER2(8-16) conjugate (compound 1) and the glycosylated (Cys (disialo)-type) linker-HER2(8-16) conjugate (compound 7). For comparison, the solubility of the unmodified HER2(8-16) peptide (compound 10) was measured. As a result, the HER2(8-16) peptide unbound with the glycosylated linker had a solubility of 0.22 mg/mL ($2.1 \times 10^2$ µM)) in water. In this respect, the precipitation of the HER2(8-16) peptide was able to be visually confirmed in the microtube. On the other hand, the thioalkyl-type glycosylated linker-HER2(8-16) conjugate (compound 20) was confirmed to have a solubility of 77.4 mg/mL or higher in water. Surprisingly, the precipitation of the thioalkyl-type glycosylated linker-HER2(8-16) conjugate (compound 20) was unable to be confirmed even at a concentration of 77.4 mg/mL. Also, the thioaryl-type glycosylated linker-HER2(8-16) conjugate (compound 21) was confirmed to have a solubility of 76.7 mg/mL or higher in water. Surprisingly, the precipitation of the thioaryl-type glycosylated linker-HER2(8-16) conjugate (compound 8) was unable to be confirmed even at a concentration of 76.7 mg/mL. These results demonstrated that the solubility of the thioalkyl-type glycosylated linker-HER2(8-16) conjugate (compound 20) and the thioaryl-type glycosylated linker-HER2(8-16) conjugate (compound 21) in an aqueous solution is improved by 100 or more times the solubility of the unmodified HER2(8-16) peptide (compound 10) in terms of molar concentration.

TABLE 4

Solubility of thioalkyl-type or thioaryl-type glycosylated linker-HER2(8-16) conjugate in aqueous solution

| Sample | Solubility (μM) | Solubility (mg/mL) |
|---|---|---|
| Unmodified HER2(8-16) (compound 10) | $2.1 \times 10^2$ | 0.22 |
| Thioalkyl-type glycosylated linker-HER2(8-16) conjugate (compound 20) | $>2.8 \times 10^4$ | >77.4 |
| Thioaryl-type glycosylated linker-HER2(8-16) conjugate (compound 21) | $>2.6 \times 10^4$ | >76.7 |

Example 3-4: Tracing of Hydrolysis Behavior in Aqueous Solution

The hydrolysis behaviors of the thioalkyl-type glycosylated linker-HER2(8-16) conjugate (compound 20) and the thioaryl-type glycosylated linker-HER2(8-16) conjugate (compound 21) obtained in Examples 3-1 and 3-2, respectively, were traced. Specifically, the hydrolysis behaviors were traced in the same way as in Example 1-4 except that the freeze-dried thioalkyl-type glycosylated linker-HER2(8-16) conjugate (compound 20) and thioaryl-type glycosylated linker-HER2(8-16) conjugate (compound 21) were used instead of the freeze-dried glycosylated (Cys (asialo)-type) linker-HER2(8-16) conjugate (compound 1) and glycosylated (Cys (disialo)-type) linker-HER2(8-16) conjugate (compound 8), and the reaction temperature was set to 4° C., 25° C., or 37° C.

As a result of conducting the hydrolysis test and then HPLC analysis on the thioalkyl-type glycosylated linker-HER2(8-16) conjugate (compound 20), the production of the unmodified HER2(8-16) peptide (compound 10) was confirmed. The chemical formula given below represents the hydrolysis reaction of the thioalkyl-type glycosylated linker-HER2(8-16) conjugate (compound 20), wherein the compound 27 represents a glycosylated linker resulting from the hydrolysis reaction of the compound 20.

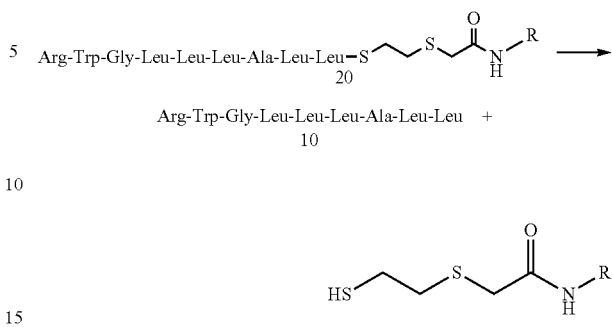

[Formula 40A]

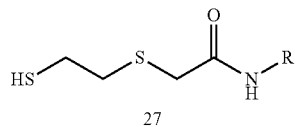

wherein R represents the following chemical formula:

[Formula 40B]

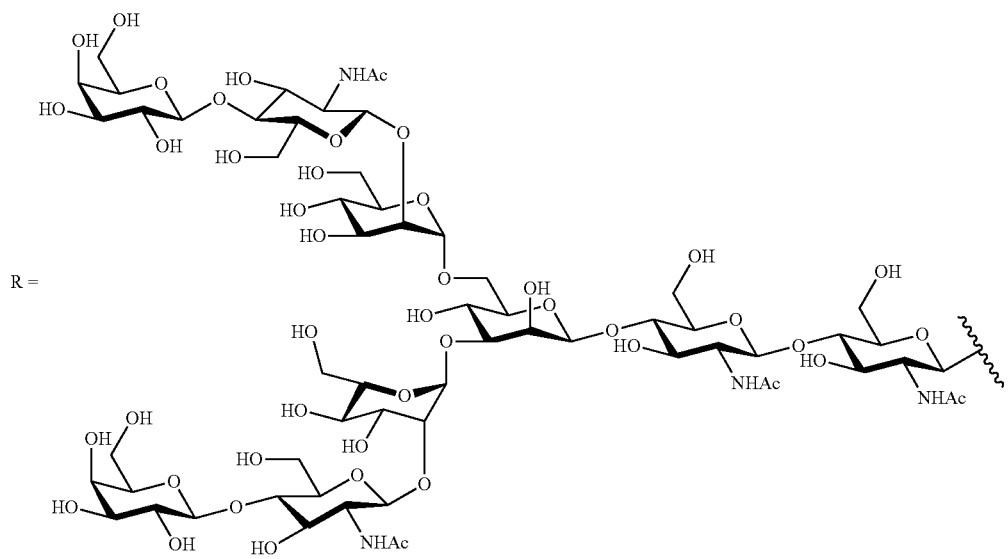

The relative concentration of the starting material was plotted against incubation time as to the thioalkyl-type glycosylated linker-HER2(8-16) conjugate (compound 20) in the same way as in Example 1-4. The obtained graph is shown in FIGS. 1A and 1B. The half-life of the thioalkyl-type glycosylated linker-HER2(8-16) conjugate (compound 20) under each condition is shown in Table 5.

TABLE 5

Hydrolysis half-life of thioalkyl-type glycosylated linker-HER2(8-16) conjugate (compound 20)

| Entry | Solvent | Temperature | Half-life |
|---|---|---|---|
| 1 | Acetate buffer solution (pH 4.0) | 25° C. | >30 days |
| 2 | Acetate buffer solution (pH 4.0) | 37° C. | 24 days |
| 3 | PBS (pH 7.4) | 4° C. | 9.6 days |
| 4 | PBS (pH 7.4) | 25° C. | 5.1 days |
| 5 | PBS (pH 7.4) | 37° C. | 32 hours |

As shown in Table 5, the hydrolysis half-life in PBS (pH 7.4) was 5 days at 25° C. and, by contrast, was 32 hours at 37° C. These results demonstrated that the thioalkyl-type glycosylated linker-HER2(8-16) conjugate (compound 20) exhibits a faster hydrolysis rate at a higher temperature (comparison between Entries 1 and 2 (pH 4.0) and comparison among Entries 3, 4, and 5 (pH 7.4)). As a result of observing the influence of pH at 37° C., the hydrolysis half-life in the acetate buffer solution (pH 4.0) was 24 days. The hydrolysis was therefore confirmed to be promoted at a higher pH (comparison between Entries 2 and 5). Thus, the thioalkyl-type glycosylated linker-HER2(8-16) conjugate (compound 21) having a thioester bond, as with the glycosylated linker-HER2(8-16) conjugate (compound 1 or 8) having an ester bond, was confirmed to exhibit a faster hydrolysis rate at a higher temperature and/or pH.

As a result of hydrolyzing the thioaryl-type glycosylated linker-HER2(8-16) conjugate (compound 21), followed by HPLC analysis, the production of the unmodified HER2(8-16) peptide (compound 10) was confirmed, as also found in the thioalkyl-type glycosylated linker-HER2(8-16) conjugate (compound 20). The chemical formula given below represents the hydrolysis reaction of the thioaryl-type glycosylated linker-HER2(8-16) conjugate (compound 21), wherein the compound 28 represents a glycosylated linker resulting from the hydrolysis reaction of the compound 21.

[Formula 41A]

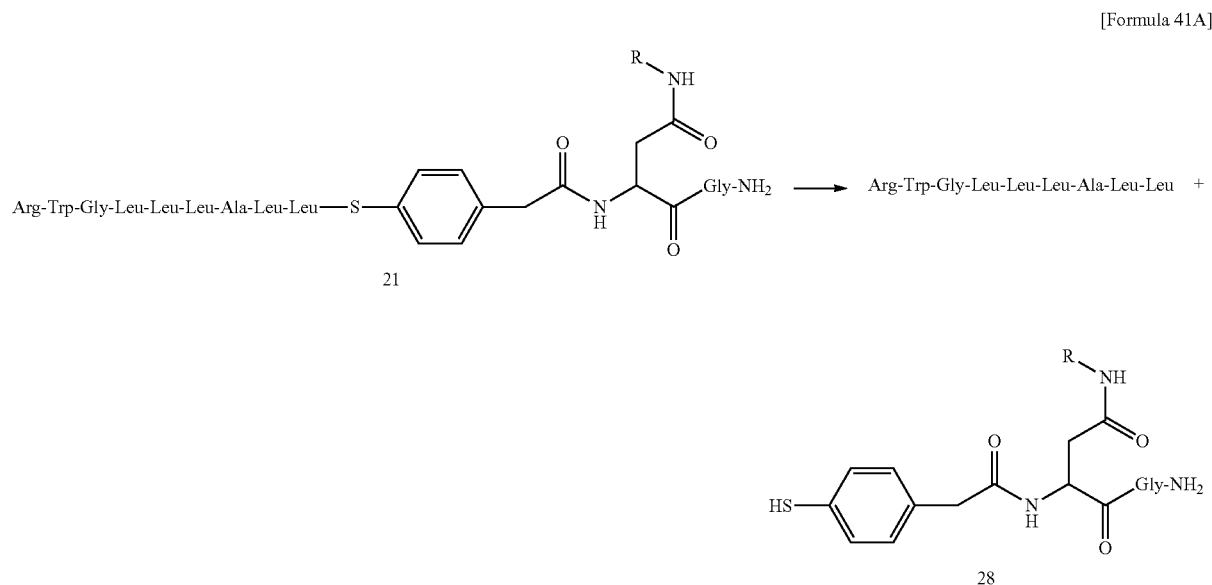

wherein R represents the following chemical formula:

[Formula 41B]

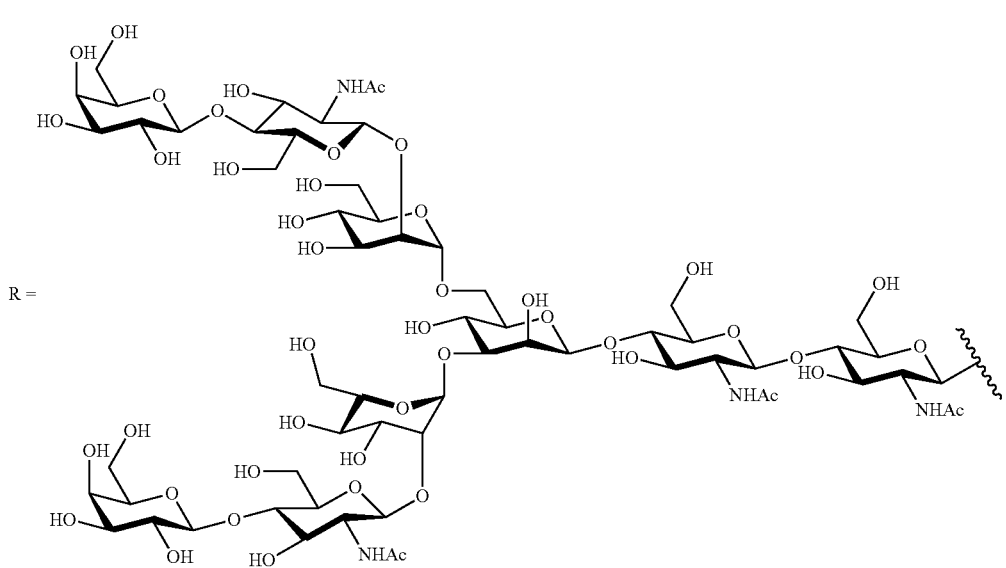

The relative concentration of the starting material was also plotted against incubation time as to the thioaryl-type glycosylated linker-HER2(8-16) conjugate (compound 21). The obtained graph is shown in FIGS. 2A and 2B. The half-life of the thioaryl-type glycosylated linker-HER2(8-16) conjugate (compound 21) under each condition is shown in Table 6.

TABLE 6

Hydrolysis half-life of thioaryl-type glycosylated linker-HER2(8-16) conjugate (compound 21)

| Entry | Solvent | Temperature | Half-life |
|---|---|---|---|
| 1 | Acetate buffer solution (pH 4.0) | 25° C. | 19 days |
| 2 | Acetate buffer solution (pH 4.0) | 37° C. | 10 days |
| 3 | PBS (pH 7.4) | 4° C. | 66 hours |
| 4 | PBS (pH 7.4) | 25° C. | 25 hours |
| 5 | PBS (pH 7.4) | 37° C. | 4.0 hours |

As shown in Table 6, the hydrolysis half-life in PBS (pH 7.4) was 66 hours at 4° C. and 25 hours at 25° C. and, by contrast, was 4.0 hours at 37° C. These results demonstrated that the thioaryl-type glycosylated linker-HER2(8-16) conjugate (compound 21) exhibits a faster hydrolysis rate at a higher temperature (comparison between Entries 1 and 2 (pH 4.0) and comparison among Entries 3, 4, and 5 (pH 7.4)). As a result of observing the influence of pH at 37° C., the hydrolysis half-life in the acetate buffer solution (pH 4.0) was 10 days. The hydrolysis was therefore confirmed to be promoted at a higher pH (comparison between Entries 2 and 5). Thus, the glycosylated linker-HER2(8-16) conjugate having a thioester bond, as with the glycosylated linker-HER2(8-16) conjugate having an ester bond, was confirmed to exhibit a faster hydrolysis rate at a higher temperature and/or pH.

The hydrolysis rates of the asialo sugar chain-attached linker-HER2(8-16) conjugates, compounds 20, 21, and 1, in PBS (pH 7.4) at 37° C. were ranked in the order of the thioaryl-type glycosylated linker-HER2(8-16) conjugate (compound 21) having a thioester bond (4.0 hours)>the thioalkyl-type glycosylated linker-HER2(8-16) conjugate (compound 20) having a thioester bond (32 hours)>the glycosylated linker-HER2(8-16) conjugate (compound 1) having an ester bond (78 hours) (FIG. 3). These results showed that the thioester-type exhibits a faster hydrolysis rate than that of the ester-type. These results also demonstrated that among the thioester-type forms, the thioaryl-type is hydrolyzed faster than the thioalkyl-type.

Example 4-1: Synthesis of Glycosylated (Cys (Disialo)-Type) Linker-Chemerin 9 Conjugate (Compound 29)

This chemerin 9 has agonistic activity against a G protein coupled receptor ChemR23 and therefore has the potential as a therapeutic and/or preventive agent for immunological diseases, inflammatory diseases, and diabetes mellitus. Chemerin 9, however, is known to undergo degradation by protease in vivo and be therefore very unstable (patent literature Japanese Patent Laid-Open No. 2010-229093). Thus, the glycosylated linker of the present invention according to one embodiment was introduced to this chemerin 9, and the produced conjugate was evaluated for its hydrolysis half-life. First, a conjugate was synthesized in which a glycosylated (Cys (disialo)-type) linker and chemerin 9 (SEQ ID NO: 12: YFPGQFAFS, corresponding to the amino acid sequences of SEQ ID NOs: 31 to 36 disclosed in the patent literature US2003096299) were bonded via an ester bond.

[Formula 42]

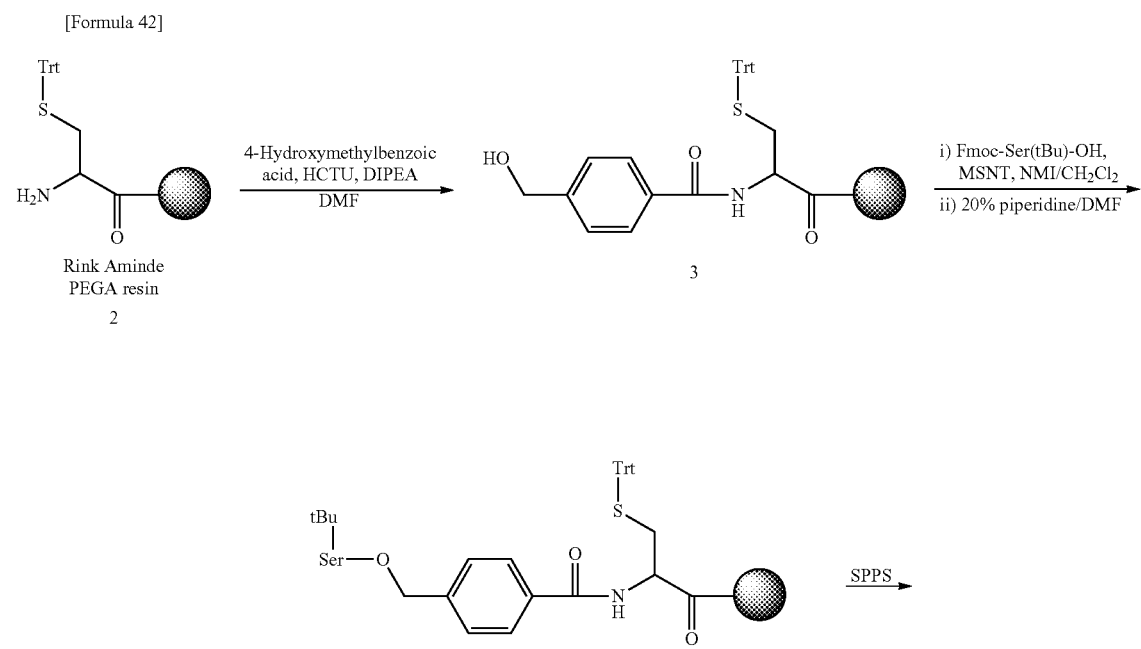

-continued
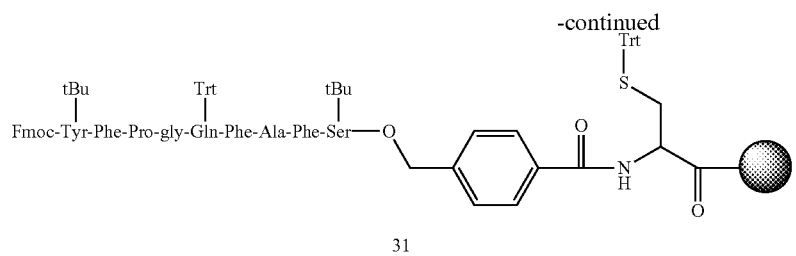
31
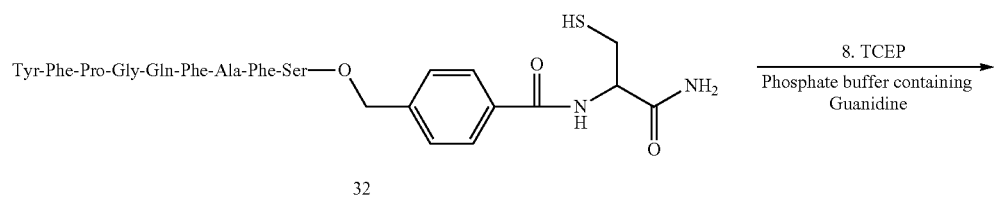
32
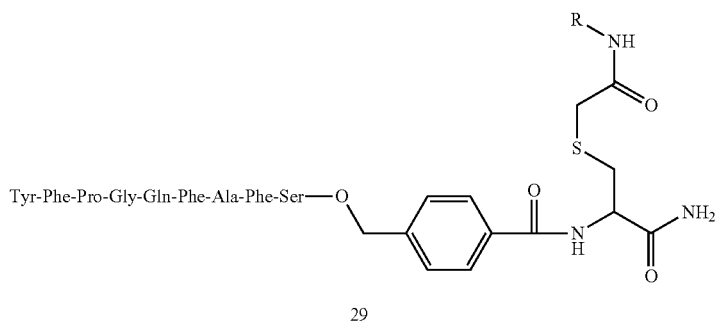
29
wherein R represents the following chemical formula:
[Formula 43]
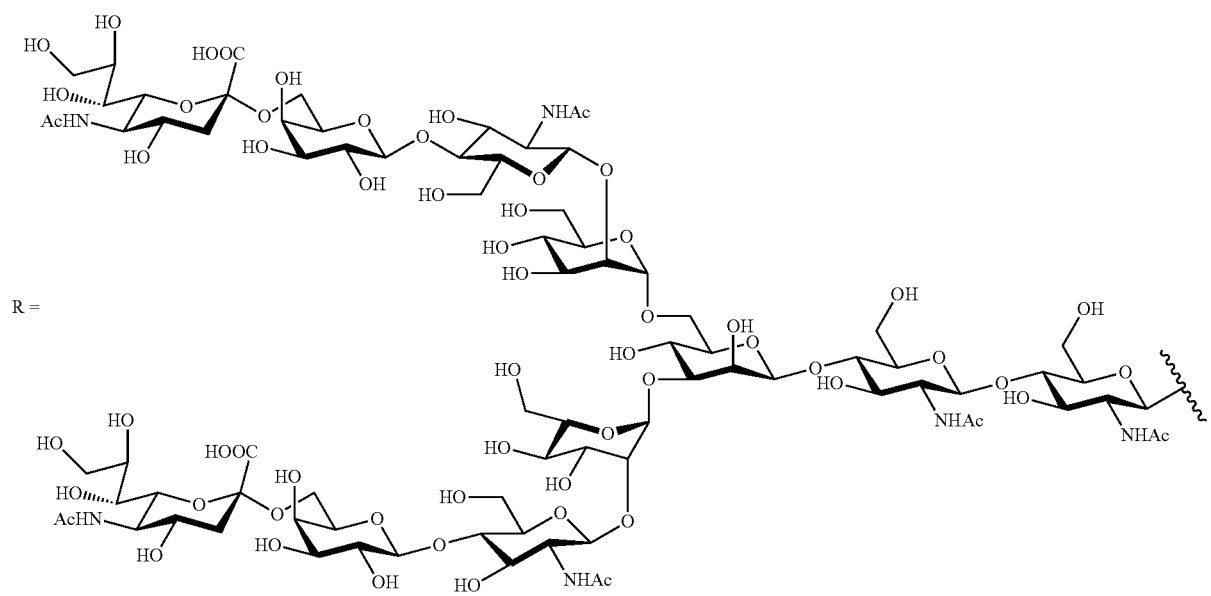

-continued

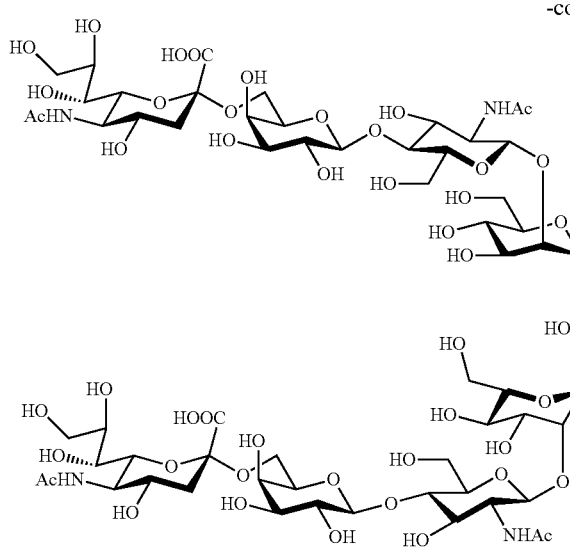
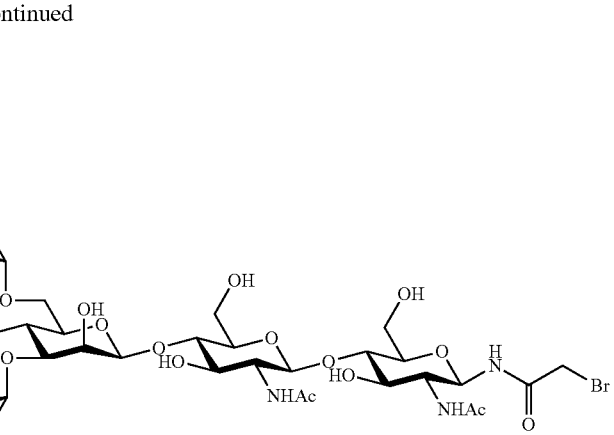

Rink-Amide-PEGA resin (100 μmol) was placed in a column for solid-phase synthesis and washed with dichloromethane and DMF. After the washing, a DMF (2.5 mL) solution containing Fmoc-Cys(Trt)-OH (234 mg, 0.399 mmol), HCTU (157 mg, 0.380 mmol), and 2,4,6-trimethylpyridine (79.6 μL, 0.600 mmol) was added thereto, and the mixture was shaken at room temperature for 10 minutes. After 10 minutes, the resin was washed with DMF, and this condensation operation was then repeated once again. After the completion of the second condensation operation, the resin was washed with DMF and dichloromethane. After the washing, the Fmoc protective group was removed by treatment with 20% piperidine in DMF to obtain compound 2 bonded to Cys(Trt) on the resin. The compound 2 on the resin was washed with DMF. Then, a DMF (2.5 mL) solution of 4-hydroxymethyl-benzoic acid (61.1 mg, 0.402 mmol), HCTU (157.8 mg, 0.381 mmol), and DIPEA (104.5 μL, 0.600 mmol) was added thereto, and the mixture was shaken at room temperature. After 1 hour, the resin was washed with DMF and dichloromethane to obtain compound 3 bonded to HMBA-Cys(Trt) on the resin.

A dichloromethane (2.5 mL) solution containing Fmoc-Ser(tBu)-OH (96.9 mg, 0.253 mmol), MSNT (74.1 mg, 0.250 mmol), and N-methylimidazole (14.0 μL, 0.177 mmol) was added to an aliquot (50 μmol) of the obtained resin bonded to the compound 3, and the mixture was shaken at room temperature for 1 hour. After the shaking for 1 hour, the resin was washed with dichloromethane and DMF. After the washing, the Fmoc protective group was removed by treatment with 20% piperidine in DMF to obtain compound 30 bonded to Ser(tBu)-HMBA-Cys(Trt) on the resin. After washing with DMF, compound 31: Fmoc-Tyr(tBu)-Phe-Pro-Gly-Gln(Trt)-Phe-Ala-Phe-Ser(tBu)-HMBA-Cys(Trt) (SEQ ID NO: 13) bonded to the peptide with protected amino acid side chains was synthesized on the resin by a solid-phase peptide synthesis method according to the Fmoc method using a Prelude (trademark) peptide synthesizer. The condensation reaction in the solid-phase synthesis method was carried out in DMF using HCTU as a condensing agent and N-methylmorpholine as a base.

The Fmoc protective group on the compound 31 was removed by treatment with 20% piperidine in DMF. The resin was washed with DMF and dichloromethane. Then, TFA:triisopropylsilane:ethanedithiol:water (=90:5:2.5:2.5) was added thereto, and the mixture was shaken at room temperature for 3 hours. To the filtrate, cooled ether was added to obtain crude peptide 32: Tyr-Phe-Pro-Gly-Gln-Phe-Ala-Phe-Ser-HMBA-Cys (SEQ ID NO: 14) as precipitates.

The obtained crude peptide 32 (14.2 mg), disialo-BrAc 9 (41.6 mg, 17.7 μmol), and TCEP (16.0 mg, 55.8 μmol) were dissolved in a 0.2 M phosphate buffer solution (pH 6.8, 1.15 mL) containing 7 M guanidine hydrochloride and reacted at room temperature. After 3 hours, the reaction solution was purified by HPLC [column: SHISEIDO CAPCELL PAK C18 UG-120 (5 μm), φ20×250 mm, flow rate: 7.0 mL/min, eluent A: 0.1% AcOH in water, eluent B: 0.09% AcOH/10% water/90% acetonitrile, gradient A:B=70:30→55:45 (10 min) linear concentration gradient elution] to obtain a glycosylated (Cys (disialo)-type) linker-chemerin 9 conjugate (compound 29): Tyr-Phe-Pro-Gly-Gln-Phe-Ala-Phe-Ser-(sugar chain added-linker: HMBA-Cys (disialo)) (SEQ ID NO: 15) (19.0 mg, 5.33 μmol). ESI-MS calcd for $C_{151}H_{217}N_{19}O_{77}S$ $[M+3H]^{3+}$ 1187.8, $[M+4H]^{4+}$ 891.1, $[M+5H]^{5+}$ 713.1. found 1187.8, 891.1, 713.1.

Example 4-2: Tracing of Hydrolysis Behavior in Aqueous Solution

The hydrolysis behavior of the glycosylated (Cys (disialo)-type) linker-chemerin 9 conjugate (compound 29) obtained in Example 4-1 was traced. Specifically, the hydrolysis behavior was traced in the same way as in Example 1-4 except that the freeze-dried glycosylated (Cys (disialo)-type) linker-chemerin 9 conjugate (compound 29) was used instead of the freeze-dried glycosylated (Cys (asialo)-type) linker-HER2(8-16) conjugate (compound 1) and glycosylated (Cys (disialo)-type) linker-HER2(8-16) conjugate (compound 8), and an acetate buffer solution (pH 4.0), PBS (pH 7.4), and a borate buffer solution (pH 9.0) were used as buffer solutions.

As a result of hydrolyzing the glycosylated (Cys (disialo)-type) linker-chemerin 9 conjugate (compound 29), followed by HPLC analysis, the production of the unmodified chemerin 9 peptide Tyr-Phe-Pro-Gly-Gln-Phe-Ala-Phe-Ser (compound 33) having the amino acid sequence of chemerin 9 was confirmed. The chemical formula given below represents the hydrolysis reaction of the glycosylated (Cys (disialo)-type) linker-chemerin 9 conjugate (compound 29).

[Formula 44A]

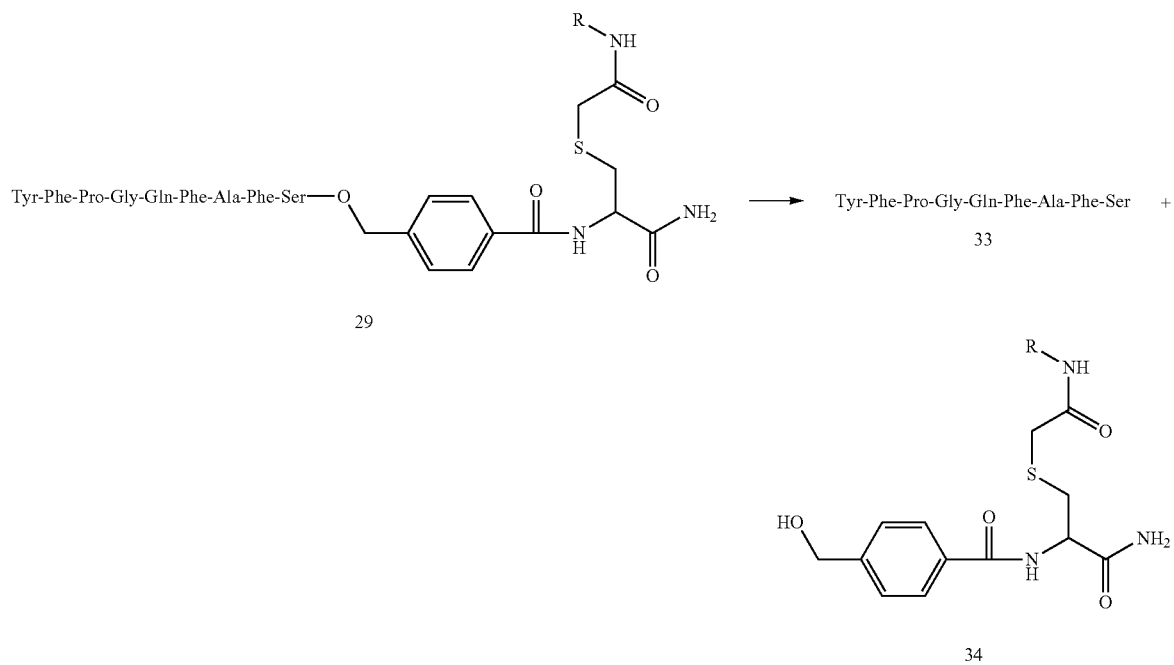

wherein R represents the following chemical formula:

[Formula 44B]

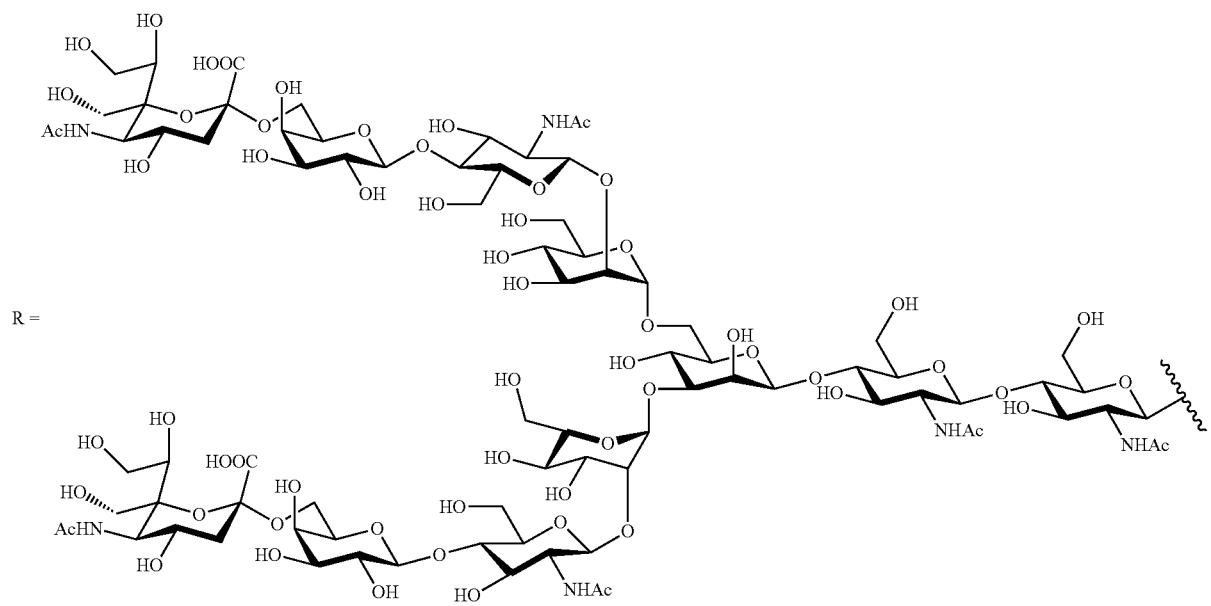

The relative concentration of the starting material was plotted against incubation time as to the glycosylated (Cys (disialo)-type) linker-chemerin 9 conjugate (compound 29) in the same way as in Example 1-4. The obtained graph is shown in FIG. 4. The half-life of the glycosylated (Cys (disialo)-type) linker-chemerin 9 conjugate (compound 29) under each condition is shown in Table 7.

TABLE 7

Hydrolysis half-life of glycosylated (Cys (disialo)-type) linker-chemerin 9 conjugate (compound 29) in buffer solution

| Entry | Solvent | Temperature | Half-life |
|---|---|---|---|
| 1 | Acetate buffer solution (pH 4.0) | 37° C. | >30 days |

TABLE 7-continued

Hydrolysis half-life of glycosylated (Cys (disialo)-type) linker-chemerin 9 conjugate (compound 29) in buffer solution

| Entry | Solvent | Temperature | Half-life |
|---|---|---|---|
| 2 | PBS (pH 7.4) | 37° C. | 45 hours |
| 3 | Borate buffer solution (pH 9.0) | 37° C. | 0.83 hours |
| 4 | Borate buffer solution (pH 9.0) | 25° C. | 2.4 hours |
| 5 | 50 mM aqueous NaOH solution | 25° C. | <2 minutes |

As shown in Table 7, the formed hydrolysate (compound 33) under the condition of 37° C. in the acetate buffer solution (0.1 M, pH 4.0) was only 1% or less of the starting material (compound 29) after the 49-hour tracing, showing that the compound is hardly hydrolyzed (note that the elimination of sialic acid present at the non-reducing end in the sugar chain structure was observed; and the content of the desialylated form was increased from 4.7% to 8.7% before and after the start of the hydrolysis behavior test). On the other hand, it was found that the hydrolysis reaction proceeded in PBS (pH 7.4) and the borate buffer solution (pH 9.0) to obtain the unmodified peptide (compound 33) having the amino acid sequence of chemerin 9. The half-life determined from the obtained curve was 45.0 hours (1.9 days) at 37° C. in PBS. As a result of tracing the hydrolysis behavior at 37° C. in the borate buffer solution (0.1 M, pH 9.0), the half-life was 0.83 hours (50 minutes).

As a result of dissolving the glycosylated (Cys (disialo)-type) linker-chemerin 9 conjugate (compound 29) in a 50 mM aqueous sodium hydroxide solution, this compound disappeared completely in 2 minutes to produce the unmodified peptide (compound 33) having the amino acid sequence of chemerin 9. The hydrolysis under basic conditions was confirmed to be very rapid, as reported in the literature.

The glycosylated (Cys (disialo)-type) linker-chemerin 9 conjugate (compound 29), as with the other compounds, was confirmed to exhibit a faster hydrolysis rate at a higher pH (Entries 1, 2, and 3). In the case of the same pH, the hydrolysis was confirmed to be promoted at a higher temperature (Entries 3 and 4).

After the hydrolysis behavior test, the reaction solution was subjected to HPLC [column: SHISEIDO CAPCELL PAK C18 UG-120 (5 μm), φ4.6×250 mm, flow rate: 0.7 mL/min, eluent A: 0.1% TFA in water, eluent B: 0.09% TFA/10% water/90% acetonitrile, gradient A:B=95:5→50:50 (20 min) linear concentration gradient elution]analysis. As a result, the peak of the glycosylated linker moiety (compound 34) was confirmed at a retention time of 10.2 minutes.

ESI-MS of compound 34: (m/z) calcd for $C_{97}H_{153}N_9O_{65}S$ $[M+2H]^{2+}$ 1258.93, $[M+3H]^{3+}$ 839.62. found 1258.98, 839.65.

From these results, it can be expected that the conjugate with the bonded glycosylated linker of the present invention can be prepared in a solution having a low pH at room temperature before administration without causing the hydrolysis of the compound and can be hydrolyzed under in vivo conditions after administration to exert the original activity of the peptide.

SEQUENCE LISTING

Sequence Listing. TXT

The invention claimed is:

1. A glycosylated linker for bonding to a physiologically active substance having at least one carboxy group, wherein the glycosylated linker is represented by the following formula (A):

$$X—R^1—Y—R^2 \quad (A)$$

wherein
X represents an oxygen atom (O) having a leaving group or a sulfur atom (S) having a leaving group;
$R^1$ represents —$R^3$—$R^4$—;
$R^3$ represents substituted or unsubstituted $C_1$-$C_5$ alkyl;
$R^4$ represents substituted or unsubstituted $C_5$-$C_{16}$ aryl;
Y represents —CO—; and
$R^2$ represents a glycosylated cysteinamide;
the sugar chain and the amino acid of the glycosylated cysteinamide are bonded to each other via a linker, the linker being —$CH_2$—CONH—;
the reducing end of the sugar chain is bonded to the nitrogen atom in the linker; and
the glycosylated linker becomes capable of binding to the carboxy group of the physiologically active substance by the elimination of the leaving group in the oxygen atom (O) or the sulfur atom (S).

2. The glycosylated linker according to claim 1, wherein the sugar chain in the glycosylated cysteinamide represented by $R^2$ consists of 4 or more sugar residues.

3. The glycosylated linker according to claim 1, wherein the sugar chain in the glycosylated cysteinamide represented by $R^2$ is a biantennary complex-type sugar chain, a triantennary complex-type sugar chain, or a tetraantennary complex-type sugar chain.

4. The glycosylated linker according to claim 3, wherein the sugar chain is a biantennary complex-type sugar chain selected from the group consisting of a disialo sugar chain, a monosialo sugar chain, an asialo sugar chain, a di-GlcNAc sugar chain, and a dimannose sugar chain.

5. The glycosylated linker according to claim 1, wherein the sugar chain in the glycosylated cysteinamide represented by $R^2$ is a sugar chain represented by the following formula:

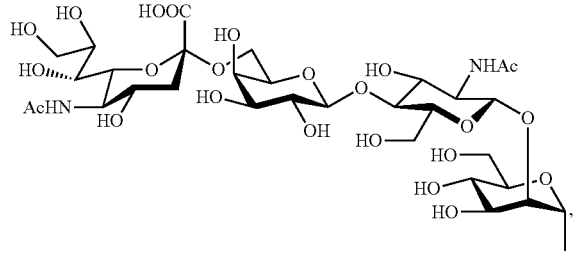

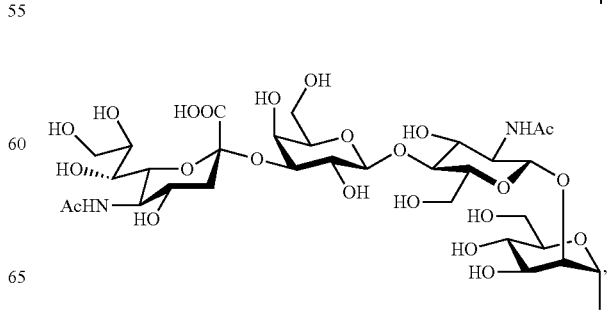

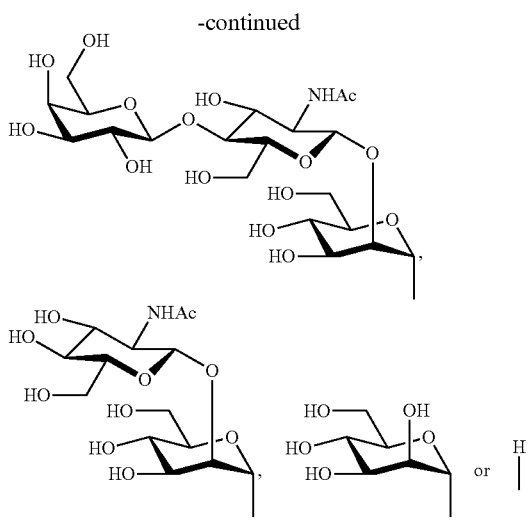

and Ac represents an acetyl group.

6. A compound comprising a glycosylated linker moiety derived from a glycosylated linker according to claim 1 and a physiologically active substance moiety, or a salt thereof, wherein
the physiologically active substance has at least one carboxy group, and
the glycosylated linker moiety is bonded to the physiologically active substance moiety through an ester bond or a thioester bond formed with the carboxy group of the physiologically active substance moiety by the elimination of the leaving group in the oxygen atom (O) or the sulfur atom (S).

7. The compound according to claim 6 or a salt thereof, wherein the physiologically active substance is a low-molecular weight physiologically active substance or a biopolymer, wherein said low-molecular weight physiologically active substance is selected from the group consisting of acarbose, alaproclate, alendronate, amantadine, amikacin, amineptine, aminoglutethimide, amisulpride, amlodipine, amotosalen, amoxapine, amoxicillin, amphetamine, amphotericin B, ampicillin, amprenavir, amrinone, anileridine, apraclonidine, apramycin, articaine, atenolol, atomoxetine, avizafone, baclofen, benazepril, benserazide, benzocaine, betaxolol, bleomycin, bromfenac, brofaromine, carvedilol, cathine, cathinone, carbutamide, cephalexin, clinafloxacin, ciprofloxacin, deferoxamine, delavirdine, desipramine, daunorubicin, dexmethylphenidate, dexmethylphenidate, diaphenylsulfone, dizocilpine, dopamine, dobutamine, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecainide, fluvoxamine, fosamprenavir, frovatriptan, furosemide, fluoxetine, gabapentin, gatifloxacin, gemifloxacin, gentamycin, grepafloxacin, hexylcaine, hydralazine, hydrochlorothiazide, icofungipen, idarubicin, imiquimod, isoproterenol, isradipine, kanamycin A, ketamine, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantrone, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazine, sulfamerazine, sertraline, spectinomycin, sulfalene, sulfamethoxazole, tacrine, tamsulosin, terbutaline, timolol, tirofiban, tobramycin, tocainide, tosufloxacin, trandolapril, tranexamic acid, tranylcypromine, trimetrexate, trovafloxacin, valaciclovir, valganciclovir, vancomycin, viomycin, viloxazine, zalcitabine, penicillin, cephalosporin, streptomycin, destomycin, kasugamycin, tylosin, erythromycin, oleandomycin, spiramycin, lincomycin, colistin, bacitracin, salinomycin, monensin, lasalocid, tetracycline, chloramphenicol, virginiamycin, sulfadimethoxine, oxolinic acid, piromidic acid, difurazone, zearalenone, deoxynivalenol, patulin, fumonisin, ochratoxin, tetrodotoxin, okadaic acid, saxitoxin, and gonyautoxin.

8. The compound according to claim 6 or a salt thereof, wherein the biopolymer is selected from the group consisting of a protein, a polypeptide, a polynucleotide, and a peptide nucleic acid.

9. The compound according to claim 6 or a salt thereof, wherein the compound or the salt thereof has improved water solubility compared with an unmodified physiologically active substance.

10. The compound according to claim 6 or a salt thereof, wherein the improved water solubility is 10 to 1,000,000 times the water solubility of the "unmodified physiologically active substance" in terms of molar concentration.

11. The compound according to claim 6 or a salt thereof, wherein the ester bond or the thioester bond formed between the oxygen atom (O) or the sulfur atom (S) in the glycosylated linker moiety and the carboxy group in the physiologically active substance moiety is cleaved in a manner dependent on pH and/or temperature.

12. A composition comprising a compound according to claim 6 or a salt thereof, wherein 90% or more sugar chains in the compound or the salt thereof are identical in the type of each sugar constituting the sugar chain, binding order, and binding pattern between sugars.

13. A pharmaceutical composition comprising
(I) a compound according to claim 6 or a salt thereof, and
(II) a pharmacologically acceptable carrier.

14. The pharmaceutical composition according to claim 13, wherein the physiologically active substance exerts its activity after administration to a subject.

15. A method of vaccination comprising administering a therapeutically effective amount of the pharmaceutical composition of claim 13.

16. A method for producing a compound comprising a glycosylated linker moiety and a physiologically active substance moiety, or a salt thereof, wherein the glycosylated linker is represented by the following formula (A):

wherein
X represents an oxygen atom (O) having a leaving group or a sulfur atom (S) having a leaving group;
$R^1$ represents —$R^3$—$R^4$—;
$R^3$ represents substituted or unsubstituted $C_1$-$C_5$ alkyl;
$R^4$ represents phenyl;
Y represents —CO—; and
$R^2$ represents a glycosylated cysteinamide;
the sugar chain and the amino acid of the glycosylated cysteinamide are bonded to each other via a linker, the linker being —$CH_2$—CONH—;
the reducing end of the sugar chain is bonded to the nitrogen atom in the linker; and the physiologically active substance has at least one carboxy group, the method comprising the following step:
(a) carrying out condensation reaction so as to form an ester bond or a thioester bond between the oxygen atom (O) or the sulfur atom (S) having a leaving group in the glycosylated linker and the carboxy group of the physiologically active substance.

17. The method for producing a compound or a salt thereof according to claim 16, wherein the step of carrying out condensation reaction is carried out in a state where the glycosylated linker is bonded to a resin for solid-phase synthesis.

18. A method for producing a compound comprising a glycosylated linker moiety and a physiologically active substance moiety, or a salt thereof, wherein the physiologically active substance has at least one carboxy group, the method comprising the following steps:
(a) bonding a linker represented by the following formula (B) to a resin, the linker being represented by the following formula (B):

(B)

wherein
X represents an oxygen atom (O) having a leaving group or a sulfur atom (S) having a leaving group;
$R^1$ represents aryl or —CH$_2$CH$_2$SCH$_2$—;
Y represents —CO—; and
$R^2$ represents an amino acid, wherein in this step, the carboxy group of the amino acid represented by $R^2$ in the linker binds to the resin;
(b) bonding the linker bonded to the resin to the physiologically active substance, wherein the linker binds to the physiologically active substance through an ester bond or a thioester bond formed with the carboxy group of the physiologically active substance by the elimination of the leaving group in the oxygen atom (O) or the sulfur atom (S); and
(c) adding a sugar chain to a side chain of the amino acid or the polypeptide represented by $R^2$ in the linker.

19. A compound or a salt thereof obtainable by a production method according to claim 17.

20. A compound or a salt thereof obtainable by a production method according to claim 18.

21. The glycosylated linker as recited in claim 1, wherein $R^3$ represents —CH$_2$—.

22. The glycosylated linker as recited in claim 1, wherein $R^4$ represents phenyl.

23. The glycosylated linker as recited in claim 1, having structure (34)

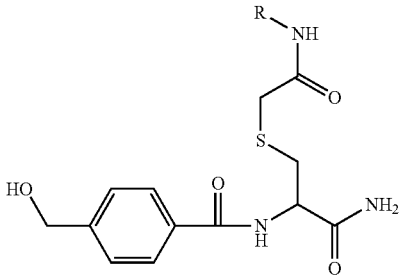

wherein R is a sugar chain.

24. The glycosylated linker according to claim 22, wherein R consists of 4 or more sugar residues.

25. The glycosylated linker according to claim 23, wherein the sugar chain is a biantennary complex-type sugar chain selected from the group consisting of a disialo sugar chain, a monosialo sugar chain, an asialo sugar chain, a di-GlcNAc sugar chain, and a dimannose sugar chain.

26. The glycosylated linker according to claim 23, wherein R is a sugar chain represented by the following formula:

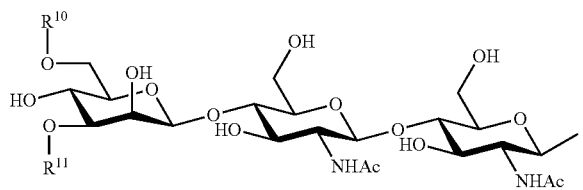

wherein $R^{10}$ and $R^{11}$ are the same or different and each represent

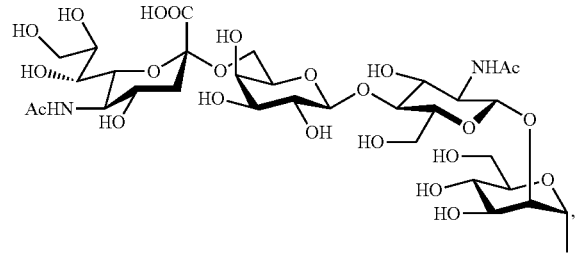

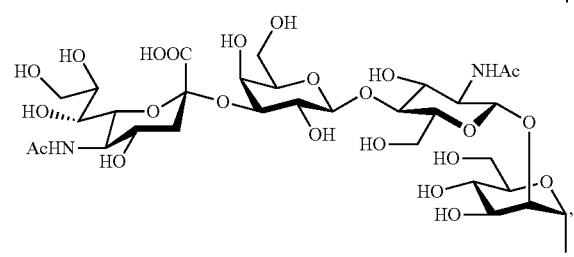

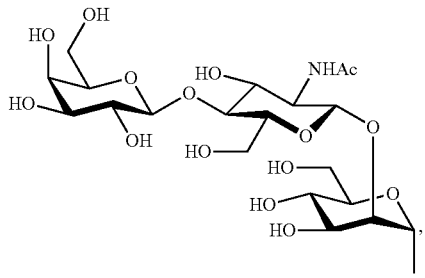

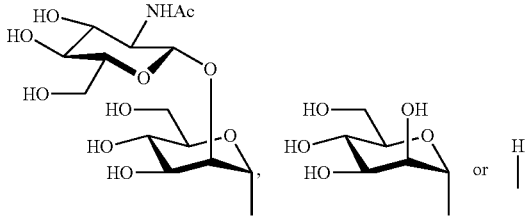

and Ac represents an acetyl group.

27. The composition as recited in claim 12, further comprising one or more additional components (active and/or inert ingredient(s)).

* * * * *